US008609672B2

(12) United States Patent
Russu et al.

(10) Patent No.: US 8,609,672 B2
(45) Date of Patent: Dec. 17, 2013

(54) PIPERAZINYLPYRIMIDINE ANALOGUES AS PROTEIN KINASE INHIBITORS

(75) Inventors: Wade A. Russu, Stockton, CA (US); Hassan M. Shallal, Stockton, CA (US)

(73) Assignee: University of the Pacific, Stockton, CA (US)

( * ) Notice: Subject to any disclaimer, the term of this patent is extended or adjusted under 35 U.S.C. 154(b) by 0 days.

(21) Appl. No.: 13/217,132

(22) Filed: Aug. 24, 2011

(65) Prior Publication Data

US 2012/0053183 A1 Mar. 1, 2012

Related U.S. Application Data

(60) Provisional application No. 61/377,871, filed on Aug. 27, 2010.

(51) Int. Cl.
 *A01N 43/54* (2006.01)
 *A61K 31/519* (2006.01)
 *C07D 239/72* (2006.01)
 *C07D 401/00* (2006.01)

(52) U.S. Cl.
 USPC .............. 514/266.2; 514/266.1; 544/283; 544/284

(58) Field of Classification Search
 USPC .............. 544/283, 284; 514/266.1, 266.2
 See application file for complete search history.

(56) References Cited

U.S. PATENT DOCUMENTS

| 4,559,157 | A | 12/1985 | Smith et al. |
|---|---|---|---|
| 4,608,392 | A | 8/1986 | Jacquet et al. |
| 4,820,508 | A | 4/1989 | Wortzman |
| 4,992,478 | A | 2/1991 | Geria |
| 5,739,127 | A | 4/1998 | Schohe-Loop et al. |
| 5,883,096 | A | 3/1999 | Lowe et al. |
| 5,990,117 | A | 11/1999 | Pamukcu et al. |
| 6,011,035 | A | 1/2000 | Snutch et al. |
| 6,294,533 | B1 | 9/2001 | Snutch et al. |
| 6,476,031 | B1 | 11/2002 | Chakravarty et al. |
| 2005/0054851 | A1 | 3/2005 | Betschart et al. |
| 2005/0059668 | A1 | 3/2005 | Alberati-Giani et al. |
| 2006/0217377 | A1 | 9/2006 | Gonzalez, III et al. |
| 2006/0258672 | A1 | 11/2006 | Barbosa et al. |
| 2007/0100141 | A1 | 5/2007 | Bonaventure et al. |
| 2008/0051414 | A1 | 2/2008 | Hurley et al. |
| 2009/0143399 | A1 | 6/2009 | Hurley et al. |

FOREIGN PATENT DOCUMENTS

| DE | 4423044 A1 | 1/1996 |
|---|---|---|
| DE | 4425146 A1 | 1/1996 |
| EP | 0028473 A1 | 5/1981 |
| EP | 0455510 A2 | 11/1991 |
| JP | 2000-281660 A | 10/2000 |
| JP | 2001-72660 A | 3/2001 |
| JP | 2008-239568 A | 10/2008 |
| JP | 2008-239616 A | 10/2008 |
| JP | 2009-7341 A | 1/2009 |
| WO | 93/04682 A1 | 3/1993 |
| WO | 93/04684 A1 | 3/1993 |
| WO | 95/02405 A1 | 1/1995 |
| WO | 95/07267 A1 | 3/1995 |
| WO | 95/26443 A1 | 9/1995 |
| WO | 96/26196 A2 | 8/1996 |
| WO | 97/32865 A1 | 9/1997 |
| WO | 97/44038 A1 | 11/1997 |
| WO | 98/06715 A1 | 2/1998 |
| WO | 98/11068 A1 | 3/1998 |
| WO | 99/01423 A1 | 1/1999 |
| WO | 99/05121 A1 | 2/1999 |
| WO | 99/19301 A1 | 4/1999 |
| WO | 99/21922 A1 | 5/1999 |
| WO | 99/37304 A1 | 7/1999 |
| WO | 99/54305 A1 | 10/1999 |
| WO | 99/54320 A1 | 10/1999 |
| WO | 00/20401 A1 | 4/2000 |
| WO | 00/66112 A1 | 11/2000 |
| WO | 00/68202 A1 | 11/2000 |
| WO | 00/71529 A1 | 11/2000 |
| WO | 01/44274 A1 | 6/2001 |
| WO | 01/68619 A1 | 9/2001 |
| WO | 01/72710 A1 | 10/2001 |
| WO | 02/00259 A1 | 1/2002 |
| WO | 02/08221 A2 | 1/2002 |
| WO | 02/076926 A1 | 10/2002 |
| WO | 02/086107 A1 | 11/2002 |
| WO | 02/094799 A2 | 11/2002 |
| WO | 03/029199 A1 | 4/2003 |
| WO | 03/032984 A1 | 4/2003 |
| WO | 03/075929 A1 | 9/2003 |
| WO | 03/076400 A1 | 9/2003 |
| WO | 03/082288 A1 | 10/2003 |
| WO | 2004/006916 A1 | 1/2004 |
| WO | 2004/007491 A1 | 1/2004 |
| WO | 2004/010929 A2 | 2/2004 |

(Continued)

OTHER PUBLICATIONS

Pinedo et al (2001) McMahon et all (2001).*
Abdulhameed et al., "Microscopic Modes and Free Energies of 3-Phospholnositide-Department Kinase-1 (PDK1) Binding with Celecoxib and Other Inhibitors", Journal of Physical Chemistry B, vol. 110, No. 51, 2006, pp. 26365-26374.
Akritopoulou-Zane et al., "Kinase-Targeted Libraries: The Design and Synthesis of Novel, Potent, and Selective Kinase Inhibitors", Drug Discovery Today, vol. 14, No. 5/6, Mar. 2009, pp. 291-297.
Andalo et al., "Accurate Mass Measurement of Synthetic Analogues of Prazosine by Matrix-Assisted Laser Desorption/Ionisation Time-of-Fight Mass Spectrometry", Rapid Communications in Mass Spectrometry, vol. 15, 2001, pp. 665-669.
Andersen et al., "Discovery of Selective Aminothiazole Aurora Kinase Inhibitors", ACS Chemical Biology, vol. 3, No. 3, 2008, pp. 108-192.

(Continued)

*Primary Examiner* — Paul V. Ward
(74) *Attorney, Agent, or Firm* — Lily Ackerman; Michael Ward

(57) ABSTRACT

The invention provides novel compounds based on piperazinylpyrimidine derivatives to be used as protein kinase inhibitors. The compounds may be useful in treating or preventing different cellular proliferation disorders, such as cancer. The present invention also provides methods of preparing these compounds, and methods of using the same.

9 Claims, 8 Drawing Sheets

(56) References Cited

FOREIGN PATENT DOCUMENTS

Figure 1:
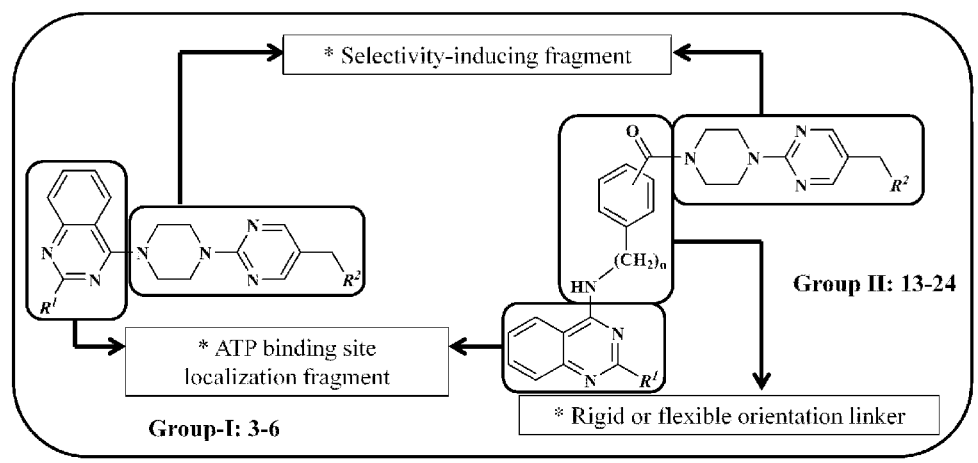

| WO | 2004/076454 A1 | 9/2004 |
|---|---|---|
| WO | 2004/078733 A1 | 9/2004 |
| WO | 2005/014563 A1 | 2/2005 |
| WO | 2005/023260 A1 | 3/2005 |
| WO | 2005/085891 A1 | 7/2005 |
| WO | 2005/103013 A1 | 11/2005 |
| WO | 2005/117909 A2 | 12/2005 |
| WO | 2005/117909 A3 | 12/2005 |
| WO | 2006/040318 A2 | 4/2006 |
| WO | 2006/124874 A2 | 11/2006 |
| WO | 2006/124897 A2 | 11/2006 |
| WO | 2007/011623 A1 | 1/2007 |
| WO | 2007/017728 A2 | 2/2007 |
| WO | 2007/023382 A2 | 3/2007 |
| WO | 2007/023882 A1 | 3/2007 |
| WO | 2007/052843 A1 | 5/2007 |
| WO | 2007/060409 A1 | 5/2007 |
| WO | 2007/063934 A1 | 6/2007 |
| WO | 2007/065261 A1 | 6/2007 |
| WO | 2007/075629 A2 | 7/2007 |
| WO | 2007/082873 A1 | 7/2007 |
| WO | 2007/082880 A1 | 7/2007 |
| WO | 2007/144769 A2 | 12/2007 |
| WO | 2008/017161 A1 | 2/2008 |
| WO | 2008/067121 A2 | 6/2008 |
| WO | 2008/089580 A1 | 7/2008 |
| WO | 2008/146753 A1 | 12/2008 |
| WO | 2008/157500 A1 | 12/2008 |
| WO | 2009/035541 A1 | 3/2009 |
| WO | 2009/042694 A1 | 4/2009 |
| WO | 2009/050242 A2 | 4/2009 |
| WO | 2009/061131 A2 | 5/2009 |
| WO | 2009/063244 A1 | 5/2009 |
| WO | 2009/137503 A1 | 11/2009 |
| WO | 2010/043633 A1 | 4/2010 |

OTHER PUBLICATIONS

Aronov et al., "Kinase-Likeness and Kinase-Privileged Fragments: Toward Virtual Polypharmocology", Journal of Medicinal Chemitry, vol. 51, 2008, pp. 1214-122.

Bamborough et al., "Assessment of Chemical Coverage of Kinome Space and Its Implications for Kinase Drug Discovery", Journal of Medicinal Chemistry, vol. 51, No. 24, 2008, pp. 7898-7914.

Baumli et al., "The Structure of P-TEFb (CDK9/Cyclin T1), its Complex with flavopiridol and Regulation by Phosphorylation", The European Molecular Biology Organization Journal, vol. 27, No. 13, 2008, pp. 1907-1918.

Bavetsias et al., "Hit Generation and Exploration:Imidazo[4,5,-b]Pyridine Derivatives as inhibitors of Aurora Kinases", Bioorganic & Medicinai Chemistry Letters, vol. 17, 2007, pp. 6567-6571.

Boggon et al., "Crystal Structure of the Jak3 Kinase Domain in Complex with a Staurosporine Analog", Blood, vol. 106, No. 3, Aug. 1, 2005, pp. 996-1002.

Bogoyevitch et al., "A New Paradigm for Protein Kinase Inhibition: Blocking Phosphorylation Without Directly Targeting ATP Binding", Drug Discovery Today, vol. 12, No. 15/16, Aug. 2007, pp. 622-633.

Bolognesi et al., "Analogues of Prazosin That Bear a Benextramine-Related Polyamine Backbone Exhibit Different Antagonism Toward α1-Adrenoreceptor Subtypes" Journal of Medicinal Chemistry, vol. 44, No. 3, 2001, pp. 362-371.

Bougherara et al., "The Aberrant Localization of Oncogenic Kit Tyrosine Kinase Receptor Mutants is Reversed on Specific Inhibitory Treatment", Molecular Cancer Research, vol. 7, No. 9, Sep. 8, 2009, pp. 1525-1533.

Burns et al., "Discovery of 2-(α-Methylbenzylamino) Pyrazines as Potent Type II Inhibitors of FMS", Bioorganic & Medicinal Chemistry Letters, vol. 19, 2009, pp. 1206-1209.

Chao et al., "Identification of N-(5-Tert-Butyl-Isoxazol-3-yl)-N'-{4-[7-(2-Morpholin-4-yl-Ethoxy)imidazo- ]2,1-b [1,3] Benzothiazol-2-yl Phenyl}Urea Dihydrochloride (AC220), a Uniquely Potent, Selective, and Efficacious FMS-Like Tyrosine Kinase-3 (FLT3) Inhibitor", Journal of Medicinal Chemistry, vol. 52, No. 23, 2009, pp. 7806-7816.

Christoffersen et al.; "Cancer Therapy Targeted at Cellular Signal Transduction Mechanisms: Strategies, Clinical Results, and Unresolved Issues"; European Journal of Pharmacology, vol. 625; 2009, pp. 6-22.

Cohen et al., "Approval Summary for Imatinib Mesylate Capsules in the Treatment of Chronic Myelogenous Leukemia", Clinical Cancer Research, vol. 8; May 2002, pp. 935-942.

Copeland, Robert A., "Mechanistic Considerations in High-Throughput Screening", Analytical Biochemistry, vol. 320, 2003, pp. 1-12.

Dagher et al., "Approval Summary: Imatinib Mesylate in the Treatment of Metastatic and/or Unresectable Malignant Gastrointestinal Stromal Tumors", Clinical Cancer Research, vol. 8, Oct. 2002, pp. 3034-3038.

Davies et al., "Specificity and Mechanism of Action of Some Commonly Used Protein Kinase Inhibitors", Biochemical Journal, vol. 351, 2000, pp. 95-105.

Eglen et al., "The Current Status of Drug Discovery Against the Human Kinome", Assay and Drug Development Technologies, vol. 7, No. 1, Feb. 2009, pp. 22-43.

Eglen et al., "Human Kinome Drug Discovery and the Emerging Importance of Atypical Allosteric Inhibitors", Expert Opinion on Drug Discovery, vol. 5, No. 3, 2010, pp. 277-290.

Fabian et al., "A Small Molecule—Kinase Interaction Map for Clinical Kinase Inhibitors", Nature Biotechnology, vol. 23, No. 3, Mar. 2005, pp. 329-336.

Fedorov et al., "A Systematic Interaction Map of Validated Kinase Inhibitors with Ser/Thr Kinases", Proceedings of the National Academy of Sciences, vol. 14, No. 51, Dec. 18, 2007, pp. 20523-20528.

Grepin et al., "Molecular Mechanisms of Resistance to Tumor Anti-Angiogenic Strategies", Journal of Oncology, vol. 2010, 2010, pp. 1-8.

Gajiwala et al., "KIT Kinase Mutants Show Unique Mechanisms of Drug Resistance to Imatinib and Sunitinib in Gastrointestinal Stromal Tumor Patients", Proceedings of the National Academy of Sciences, vol. 106, No. 5, Feb. 3, 2009, pp. 1542-1547.

Hanano et al., "Novel DMARDs on the Basis of a New Concept of Dual Cytokine Regulation, TNF-α Suppression and IL-10 Augmentation", Bioorganic & Medicinal Chemistry Letters, vol. 10, 2000, pp. 881-884.

Heinrich et al., "PDGFRA Activating Mutations in Gastrointestinal Stromal Tumors", Science, vol. 299, Jan. 31, 2003, pp. 708-710.

Huang et al., "Kinase Selectivity Potential for Inhibitors Targeting the ATP Binding Site: A Network Analysis", Bioinformatics, vol. 26, No. 2, 2010, pp. 198-204.

Invitation to Pay Additional Fees and Partial Search Report received for PCT Patent Application No. PCT/US2011/048999, mailed on Oct. 20, 2011, 6 pages.

Jiang et al., "Examining the Chirality, Conformation and Selective Kinase Inhibition of 3-((3R,4R)-4-~Methyl-3-(Methyl(7H-Pyrrolo[2,3-d]Pyrimidin-4-yl)Amino)Piperidin-1-yl)-3-Oxopropanenitrile (CP-690,550)", Journal of Medicinal Chemistry, vol. 51, 2008, pp. 8012-3018.

Karaman et al., "A Quantitative Analysis of Kinase Inhibitor Selectivity", Nature Biotechnology, vol. 26, No. 1, Jan. 2008, pp. 127-132.

Kinnings et al., "Binding Site Similarity Analysis for the Functional Classification of the Protein Kinase Family", Journal of Chemical Information and Modeling, vol. 49, No. 2, 2009, pp. 318-329.

Kirkland et al., "Non-ATP Competitive Protein Kinase Inhibitors as Anti-Tumor Terapeutics", Biochemical Pharmacology, vol. 77, 2009, pp. 1561-1571.

Knight et al., "Features of Selective Kinase Inhibitors", Chemistry & Biology, vol. 12, Jun. 2005, pp. 621-637.

Kolb et al., "Dicovery of Kinase Inhibitors by High-Throughput Docking and Scoring Based on a Transferable Linear Interaction Energy Model", Journal of Medicinal Chemistry, vol. 51, No. 5, 2008, pp. 1179-1188.

Liegl-Atzwanger et al., "Gastrointestinal Stromal Tumors", Virchows Arch., vol. 456, 2010, pp. 111-127.

(56) References Cited

OTHER PUBLICATIONS

Ma et al., "The Challenge of Selecting Protein Kinase Assays for Lead Discovery Optimization", Expert Opinion on Drug Discovery, vol. 3, No. 6, 2008, pp. 1-22.

Martin et al., "Inhibition of MCL-1 Enhances Lapatinib Toxicity and Overcomes Lapatinib Resistance via BAK-Dependent Autophagy", Cancer and Biology & Therapy, vol. 8, No. 21, Nov. 1, 2009, pp. 2084-2096.

Masson et al., "Oncogenic Signaling from the Hematopoietic Growth Factor Receptors c-Kit and Flt3", Cellular Signalling, vol. 21, 2009, pp. 1717-1726.

McDermott et al., "Personalized Cancer Therapy With Selective Kinase Inhibitors: An Emerging Paradigm in Medical Oncology", Journal of Clinical Oncology, vol. 27, No. 33, Nov. 20, 2009, pp. 5650-5659.

McGovern et al., "Kinase Inhibitors: Not Just for Kinases Anymore", Journal of Medicinal Chemistry, vol. 46, No. 8, 2003, pp. 1478-1483.

Morphy, Richard, "Selectively Nonselective Kinase Inhibition: Striking the Right Balance", Journal of Medicinal Chemistry, vol. 53, No. 4, 2010, pp. 1413-1437.

Nautiyal et al., "ErbB-Inhibitory Protein: A Modified Ectodomain of Epidermal Growth Factor Receptor Synergizes with Dasatinib to Inhibit Growth of Breast Cancer Cells", Molecular Cancer Therapeutics, vol. 9, No. 6, Jun. 2010, pp. 1503-1514.

Oliveras-Ferraros et al., "Growth and Molecular Interactions of the Anti-EGFR Antibody Cetuximab and the DNA Cross-Linking Agent Cisplatin in Gefitinib-Resistant MDA-MB-468 Cells: New Prospects in the Treatment of Triple-Negative/Basal-like Breast Cancer", International Journal of Oncology, vol. 33, 2008, pp. 1165-1176.

Pan et al., "MK-2461, A Novel Multitargeted Kinase Inhibitor, Preferentially Inhibits the Activated c-Met Receptor", Cancer Research, vol. 70, No. 4, Feb. 15, 2010, pp. 1524-1533.

Parikh et al., "Kinome Profiling of Clinical Cancer Specimens", Cancer Research, vol. 70, No. 7, 2010, pp. 2575-2578.

Pasini et al., "Multiple Gastrointestinal Stromal and Other Tumors Caused by Platelet-Derived Growth Factor Receptor α Gene Mutations: A Case Associated with a Germline V561D Defect", The Journal of Clinical Endocrinology & Metabolism, vol. 92, No. 9, 2007, pp. 3728-3732.

Peterelli et al., "From Single- to Multi-Target Drugs in Cancer Therapy: When Aspecificity Becomes an Advantage", Current Medicinal Chemistry, vol. 15, No. 5, 2008, pp. 422-432.

Pettus et al.; "Discovery and Evaluation of 7-Alkyl-1,5-bis-arylpyrazolopyridiriones as Highly Potent, Selective, and Orally Efficacious Inhibitors of p38r Mitogen-Activated Protein Kinase", Journal of Medicinal Chemistry, vol. 53, No. 7, 2010, pp. 2973-2985.

Rixe et al., "A Randomized, Phase II, Dose-Finding Study of the Pan-ErbB Receptor Tyrosine-Kinase Inhibitor CI-1033 in Patients with Pretreated Metastatic Breast Cancer", Cancer Chemother Pharmacol, vol. 64, 2009, pp. 1139-1148.

Seltzer, Edgar, "Impact of Molecular Targets in Cancer Drug Development Historical Influence and Future Perspectives", Expert Review of Clinical Pharmacology, vol. 3, No. 2, 2010, pp. 161-163.

Shallal et al., "Discovery, Synthesis, and Investigation of the Antitumor Activity of Novel Piperazinylprimidine Derivatives", European Journal of Medicinal Chemistry, vol. 46, 2011, pp. 2043-2057.

Shoemaker, Robert H., "The NCI60 Human Tumour Cell Line Anticancer Drug Screen", Nature Reviews Cancer, vol. 6, Oct. 2006, pp. 813-823.

Skehan et al., "New Calorimetric Cytotoxicity Assay for Anticancer-Drug Screening", Journal of the National Cancer Institute, vol. 82, 1990, 8 pages.

Smyth et al., "Measuring and Interpreting the Selectivity of Protein Kinase Inhibitors" Journal of Chemical Biology, vol. 2, 2009, pp. 131-151.

Stamos et al., "Structure of the Epidermal Growth Factor Receptor Kinase Domain Alone and in Complex with a 4-Anilinoquiriazdine Inhibitor", The Journal of Biological Chemistry, vol. 277, No. 48, 2002, pp. 46265-48272.

Suijkerbuijk et al., "Development of Novel, Highly Potent Inhibitors of V-RAF Murine Sarcoma Viral Oncogene Hornologue B1 (BRAF): Increasing Cellular Potency through Optimization of a Distal Heteroaromatic Group", Journal of Medicinal Chemistry, vol. 53, No. 7, 2010, pp. 2741-2756.

Takimoto, Chris H., "Anticancer Drug Development at the US National Cancer Institute" Cancer Chemother Pharmacol, vol. 52, 2003, pp. S29-S33.

Weisberg et al., "Effects of PKC412, Nilotinib, and Imatinib Against GIST-Associated PDGFRA Mutants With Differential Imatinib Sensitivity", Gastroenterology, vol. 131, No. 6, 2006, pp. 1734-1742.

Weisbero et al., "Antileukemic Effects of the Novel, Mutant FLT3 Inhibitor NVP-AST487: Effects on PKC412-Sensitive and -Resistant FLT3-Expressing Cells", Blood, vol. 112, No. 13, Dec. 15, 2008, pp. 5161-5170.

Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research, vol. 64, Sep. 15, 2004, pp. 6652-6659.

Yang et al., "Inhibition of Casein Kinase I-Epsilon Induces Cancer-Cell-Selective, PERIOD2-Dependent Growth Arrest", Genome Biology, vol. 9, No. 6, 2008, pp. R92.1-R92.13.

Yun et al., "Structures of Lung Cancer-Derived EGFR Mutants and Inhibitor Complexes: Mechanism of Activation and Insights into Differential Inhibitor Sensitivity", Cancer Cell, vol. 11, Mar. 2007, pp. 217-227.

International Search Report and Written Opinion received for PCT Patent Application No. PCT/US2011/048999, mailed on Jan. 16, 2012, 16 pages.

Smith et al., "March's Advanced Organic Chemistry: Reactions, Mechanisms and Structure" John Wiley & Son, 6th edition, 2007, 6 pages (Table of Contents only).

Becker, Irwin, "Preparation of Derivatives of 1-(2-Pyrimidinyl)Piperazine as Potential Antianxiety, Antidepressant, and Antipsychotic Agents", Journal of Heterocyclic Chemistry, vol. 45, No. 4, Jul./Aug. 2008, pp. 1005-1022.

Berge et al., "Pharmaceutical Salts", Journal of Pharmaceutical Sciences, vol. 66, No. 1, Jan. 1977, pp. 1-19.

\* cited by examiner (A)

(B)

PIPERAZINYLPYRIMIDINE ANALOGUES AS PROTEIN KINASE INHIBITORS

CROSS-REFERENCE TO RELATED APPLICATION

This application claims the benefit under 35 U.S.C. §119(e) of U.S. Provisional Application No. 61/377,871, filed Aug. 27, 2010, which is hereby incorporated by reference in the present disclosure in its entirety.

BACKGROUND

1. Field

The present disclosure relates generally to piperazinylpyrimidine analogs and uses thereof. The invention also relates to methods of preparing these compounds.

2. Related Art

The human kinome, represented by 518 kinases, is a widely investigated protein family on biological, chemical, and clinical levels. Protein kinases are involved in the majority of signal transduction pathways regulating the cell machinery of survival, proliferation, and maintenance. Accordingly, several pathological abnormalities are correlated with aberrations in the operational integrity and accuracy of certain kinases inside the cell, making kinases attractive targets for treating, diagnosing, and establishing personalized therapies of various disorders such as different malignancies, neurodegenerative disorders, rheumatoid arthritis, autoimmune diseases, and others (Eglen, R. M.; Reisine, T. *Assay and Drug Development Technologies* 2009, 7, 22-43; Eglen, R. M.; Reisine, T. *Expert Opinion on Drug Discovery* 2010, 5, 277-290; Parikh, K.; Peppelenbosch, M. P. *Cancer Research* 2010, 70, 2575-2578; McDermott, U.; Settleman, J. *Journal of Clinical Oncology* 2009, 27, 5650-5659).

Kinase inhibitors, either small molecules or monoclonal antibodies, represent a class of molecularly targeted anticancer agents; approximately 14 kinase targeting agents have earned FDA approval during the last two decades as either anticancer or antiangiogenic agents. In comparison, not as many agents targeting other cancer-relevant families such as Bcl-2 proteins, histone deacetylases, and phosphatases, have gained regulatory approval. Furthermore, the discovery, preclinical, and clinical development of novel kinase inhibitors currently are the focus of pharmaceutical industry research efforts, especially those seeking novel and effective cancer controlling agents (Selzer, E. *Expert Review of Clinical Pharmacology* 2010, 3, 161-163).

The design of selective kinase inhibitors has proven to be challenging due to the conservation of the ATP binding site, targeted by most inhibitors, among different kinases. Several design strategies, both computer assisted, bioinformatics aided, and structure based, have been implemented to tailor more selective kinase inhibitors against a subset of kinases or certain kinase subfamilies (Eglen, R. M.; Reisine, T. *Expert Opinion on Drug Discovery* 2010, 5, 277-290; Akritopoulou-Zanze, I.; Hajduk, P. J. *Drug Discovery Today* 2009, 14, 291-297; Bogoyevitch, M. A.; Fairlie, D. P. *Drug Discovery Today* 2007, 12, 622-633; Huang, D. et al. *Bioinformatics* 2009, 26, 198-204; Kirkland, L. O.; McInnes, C. *Biochemical Pharmacology* 2009, 77, 1561-1571; Smyth, L. A.; Collins, I. *Journal of Chemical Biology* 2009, 2, 131-151; Aronov, A. M. et al. *Journal of Medicinal Chemistry* 2008, 51, 1214-1222; Knight, Z. A.; Shokat, K. M. *Chemistry and Biology* 2005, 12, 621-637). One successful example is lapatinib, which is known to be a selective inhibitor against many wild-type and mutant EGFR subfamily members and is currently utilized clinically in combination with capecitabine for metastatic breast cancer. In contrast, sunitinib, another successfully marketed kinase inhibitor, has been shown in several studies to be a highly promiscuous agent capable of interacting with more than 15% of kinases with a very high affinity (Kd<100 nM) (Morphy, R. *Journal of Medicinal Chemistry* 2010, 53, 1413-1437; Karaman, M. W. et al. *Nature Biotechnology* 2008, 26, 127-132). The selectivity of lapatinib compared to the promiscuity of sunitinib is usually rationalized by the observation that lapatinib is a type-II inhibitor which binds to the ATP-binding site as well as penetrating the adjacent allosteric binding site of its target kinases, whereas sunitinib is a type-I inhibitor that binds mainly to the ATP-binding site of several kinases (Gajiwaia, K. S. *Proceedings of the National Academy of Sciences of the United States of America* 2009, 106, 1542-1547; Wood, E. R. et al. *Cancer Research* 2004, 64, 6652-6659). However, it is unjustified, according to several published reports, to claim that every type-I kinase inhibitor is promiscuous and that every type-II inhibitor is selective (Karaman, M. W. et al. *Nature Biotechnology* 2008, 26, 127-132). Additionally, a given small molecule kinase inhibitor usually tends to recognize a given conformational ensemble of its target kinase(s) that may happen to differentially belong to either the active and/or the inactive state. That is to say that a type-I inhibitor, for example, may still bind to the inactive form of its kinase but with less affinity than with the active state. Considering another dimension of variability, some inhibitors interact potently with both the active and the inactive forms of their targeted kinases. For example, MK-2461 is able to bind with considerable potency to both the phosphorylated and the unphosphorylated forms of c-MET kinase with a measured binding constant (Kd) of 4.4 and 27.2 nM respectively (Pan, B. S. et al. *Cancer Research* 2010, 70, 1524-1533). Contrary to the behavior of MK-2461, sunitinib exhibits a strong differential selectivity towards the unactivated wild-type KIT versus the active form (Gajiwaia, K. S. et al. *Proceedings of the National Academy of Sciences of the United States of America* 2009, 106, 1542-1547). Generally speaking, the clinical fact that both lapatinib and sunitinib have successfully helped save or at least improve the life quality of certain cancer patient populations illustrates that, when it comes to kinase inhibitors, it is arguable that selectivity is always a virtue and non-selectivity is a constant drawback. In fact, some kinase modulating agents may achieve better clinical outcomes via targeting several kinases whereas others can cause troublesome side effects even while being selective (Petrelli, A.; Giordano, S. *Current Medicinal Chemistry* 2008, 15, 422-432). Moreover, small molecules generally and kinase inhibitors specifically are usually promiscuous hitters of several protein families and that could be why not all potent kinase inhibitors survive through the drug development process (McGovern, S. L.; Shoichet, B. K. *Journal of Medicinal Chemistry* 2003, 46, 1478-1483).

The phenomenon of kinase inhibitors being mostly non-selective has inspired the founding of several high-throughput kinase profiling screens in order to determine intended as well as off-target kinases affected by a given kinase inhibitor (Karaman, M. W. et al. *Nature Biotechnology* 2008, 26, 127-132; Fedorov, O. et al. *Proceedings of the National Academy of Sciences of the United States of America* 2007, 104, 20523-20528; Ma, H. et al. *Expert Opinion on Drug Discovery* 2008, 3, 607-621). These screens have been used to investigate the kinase binding potential or the functional inhibitory activity of a given small molecule against a large panel of kinases and thereby have facilitated uncovering some of the structural features relevant to promiscuity. However, it is now appreciated that a given kinase may be more promiscuous than another even with a difference of only a few amino acids because the conformational space of the kinase depends on structural features at the primary, secondary, and tertiary levels (Bamborough, P. et al. *Journal of Medicinal Chemistry* 2008, 51, 7898-7914). A deeper understanding of protein kinase promiscuity in cases where there are correlations between the ATP-binding sites of certain subfamilies that are not closely related based on sequence similarity is needed (Kinnings, S. L.; Jackson, R. M. *Journal of Chemical Information and Modeling* 2009, 49, 318-329). Resistance through several mechanisms, most frequently single point mutation, has been developed by cancer cells towards several kinase inhibitors; those who target proliferation and/or angiogenesis including both selective and non-selective kinase inhibitors (Christoffersen, T. et al. *European Journal of Pharmacology* 2009, 625, 6-22; Martin, A. P. et al. *Cancer Biology and Therapy* 2010, 8, 2084-2096; Pages, G.; Grepin, R. *Journal of Oncology* 2010).

Thus, there remains a need for novel protein kinase inhibitor compounds with desirable pharmaceutical properties.

SUMMARY

The present invention provides piperazinylpyrimidine analogs which may inhibit cell proliferation and/or induce cell apoptosis. The compounds comprise a piperazinylpyrimidine core group that is linked to a quinazoline or a quinazoline derivative. The quinazoline derivative may include a six-membered pyrimidine ring fused to an optionally substituted aryl or heteroaryl ring with 5-6 ring atoms.

The compounds of the invention exert biological activity in assays described herein. For example, compounds of the invention are cytotoxic in a cellular screening assay described herein. Though not limiting the invention by any theory, it is believed that the compounds localize in the hinge region of protein kinases and extend either through the ATP-binding groove or towards the adjacent allosteric site. The present invention also provides methods of preparing these compounds, and methods of using the same.

In one aspect, the present invention provides a compound of formula (I), (II), or (III):

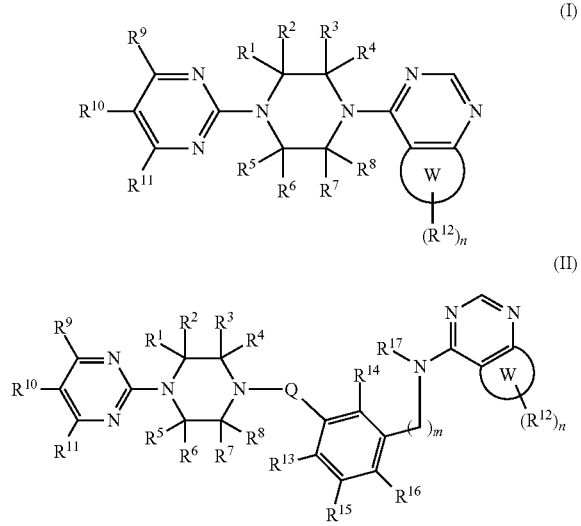

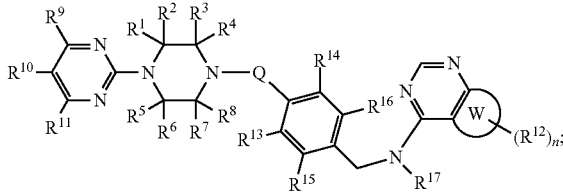

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, $NRCOOR$, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and wherein each R is optionally substituted, with the proviso that $R^{10}$ for formula (I) must not be hydrogen; and
each $R^{17}$ is independently selected from hydrogen or optionally substituted alkyl;
or a pharmaceutically acceptable salt thereof. In some embodiments, Q is C=O. In other embodiments, each $R^1$, $R^2$, $R^3$, $R^4$, $R^5$, $R^6$, $R^7$, and $R^8$ is hydrogen. In certain embodiments, each $R^9$ and $R^{11}$ is independently selected from hydrogen, optionally substituted alkyl, optionally substituted aryl, halo, OR, $NR_2$, SR, CN, COOR, $CONR_2$, COR, CH(OH)R, and $NO_2$. In some embodiments, each $R^{10}$ is independently selected from optionally substituted alkyl, optionally substituted aryl, halo, OR, $NR_2$, SR, CN, COOR, $CONR_2$, COR, CH(OH)R, and $NO_2$. In some preferred embodiments, each $R^{10}$ is independently selected from optionally substituted alkyl or optionally substituted aryl. In other preferred embodiments, each $R^{10}$ is —$(CH_2)_p$—Ar, wherein p is 1-2 and Ar is optionally substituted phenyl. In other preferred embodiments, each $R^9$ and $R^{11}$ is hydrogen and each $R^{10}$ is optionally substituted alkyl. In some embodiments, each $R^{10}$ is independently selected from methyl, ethyl, propyl, isopropyl, butyl, isobutyl, sec-butyl, tert-butyl, pentyl, neopentyl, and benzyl. In some preferred embodiments, each $R^{10}$ is independently selected from optionally substituted ethyl or benzyl. In some embodiments, each $R^{12}$ may be independently selected from optionally substituted alkyl, optionally substituted aryl, halo, OR, $NR_2$, SR, CN, COOR, $CONR_2$, COR, CH(OH)R, and $NO_2$. In some preferred embodiments, each $R^{12}$ is hydrogen. In the above formulas (I), (II), and (III), W represents a ring that includes two ring atoms of one of the pyrimidine rings. W is typically an optionally substituted 5- or 6-membered aromatic or heteroaromatic ring that is optionally fused to another substituted aryl, heteroaryl, heterocyclic, or carbocyclic group. Frequently, W is an optionally substituted 6-membered ring having the following structure:

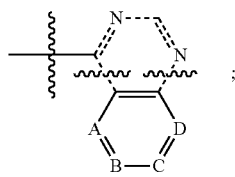

wherein each A, B, C, and D is independently N or CR$^{12}$ in any combination. In certain embodiments, W may include one of the following structures:

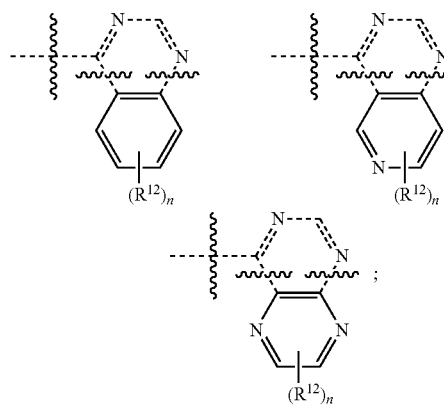

wherein each R$^{12}$ is independently selected from the group consisting of hydrogen, optionally substituted alkyl, optionally substituted aryl, halo, OR, NR$_2$, SR, CN, COOR, CONR$_2$, COR, CH(OH)R, and NO$_2$. In other embodiments, W may include one of the following structures:

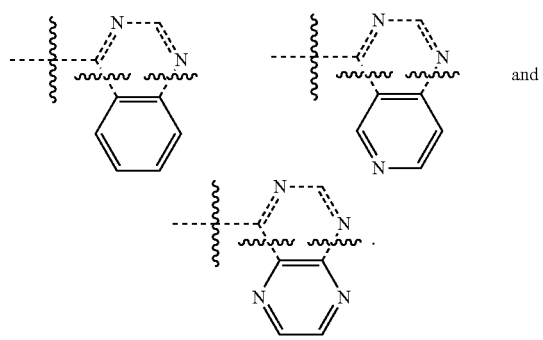

In some preferred embodiments, W is:

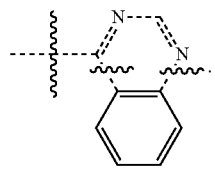

W may also represent an optionally substituted 5-membered ring having the following structure:

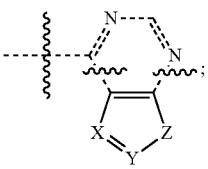

wherein X and Y are N or CR$^{12}$;
Z is selected from the group consisting of NR$^{20}$, O, and S; and
R$^{20}$ is hydrogen or R$^{12}$. In other embodiments, W may include one of the following structures:

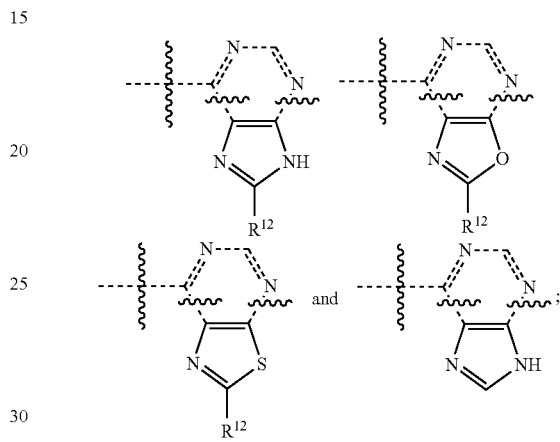

wherein each R$^{12}$ is independently selected from the group consisting of hydrogen, optionally substituted alkyl, and optionally substituted aryl. In certain embodiments, W may include one of the following structures:

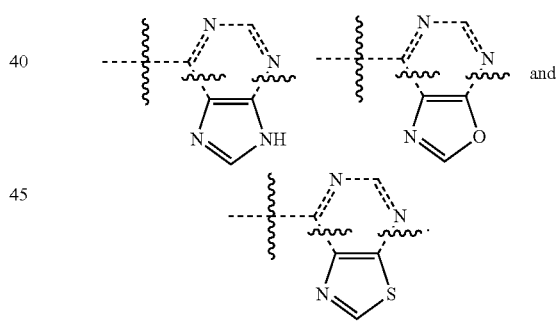

W may also represent an optionally substituted 5-membered ring having the following structure:

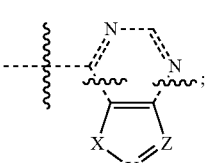

wherein X is selected from the group consisting of NR$^{20}$, O, and S;
Y and Z are N or CR$^{12}$; and
R$^{20}$ is hydrogen or R$^{12}$. In certain embodiments, W is selected from the group consisting of:

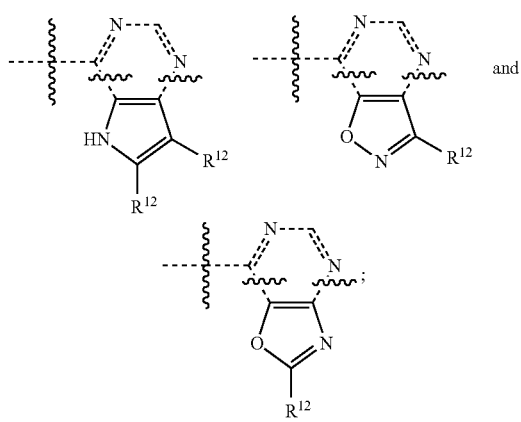

wherein each $R^{12}$ is independently selected from the group consisting of hydrogen, optionally substituted alkyl, and optionally substituted aryl. In certain embodiments, W may include one of the following structures:

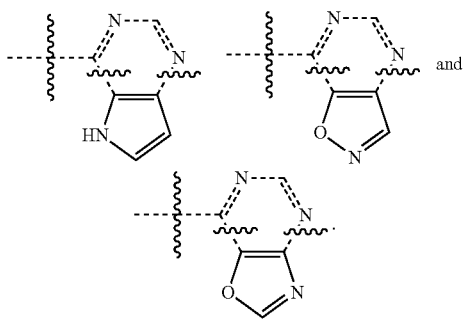

In some preferred embodiments, the compound is:

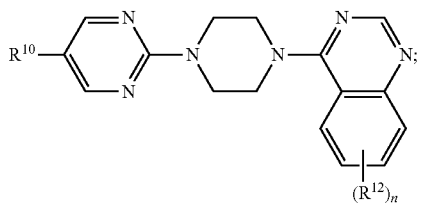

wherein $R^{10}$ is selected from the group consisting of optionally substituted alkyl and optionally substituted aryl; and wherein each $R^{12}$ is independently selected from the group consisting of hydrogen, optionally substituted alkyl, optionally substituted aryl, halo, OR, $NR_2$, SR, CN, COOR, $CONR_2$, COR, CH(OH)R, and $NO_2$. In some preferred embodiments, the compound is:

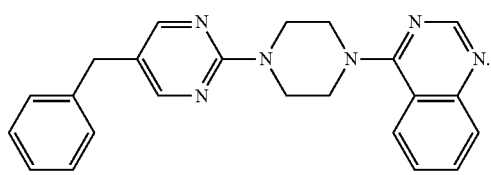 [SMILES: c1ccc(Cc2cnc(N3CCN(c4ncnc5ccccc45)CC3)nc2)cc1]

In some preferred embodiments, the compound is:

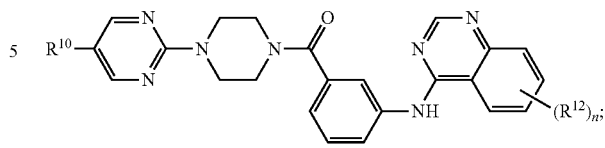

wherein $R^{10}$ is selected from the group consisting of optionally substituted alkyl and optionally substituted aryl; and wherein each $R^{12}$ is independently selected from the group consisting of hydrogen, optionally substituted alkyl, optionally substituted aryl, halo, OR, $NR_2$, SR, CN, COOR, $CONR_2$, COR, CH(OH)R, and $NO_2$. In some preferred embodiments, the compound is:

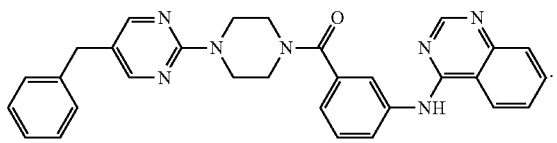 [SMILES: O=C(c1cccc(Nc2ncnc3ccccc23)c1)N1CCN(c2ncc(Cc3ccccc3)cn2)CC1]

In some preferred embodiments, the compound is:

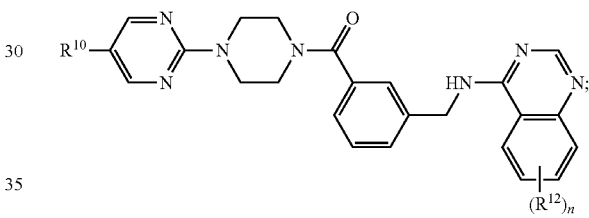

wherein $R^{10}$ is selected from the group consisting of optionally substituted alkyl and optionally substituted aryl; and wherein each $R^{12}$ is independently selected from the group consisting of hydrogen, optionally substituted alkyl, optionally substituted aryl, halo, OR, $NR_2$, SR, CN, COOR, $CONR_2$, COR, CH(OH)R, and $NO_2$. In some preferred embodiments, the compound is:

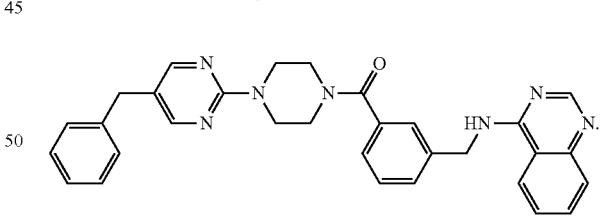

In some preferred embodiments, the compound is:

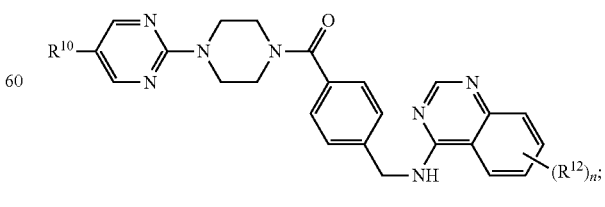

wherein $R^{10}$ is selected from the group consisting of optionally substituted alkyl and optionally substituted aryl;

and wherein each $R^{12}$ is independently selected from the group consisting of hydrogen, optionally substituted alkyl, optionally substituted aryl, halo, OR, $NR_2$, SR, CN, COOR, $CONR_2$, COR, CH(OH)R, and $NO_2$. In some preferred embodiments, the compound is:

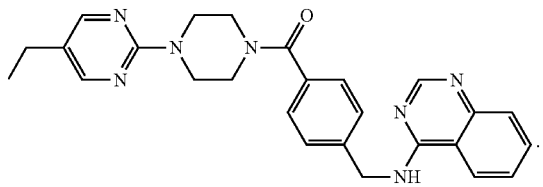 [SMILES: CCc1cnc(N2CCN(C(=O)c3ccc(CNc4ncnc5ccccc45)cc3)CC2)nc1]

In some embodiments, one or more $R^9$, $R^{10}$, $R^{11}$ or $R^{12}$ are independently halo. In some preferred embodiments, each $R^{19}$ is bromo. In some preferred embodiments, each $R^{12}$ is fluoro. In some preferred embodiments, the compound is:

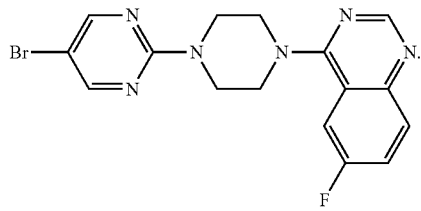

In some preferred embodiments, the compound is:

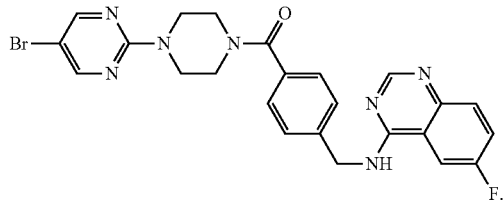 [SMILES: O=C(c1ccc(CNc2ncnc3ccc(F)cc23)cc1)N1CCN(c2ncc(Br)cn2)CC1]

The present invention also provides pharmaceutical compositions including a compound having any one of the above formulas and at least one pharmaceutically acceptable excipient.

The present invention also provides use of a compound having any one of the above formulas to manufacture a medicament. In some embodiments, the medicament is a medicament for the treatment of a proliferative disorder. The present invention also provides a method of treating a proliferative disorder by administering a compound having any one of the above formulas.

The present invention also provides a method to identify a molecule that modulates protein kinase activity. The method includes screening a compound having any one of the above formulas to identify a compound having an effect on the activity of a protein kinase.

The present invention also provides a method to treat a proliferative disorder. The method includes administering to a subject in need of such treatment, an effective amount of a compound of formula (I), (II), or (III):

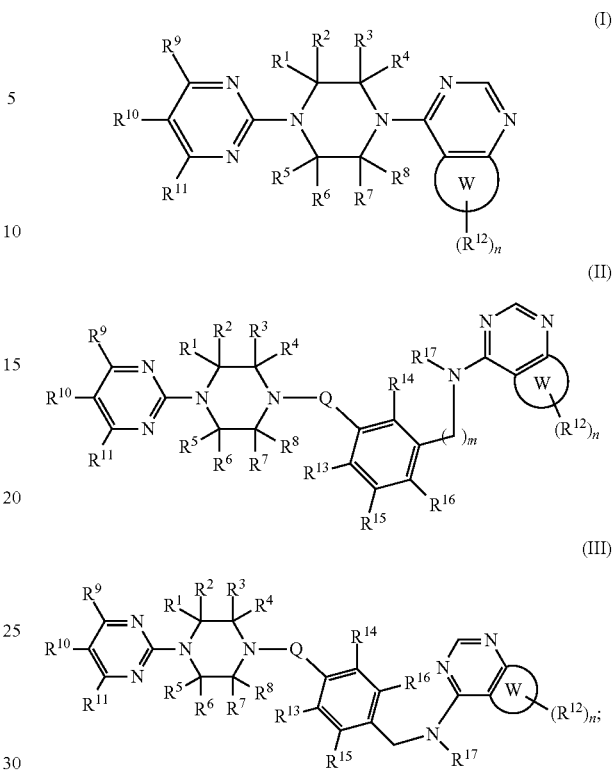

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and wherein each R is optionally substituted; and
each $R^{17}$ is independently selected from hydrogen or optionally substituted alkyl;
or a pharmaceutically acceptable salt thereof. In some embodiments, the proliferative disorder is a tumor or a cancer in a human or animal subject. In some preferred embodiments, the cancer is selected from the group consisting of leukemia, non-small cell lung cancer, colon cancer, central nervous system (CNS) cancer, melanoma, ovarian cancer, renal cancer, prostate cancer, and breast cancer.

The present invention also provides a method to reduce cell proliferation. The cells sometimes are in a cell line, such as a cancer cell line (e.g., breast cancer, prostate cancer, pancreatic cancer, lung cancer, hemopoietic cancer, colorectal cancer, skin cancer, ovarian cancer cell line), for example. In some embodiments, the cancer cell line is a leukemia, non-small cell lung cancer, colon cancer, central nervous system (CNS) cancer, melanoma, ovarian cancer, renal cancer, prostate cancer, or breast cancer cell line. The cells sometimes are in a tissue, can be in a subject, at times are in a tumor, and sometimes are in a tumor in a subject. The method includes administering to a cell in an in vitro or in vivo environment, an effective amount of a compound of formula (I), (II), or (III):

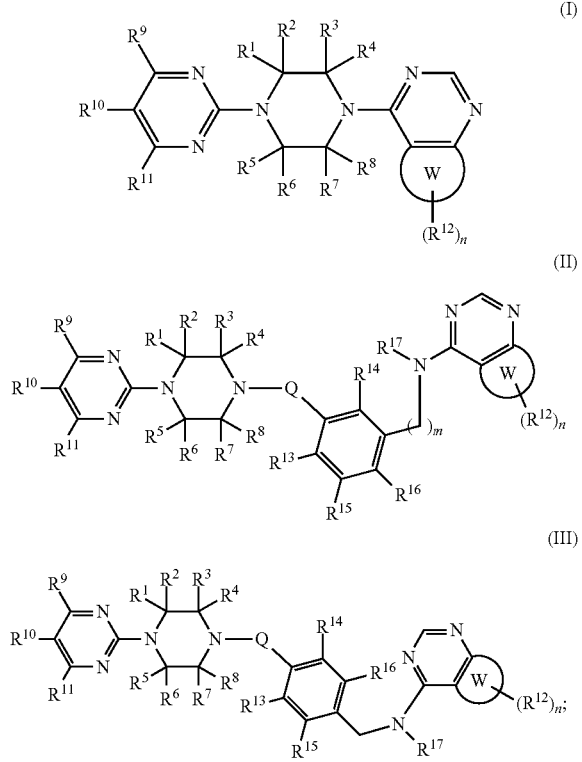

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted; and
each $R^{17}$ is independently selected from hydrogen or optionally substituted alkyl;
or a pharmaceutically acceptable salt thereof.

The present invention also provides a method to induce cell death. The method includes administering to a cell in an in vitro or in vivo environment, an effective amount of a compound of formula (I), (II), or (III):

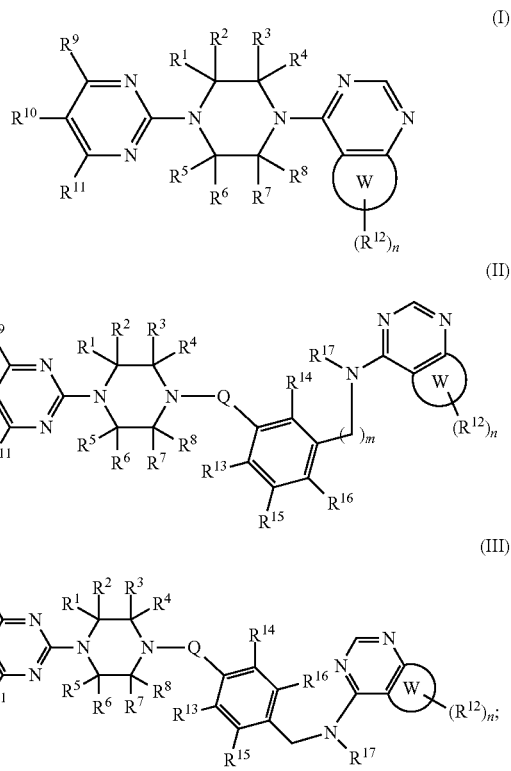

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted; and
each $R^{17}$ is independently selected from hydrogen or optionally substituted alkyl;
or a pharmaceutically acceptable salt thereof.

The above methods for reducing cell proliferation and/or inducing cell death may also be practiced in combination with a procedure and/or a chemotherapeutic agent. Examples of procedures that may be used in combination with the methods of the present invention include but are not limited to radiotherapy or surgery. In certain embodiments, the compounds of the present invention are administered in combination with one or more additional compounds, and used to reduce cell proliferation, induce cell death, and/or ameliorate a cell proliferative disorder.

DESCRIPTION OF DRAWING FIGURES

FIG. 1. Design strategy of compounds 3-6 and 13-24.

Figure 2:
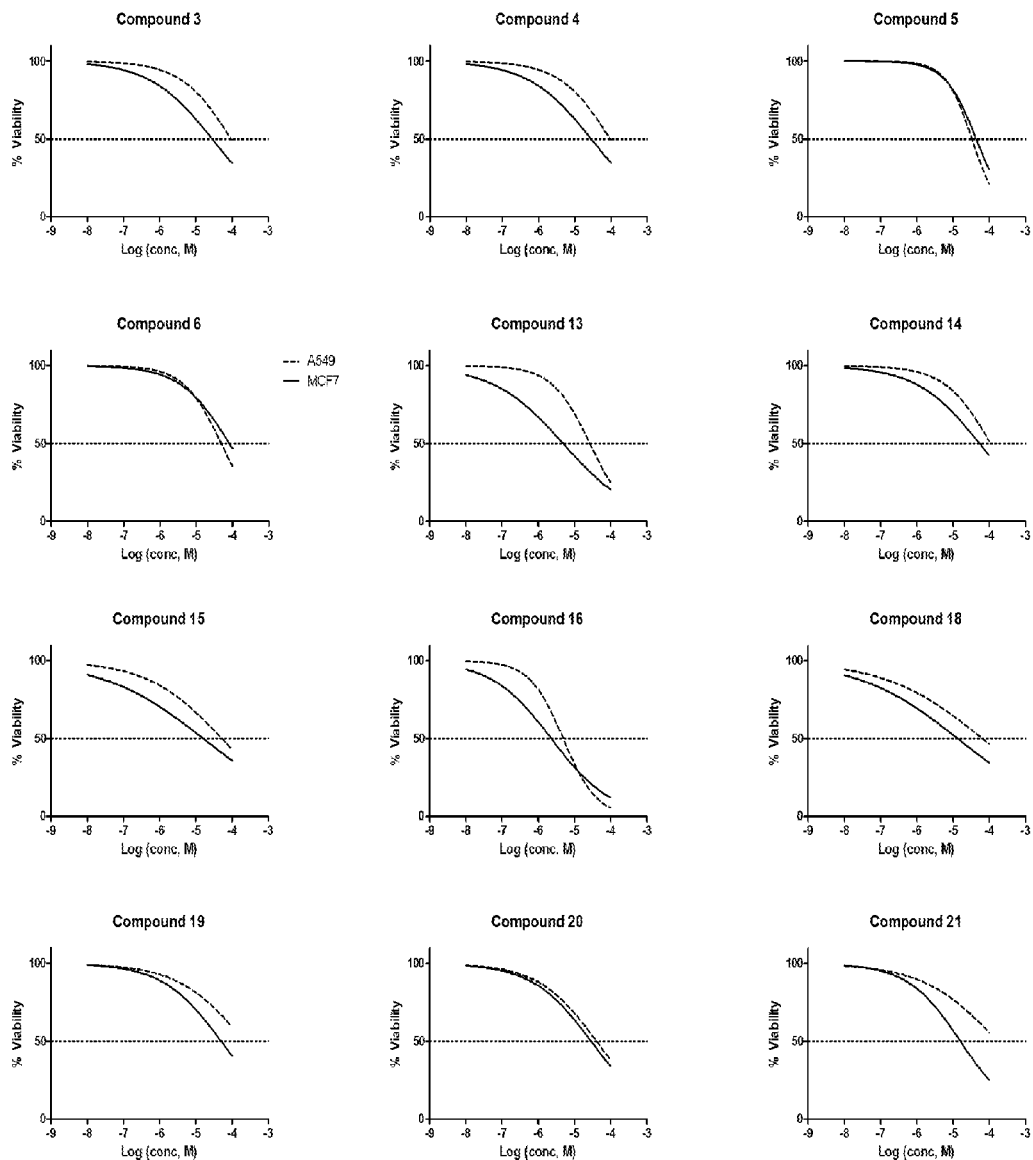

FIG. 2. Non linear fit curves of the growth inhibitory (MTT assay, 48 h treatment) effects of a sample of test compounds against A549 (dashed curve) and MCF7 (solid curve) cell lines.

Figure 3:
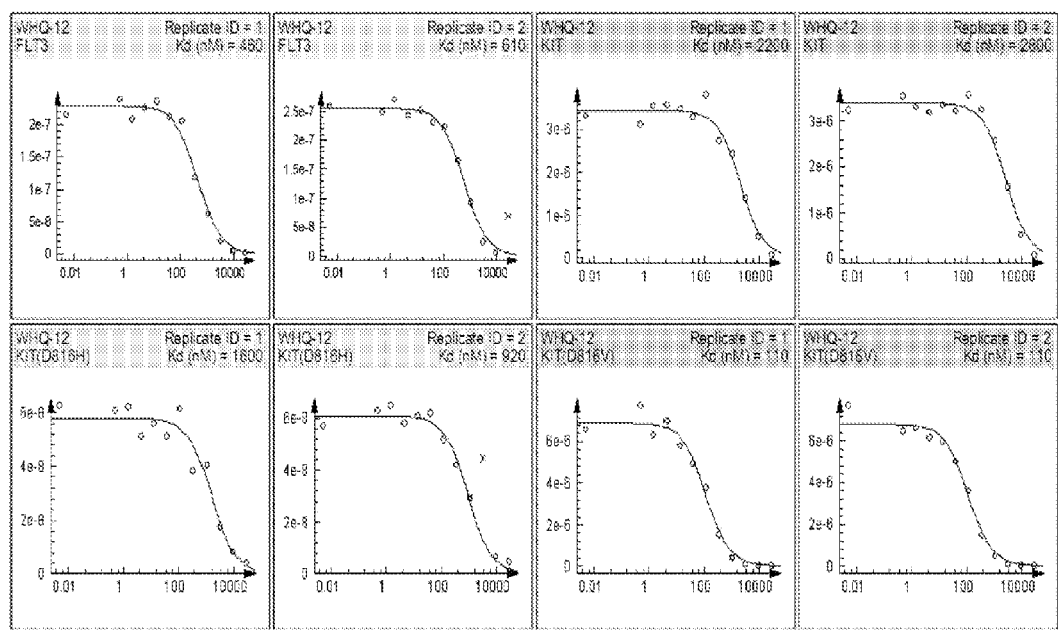

FIG. 3. Dose response curves of compound 4 against four selected PDGFR subfamily kinases obtained using the kinase binding experiment. A non-linear least square fit with the Levenberg-Marquardt algorithm was implemented to fit the curves. WHQ-12 denotes for compound 4. The amount of DNA-tagged kinase detected by qPCR (Signal; y-axis) is plotted versus 4's concentration in nM in log 10 scale (x-axis). Data points marked with an "x" were not used for $K_d$ determination.

Figure 4:
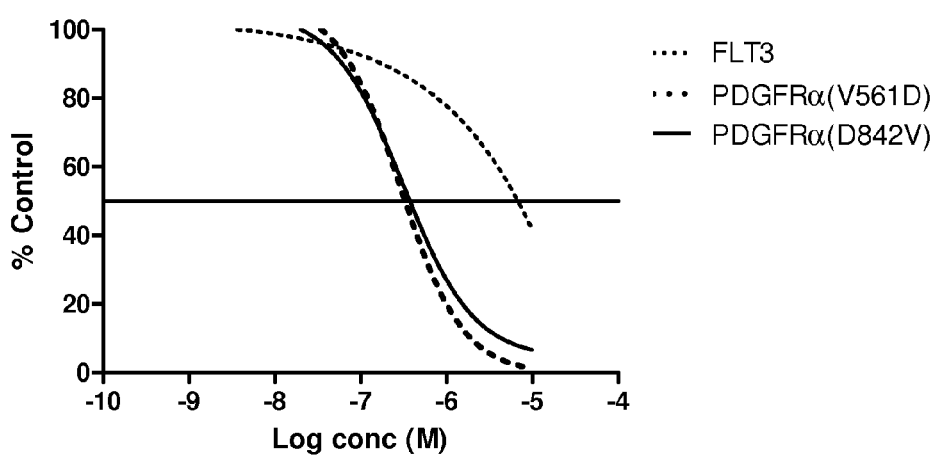

FIG. 4. Dose response curves of compound 4 against 7 selected PDGFR subfamily kinases obtained using the kinase function inhibition screening. The curves were fitted using Nonlinear regression (curve fit) implemented in the GraphPad Prism software (version 5.02). A Sigmoidal dose-response (variable slope) was used in this case.

Figure 5:
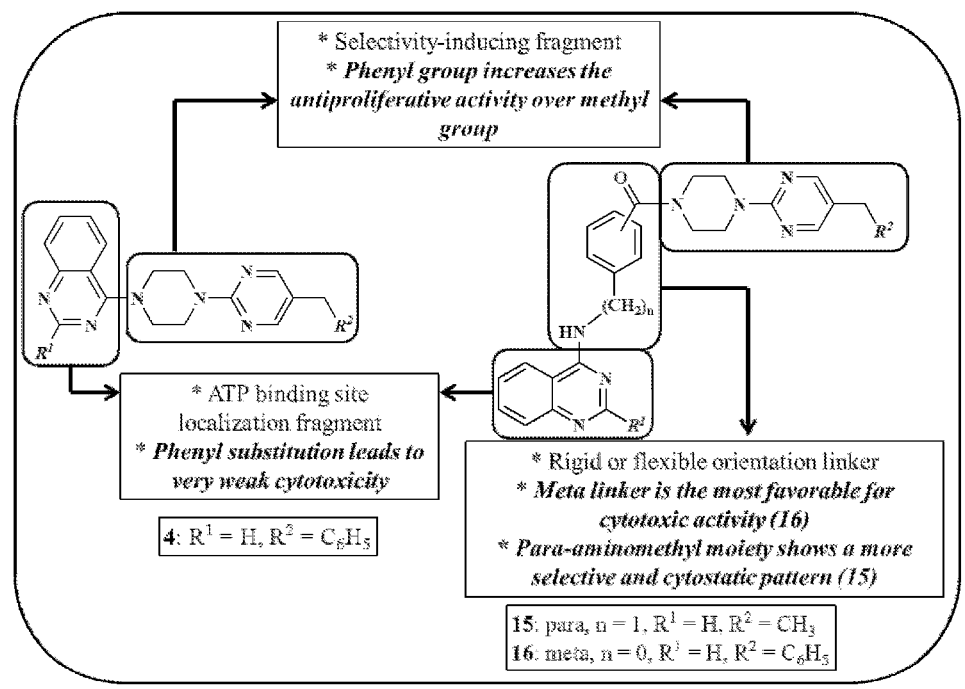

FIG. 5. The overall structure-antiproliferative activity relationships of piperazinylpyrimidines.

Figure 6:
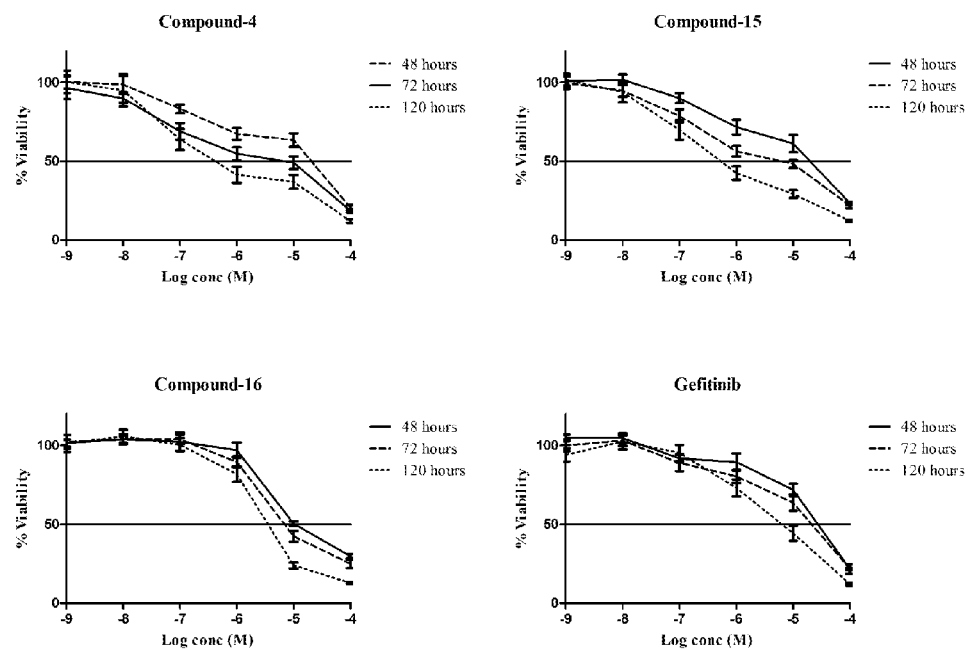
Figure 6:
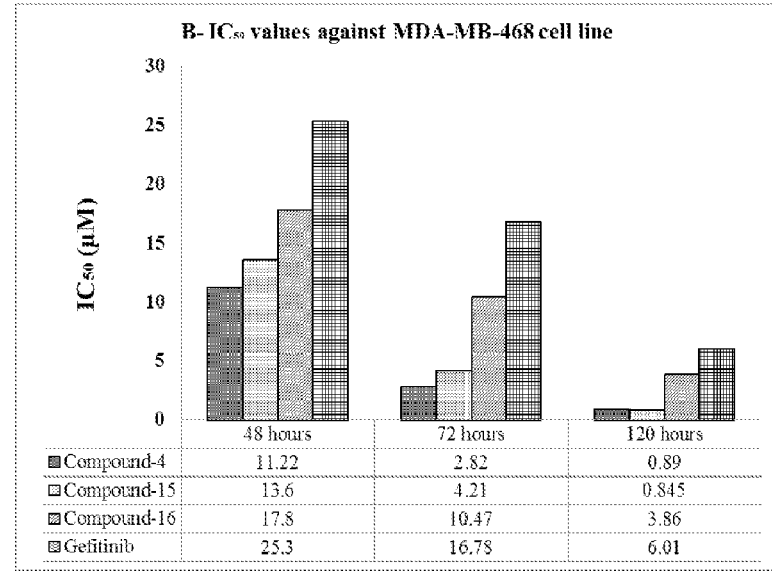

FIG. 6. The results of the MTT assay in which 4, 15, 16, and gefitinib were screened against MDA-MB-468 cell line. (A) Dose-response curves against MDA-MB-468 cell line. The dose response curves plot the % viability against the logarithm of the molar concentration. The error bars represent the 95% confidence interval calculated for 9n (three independent experiments, each is a triplicate). (B) IC50 values against MDA-MB-468 cell line (μM). The IC50 values were calculated using non-linear regression analysis as described in the experimental section.

Figure 7:
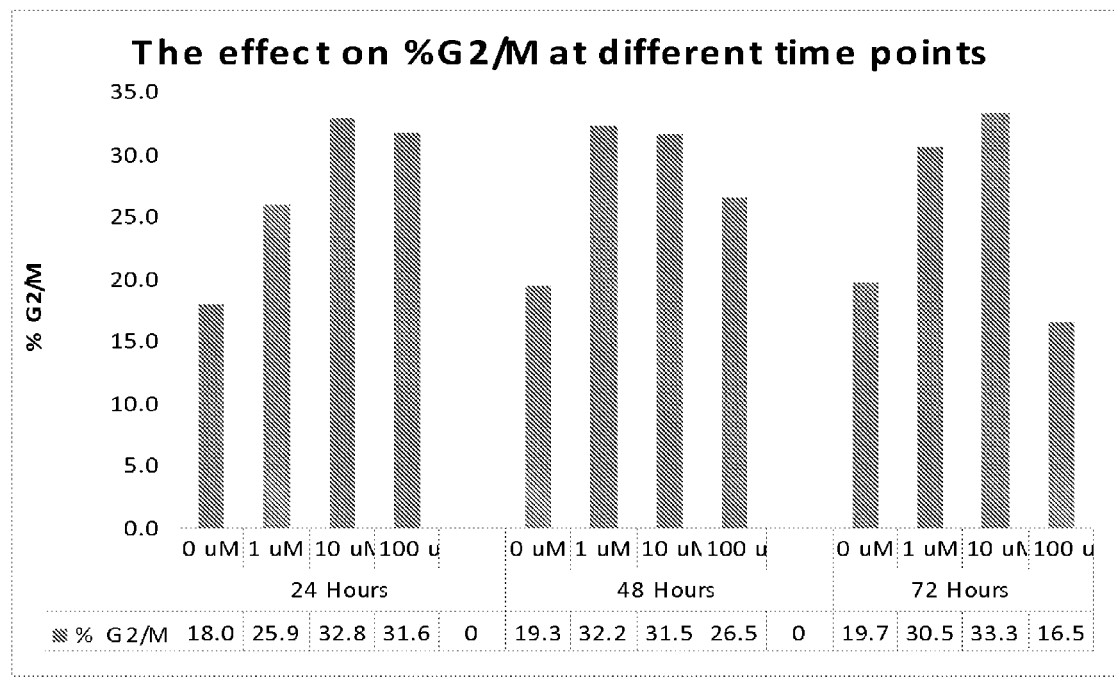

FIG. 7. The percentage of MDA-MB-468 cells in the G2/M stage of cell cycle upon treatment with compound 15 at different concentrations and length of time.

Figure 8:
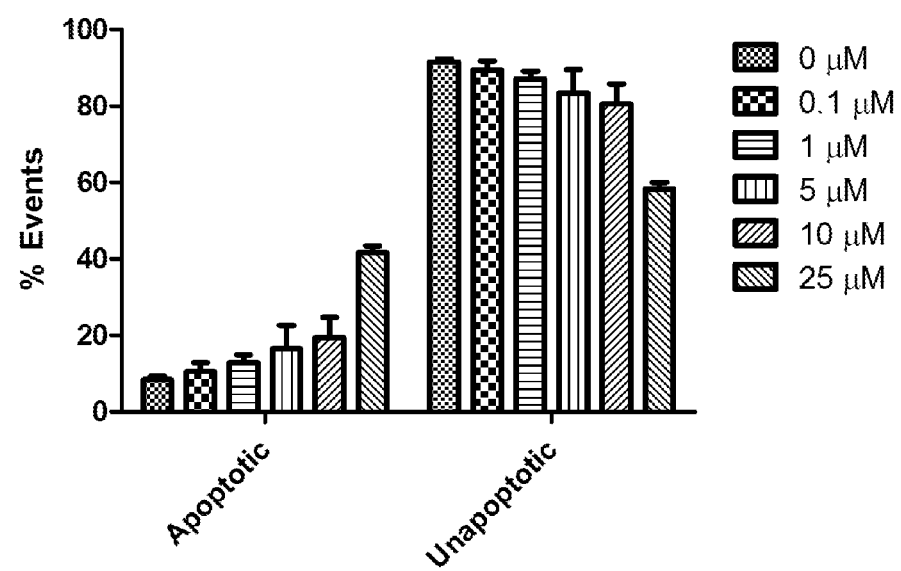

FIG. 8. Annexin V assay results for MDA-MB-468 cells treated with compound 15.

DETAILED DESCRIPTION

The following description sets forth exemplary methods, parameters and the like. It should be recognized, however, that such description is not intended as a limitation on the scope of the present proposed invention but is instead provided as a description of exemplary embodiments.

1. Definitions

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-C10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, NR$_2$, SR, S(O)R, SO$_2$R, SO$_2$NR$_2$, NRSO$_2$R, NRCONR$_2$, NRCOOR, NRCOR, CN, COOR, CONR$_2$, OOCR, COR, CH(OH)R, and NO$_2$, wherein each R is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two R or R' groups on the same or adjacent atoms (e.g., —NR$_2$, or —NR—C(O)R), the two R or R' groups can optionally be taken together with the atoms in the substituent group to which the are attached to form a ring having 5-8 ring members, which can be substituted as allowed for the R or R' itself, and can contain an additional heteroatom (N, O or S) as a ring member.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C3-C8 cycloalkyl, C5-C12 aryl, C1-C8 acyl, and heteroforms of these, each of which can itself be further substituted; other substituents for aryl and heteroaryl moieties include halo, OR, NR$_2$, SR, S(O)R, SO$_2$R, SO$_2$NR$_2$, NRSO$_2$R, NRCONR$_2$, NRCOOR, NRCOR, CN, COOR, CONR$_2$, OOCR, COR, CH(OH)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and each R is optionally substituted as described above for alkyl groups. Where a substituent group contains two R or R' groups on the same or adjacent atoms (e.g., —NR2, or —NR—C(O)R), the two R or R' groups can optionally be taken together with the atoms in the substituent group to which the are attached to form a ring having 5-8 ring members, which can be substituted as allowed for the R or R' itself, and can contain an additional heteroatom (N, O or S) as a ring member. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)₂- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo" as used herein includes fluoro, chloro, bromo and iodo.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

In many compounds within the present invention, isomers including double bond isomers, restricted rotation isomers, optical isomers, and mixtures of these are possible. The invention includes each individual isomer as well as mixtures of various isomeric forms, and specifically includes racemic mixtures as well as individual enantiomers where a single chiral carbon is present. Where multiple chiral carbons are present, each individual diastereomer is included as well as mixtures that comprise a racemic mixture of one or more diastereomer. Many of the compounds herein can exist in different tautomeric forms, and it is understood that each tautomer is included within the scope of the invention as well.

The terms "treat," "treatment" and "therapeutic effect" as used herein refer to reducing or stopping a cell proliferation rate (e.g., slowing or halting tumor growth), reducing the number of proliferating cancer cells (e.g., removing part or all of a tumor), or ameliorating a cell-proliferative disorder in a human or animal subject.

The terms "cell-proliferative disorder," or "proliferative disorder" as used herein refers to a tumor or a cancer in a human or animal subject. In non-limiting embodiments, the cancer is leukemia, non-small cell lung cancer, colon cancer, central nervous system (CNS) cancer, melanoma, ovarian cancer, renal cancer, prostate cancer, or breast cancer.

2. Description of the Invention

The present invention relates to piperzinylpyrimidine compounds having formulas (I), (II), or (III), and pharmaceutically acceptable salts, esters, and prodrugs thereof. The present invention also relates to methods for using the compounds described herein, such as in screening and in treatment and in the preparation of a medicament or pharmaceutical composition for treating conditions described herein. The compounds of the present invention may or may not interact with hinge region and/or ATP-binding groove. Candidate compounds were identified using anticancer cellular assays as a first screen followed by biochemical investigation of those compounds with encouraging cellular activity profiles. Such an order of experiments may aid in identifying cytotoxic or cytostatic lead compounds which may fail to interact with their intended targets and happen to interact with another protein family that was not anticipated. In the current investigation, a systematic attachment of a quinazoline ring, known as a kinase privileged fragment, to a piperazinylpyrimidine scaffold, through linkers that position aforementioned fragments in different relative orientations, has been adopted as a strategy to discover new and selective prototype kinase inhibitors.

The compounds of the present invention having formulas (I), (II), or (III) are reproduced below:

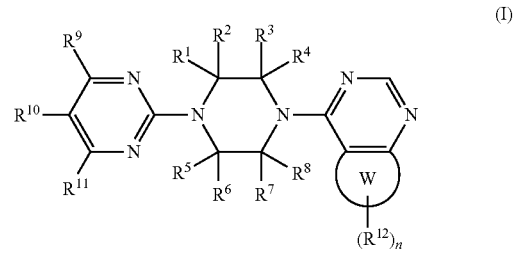

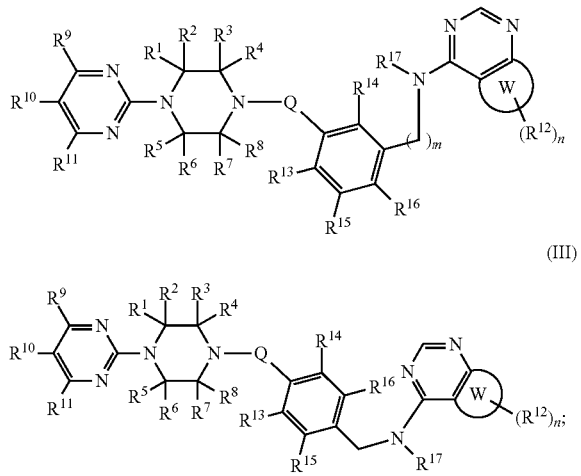

wherein m is 0 or 1;

each n is independently 0-6;

each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;

each Q is $CH_2$, $SO_2$, or C=O;

each $R^1$, $R^2$, $R^3$, $R^4$, $R^5$, $R^6$, $R^7$, and $R^8$ is independently selected from hydrogen, optionally substituted alkyl, or optionally substituted aryl;

each $R^9$, $R^{10}$, $R^{11}$, $R^{12}$, $R^{13}$, $R^{14}$, $R^{15}$ and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted, with the proviso that $R^{10}$ for formula (I) must not be hydrogen; and each $R^{17}$ is independently selected from hydrogen or optionally substituted alkyl;

or a pharmaceutically acceptable salt thereof.

The compounds of the present invention may be chiral. As used herein, a chiral compound is a compound that is different from its mirror image, and has an enantiomer. Furthermore, the compounds may be racemic, or an isolated enantiomer or stereoisomer. Methods of synthesizing chiral compounds and resolving a racemic mixture of enantiomers are well known to those skilled in the art. See, e.g., March, *Advanced Organic Chemistry*, John Wiley and Sons, Inc., New York, (1985).

Compound Synthesis

Synthetic procedures for preparing the compounds of the present invention are illustrated in Schemes 1 and 2 and in the Examples. Other variations in the synthetic procedures known to those with ordinary skill in the art may also be used to prepare the compounds of the present invention. The compounds are then isolated and purified by conventional methods. The compounds also may be made as or converted into salts, and in certain embodiments they are made and used as pharmaceutically acceptable salts such as those described herein.

The piperizinylpyrimidine compounds of the present invention were designed to target the human kinome via linking of a piperazinylprimidine core with a quinazoline group either directly, as in group I, or through an orientation linker, group II, which may offer more rigidity (n=0) or more flexibility (n=1) (FIG. 1). Though not limiting the invention by any theory, the designed derivatives were tailored to potentially localize the hinge region of kinases via their kinase privileged fragment and extend either through the ATP-binding groove or towards the adjacent allosteric site so as to be either type-I or type-II inhibitors, respectively, or perhaps even adopt a novel binding mode. There are two major rationales upon which this design strategy is based: i) because a wide range of conformational ensembles of both active and inactive states exist among the 518 human kinases, certain kinases may be able to accommodate the piperazinylpyrimidine scaffold attached to the quinazoline moiety; and ii) exploiting the steric space of a given class of small molecules with similar chemical features that are positioned differently within the binding site may generate more than one lead kinase inhibitor with different respective kinase selectivity profiles and/or anticancer cellular activity.

The final compounds were mainly derived from two major piperazinylpyrimidine key intermediates (Schemes 1 and 2; Examples 1 and 2). Intermediate 1 was reported in the literature, and the deprotection step was performed using HCl/MeOH method (Betschart, C. et al. US 2005/0054851 A1, 2005). Intermediate 2 was synthesized using palladium catalyzed Suzuki cross coupling followed by deprotection as illustrated in Scheme 2.

Scheme 1

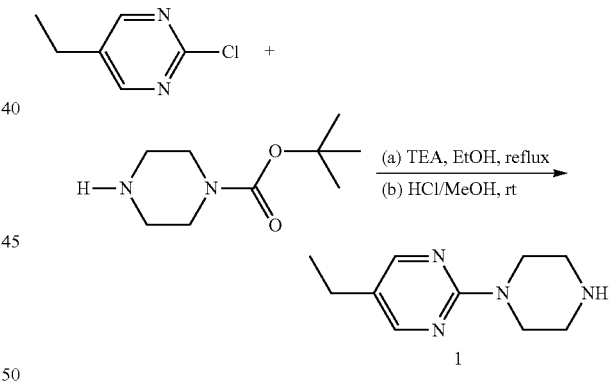

Scheme 2

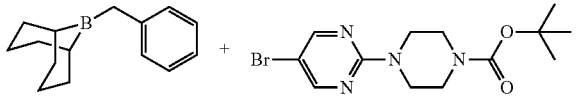

(a) $K_2CO_3$, Pd(PPh$_3$)$_4$, THF/H$_2$O, 100-110° C.
(b) HCl/MeOH, rt

-continued

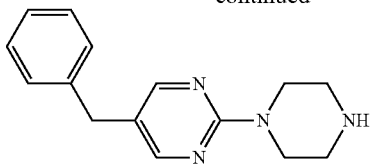

Group I compounds 3-6 (see Examples 3-6) were prepared directly by allowing the respective 4-chloroquinazoline derivative to react with one of the piperazinylpyrimidine intermediates (Scheme 3). Group I compounds represent the direct attachment between the ATP-binding site localizing quinazoline fragment and the selectivity inducing piperazinylpyrimidine scaffold. Intermediates 7-12 (see Examples 7-12) were synthesized by allowing m-aminobenzoic acid, p-aminobenzoic acid; or p-aminomethylbenzoic acid to react with the corresponding quinazoline derivative using similar reaction conditions to those implemented in preparing group I compounds (Scheme 4). Scheme 4 demonstrates the connection of the quinazoline fragment with the different linkers implemented for group II compounds 13-24 (see Examples 13-24). Group II derivatives were prepared via coupling the carboxylic acid group of the intermediates (7-12) with the secondary aliphatic amine functionality of either intermediate 1 or intermediate 2 using EDC/HCl and triethylamine mixture as outlined in Scheme 5. Group II is structurally different from group I via the incorporation of a linker between the two major fragments. Such a linker strategy offers three different options; m-aminophenylcarbonyl and p-aminophenylcarbonyl provide similar rigidity level while orienting the fragments differently whereas p-aminomethylphenylcarbonyl provides more flexibility that allows the compound to cover more conformational space in orienting the major fragments.

Scheme 3

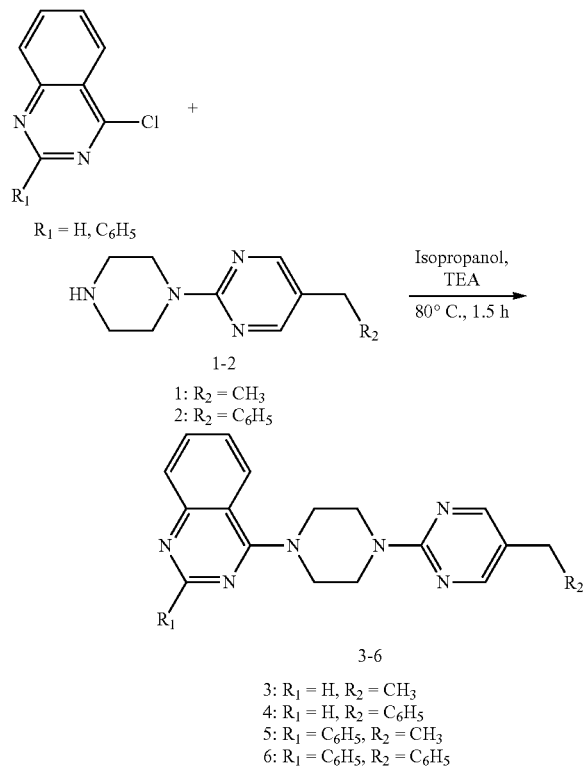

Scheme 4

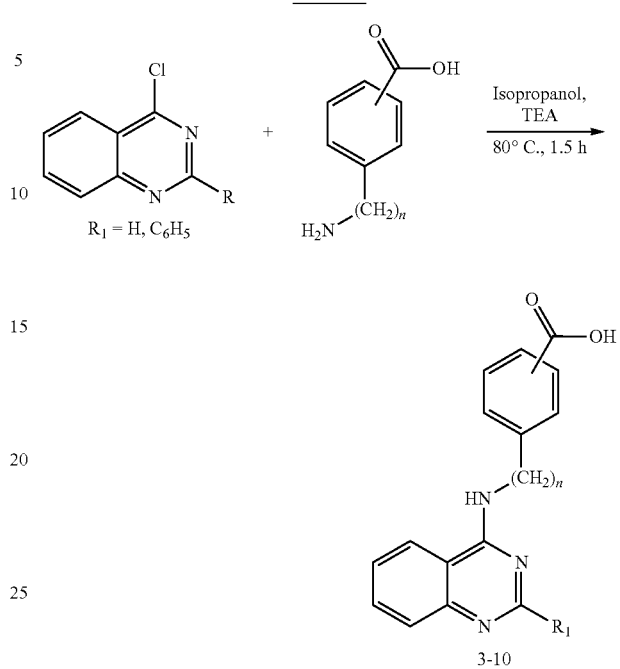

Scheme 5

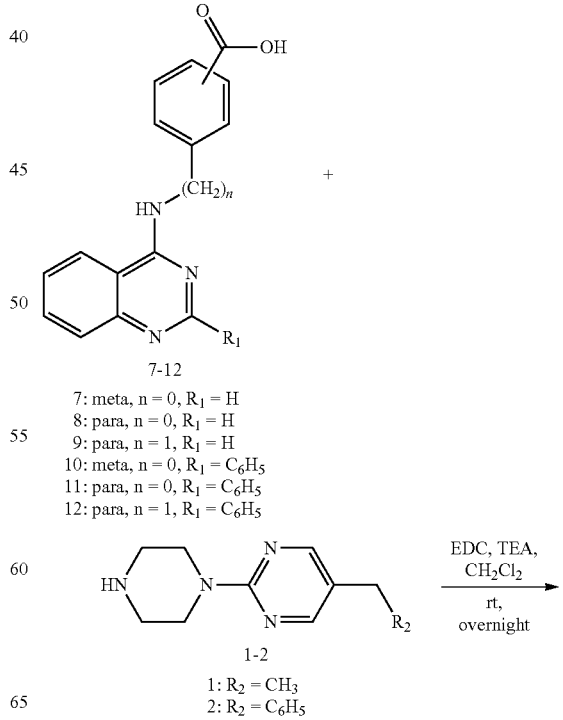

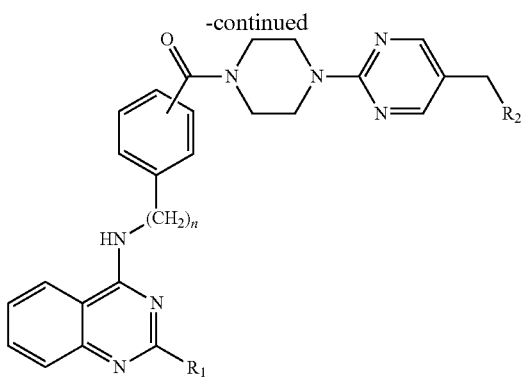

13-24

13: meta, n = 0, $R_1$ = H, $R_2$ = $CH_3$
14: para, n = 0, $R_1$ = H, $R_2$ = $CH_3$
15: para, n = 1, $R_1$ = H, $R_2$ = $CH_3$
16: meta, n = 0, $R_1$ = H, $R_2$ = $C_6H_5$
17: para, n = 0, $R_1$ = H, $R_2$ = $C_6H_5$
18: para, n = 1, $R_1$ = H, $R_2$ = $C_6H_5$
19: meta, n = 0, $R_1$ = $C_6H_5$, $R_2$ = $CH_3$
20: para, n = 0, $R_1$ = $C_6H_5$, $R_2$ = $CH_3$
21: para, n = 1, $R_1$ = $C_6H_5$, $R_2$ = $CH_3$
22: meta, n = 0, $R_1$ = $C_6H_5$, $R_2$ = $C_6H_5$
23: para, n = 0, $R_1$ = $C_6H_5$, $R_2$ = $C_6H_5$
24: para, n = 1, $R_1$ = $C_6H_5$, $R_2$ = $C_6H_5$ The compounds of the present invention may be designed to be more resistant to metabolism compared by incorporating a halo substituent at one or more of the $R^9$, $R^{10}$, $R^{11}$, or $R^{12}$ substituents. For example, compounds 25 and 26 were synthesized according to Examples 25 and 26, below. Each of compounds 25 and 26 incorporate one —Br substituent at the $R^{10}$ position and one —F substituent at one of the $R^{12}$ positions.

Formulation of Compounds

As used herein, the term "pharmaceutically acceptable salts, esters and amides" includes but are not limited to carboxylate salts, amino acid addition salts, esters and amides of the compounds, as well as the zwitterionic forms thereof, which are known to those skilled in the art as suitable for use with humans and animals. (See, e.g., Berge, S. M., et al., "Pharmaceutical Salts," J. Pharm. Sci. (1977) 66:1-19, which is incorporated herein by reference.)

Any suitable formulation of the compounds described herein can be prepared using carriers and excipients that are well known in the art for use in a particular application. For example, compounds may be admixed with a carrier for use in in vitro or in vivo applications. Suitable carriers include partially purified water, such as deionized water or an isotonic solution; buffer systems such as bicarbonate, phosphate, and similar buffers; and mixtures of aqueous solutions with water-miscible organic cosolvents such as acetone or DMSO. Phosphate-buffered saline (PBS), which may be buffered to provide a neutral pH, or in certain embodiments an acidic pH, is sometimes preferred. Stabilizing agents may also be included.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art. For example, pharmaceutically acceptable salts may be obtained by reacting a sufficiently basic compound such as an amine with a suitable acid affording a physiologically acceptable anion. Alkali metal (e.g., sodium, potassium or lithium) or alkaline earth metal (e.g., calcium, magnesium) salts of carboxylic acids and other anionic groups in molecules within the invention also are contemplated.

A compound may be formulated as a pharmaceutical composition and administered to a mammalian host in need of such treatment. For pharmaceutical applications, a compound is typically combined with a pharmaceutically acceptable carrier such as water or other pharmaceutically acceptable excipients. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. Higher concentrations are also appropriate for some solid or semi-solid compositions, and may include amounts up to about 25 wt % or up to about 50 wt % or more. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required.

Methods

The present invention provides a method to identify a molecule that modulates protein kinase activity. The method includes screening a compound described herein, to identify a compound having an effect on the activity of a protein kinase.

The present invention also provides a method to treat a proliferative disorder. The method includes administering to a subject in need of such treatment, an effective amount of a compound of formula (I), (II), or (III):

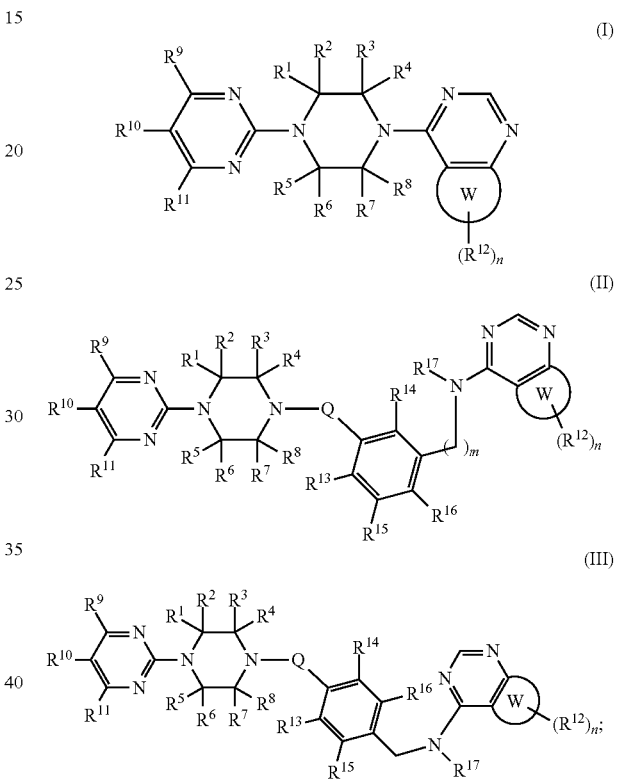

wherein m is 0 or 1;

each n is independently 0-6;

each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;

each Q is $CH_2$, $SO_2$, or C=O;

each $R^1$, $R^2$, $R^3$, $R^4$, $R^5$, $R^6$, $R^7$, and $R^8$ is independently selected from hydrogen, optionally substituted alkyl, or optionally substituted aryl;

each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, $NRCOOR$, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted; and each $R^{17}$ is independently selected from hydrogen or optionally substituted alkyl;

or a pharmaceutically acceptable salt thereof.

The present invention also provides a method to treat a proliferative disorder. In some embodiments, the proliferative disorder is a tumor or a cancer in a human or animal subject. In some preferred embodiments, the cancer may be leukemia, lung cancer, non-small cell lung cancer, hemopoietic cancer, colorectal cancer, colon cancer, skin cancer, central nervous system (CNS) cancer, melanoma, ovarian cancer, renal cancer, prostate cancer, ovarian cancer, or breast cancer. In some preferred embodiments, the cancer may be leukemia, non-small cell lung cancer, colon cancer, central nervous system (CNS) cancer, melanoma, ovarian cancer, renal cancer, prostate cancer, or breast cancer.

The present invention also provides a method to reduce cell proliferation. The cells sometimes are in a cell line, such as a cancer cell line (e.g., breast cancer, prostate cancer, pancreatic cancer, lung cancer, hemopoietic cancer, colorectal cancer, skin cancer, ovarian cancer cell line), for example. In some embodiments, the cancer cell line is a leukemia, non-small cell lung cancer, colon cancer, central nervous system (CNS) cancer, melanoma, ovarian cancer, renal cancer, prostate cancer, or breast cancer cell line. The cells sometimes are in a tissue, can be in a subject, at times are in a tumor, and sometimes are in a tumor in a subject. The method includes administering to a cell in an in vitro or in vivo environment, an effective amount of a compound of formula (I), (II), or (III):

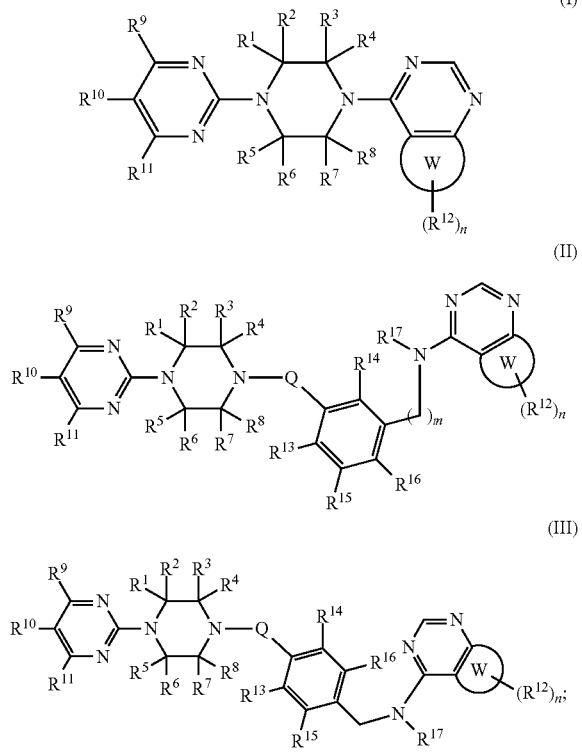

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;

each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;

each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR; S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted; and each $R^{17}$ is independently selected from hydrogen or optionally substituted alkyl;

or a pharmaceutically acceptable salt thereof.

A compound having any one of the above formulas may also be used in methods to induce cell death. The method includes administering to a cell in an in vitro or in vivo environment, an effective amount of a compound of formula (I), (II), or (III):

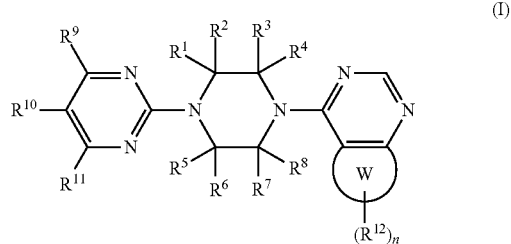

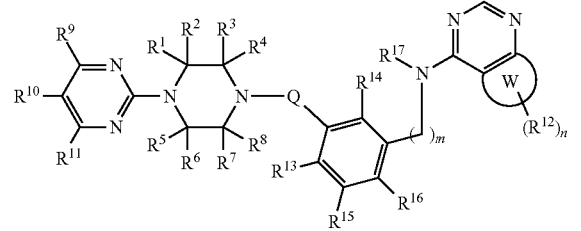

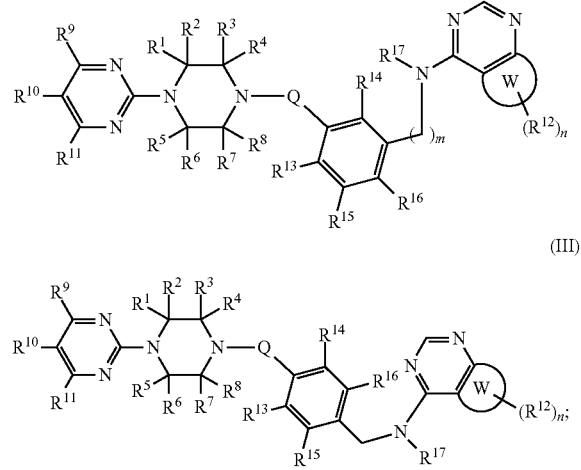

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;

each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;

each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted; and each $R^{17}$ is independently selected from hydrogen or optionally substituted alkyl;

or a pharmaceutically acceptable salt thereof.

The compounds of the present invention may be used for research purposes, as the compounds show overall selectivity towards certain kinase subfamilies. The compounds may be used to identify the efficacy of modulating kinase activity of certain combinations of kinase subfamilies in cells. The present invention also provides a composition comprising an isolated protein kinase complexed with a compound of formula (I), (II), or (III). Such complexes are useful for the information they provide about the binding site of a modulating compound to the particular kinase, and as a research tool for analyzing the structure of the kinase. Such complexes are also useful because they may be more readily crystallized than the uncomplexed kinase, allowing crystallization and crystal structure determination where it would not be possible without the bound modulating compound.

EXAMPLES

The following examples are offered to illustrate but not to limit the invention.

General Chemistry

All temperatures are expressed in ° C. (degrees centigrade). All reagents, solvents, and starting materials were obtained from commercial suppliers and used without further purification. Reactions requiring anhydrous conditions were performed in dry solvents under Argon atmosphere. Reactions were monitored by thin layer chromatography (TLC) on pre-coated silica gel F254 plates (EMD) using a UV detector for visualization. Flash column chromatography was performed with EMD 230-400 mesh silica gel 60 Å. Yields are of purified products. Melting points were determined using Thomas Hoover melting point apparatus and are uncorrected. $^1$H NMR and $^{13}$C NMR spectra were recorded on a Jeol JNM-ECA600 spectrometer. The obtained FID of each experiment was processed using Delta NMR ID processor software. The chemical shifts are expressed in parts per million (ppm) down field from TMS. Spin multiplicities are designated as s (singlet), d (doublet), dd (doublet of doublets), ddd (doublet of doublet of doublets), t (triplet), q (quartet), m (multiplet), and br (broad). Mass spectra (MS) were determined by MALDI instrument. 1 µL test compound solution in acetonitrile is mixed with an equal amount of the matrix solution (saturated 2,5-dihydroxybenzoic acid in 50% ethanol) on the MALDI plate. MALDI spectra were recorded in positive reflectron mode on an AXIMA curved-field reflectron (CFR) MALDI-TOF mass spectrometer using a quadrupole ion-trap (QIT) MALDI-TOF instrument (Kratos/Shimadzu, Columbia, Md., USA). Analytical HPLC was performed using a C18 Phenomenex quantitative 5 µm 4.6 mm×150 mm column with a 30 minute gradient of solvent from 10% to 90% $CH_3CN$ in $H_2O$. Retention time ($R_t$) was recorded in minutes and purity was indicated as percentage of the target compound calculated from % area under the peak (AEP). All final purified compounds showed purity levels greater than 95%.

Example 1

Preparation of 5-ethyl-2-(piperazin-1-yl)pyrimidine (1)

a) A mixture of tert-butyl piperazine-1-carboxylate (6.5 gm, 35.2 mmol), 2-chloro-4-ethylpyrimidine (5 gm, 35.2 mmol), triethylamine (3.55 gm, 35.2 mmol), and absolute ethanol (60 ml) were refluxed for 12 h and then cooled. Ice water was added and the resulting precipitate was filtered, washed with cold water, and finally dried to afford the desired crude intermediate, tert-butyl 4-(5-ethylpyrimidin-2-yl)piperazine-1-carboxylate, as white flakes (9.24 gm, 90% yield); mp: 67-68° C. $^1$H-NMR (DMSO-d6): δ 1.19 (t, J=7.56 Hz, 3H), 1.46 (s, 9H), 2.47 (q, J=7.56 Hz, 2H), 3.49 (t, J=4.8 Hz, 4H), 3.76 (t, J=4.8 Hz, 4H), 8.19 (s, 2H). $^{13}$C-NMR (DMSO-d6): δ 15.59, 22.66, 28.4, 43.76, 43.77, 79.8, 124.95, 154.84, 157.08, 160.05. MS: calcd 292.19 for $C_{15}H_{24}N_4O_2$ $[M]^+$. found, 293.19 $[M+1]^+$. b) HCl/MeOH mixture was prepared by adding 10 ml acetyl chloride dropwise to 100 ml methanol at 0° C. The resulting mixture was warmed to room temperature. The intermediate from step a (9 gm, 30.8 mmol) was then added to the HCl/MeOH and stirred for 12 h at room temperature. Methanol was removed using a row; evaporator. The residue was dissolved in water; the solution was neutralized using solid $NaHCO_3$. The mixture was extracted with $CHCl_3$ (3×200 mL). The combined organic layers was washed successively with saturated $NaHCO_3$, and saturated brine and then dried with anhydrous $Na_2SO_4$. Concentration of the organic layer afforded the desired crude product 1 as a white solid (4.8 gm, 81% yield); mp: 115-116° C. $^1$H-NMR (DMSO-d6): δ 1.20 (t, J=7.56 Hz, 3H), 2.48 (q, J=7.56 Hz, 2H), 3.09 (t, J=5.16 Hz, 4H), 3.94 (t, J=5.16 Hz, 4H), 8.19 (s, 2H). $^{13}$C-NMR (DMSO-d6): δ 15.53, 22.67, 42.76, 44.30, 125.52, 157.15, 160.09.

Example 2

Preparation of 5-benzyl-2-(piperazin-1-yl)pyrimidine (2)

a) A mixture of $K_2CO_3$ (6 gm, 43.5 mmol, 3 equiv) and $Pd(PPh_3)_4$ (1 gm, 0.86 mmol) were stirred at room temperature in 20 mL THF/water (1:1) for 30 minutes. Tert-butyl 4-(5-bromopyrimidin-2-yl)piperazine-1-carboxylate (5 gm, 14.5 mmol, 1 equiv) was then added with B-benzyl-9-BBN (2 equiv, 49 ml of a 0.5 M solution in THF). The resulting mixture was heated with stirring under argon atmosphere in an oil bath adjusted at 100-110° C. until the reaction had reached completion, as monitored by TLC. The reaction mixture was extracted with $CHCl_3$ (3×200 mL). The combined organic layers were then dried with anhydrous $Na_2SO_4$. Chloroform was evaporated under reduced pressure and the residue was purified using flash column chromatography (initially with 4:1 hexane/ethyl acetate and finally with 1:1 hexane/ethyl acetate). Tert-butyl 4-(5-benzylpyrimidin-2-yl)piperazine-1-carboxylate was obtained as a yellow solid (3.8 gm, 74% yield); mp: 121-123° C. $^1$H-NMR (DMSO-d6): δ 1.47 (s, 9H), 3.47 (t, J=4.68 Hz, 4H), 3.75 (t, J=4.68 Hz, 4H), 3.78 (s, 2H), 7.14-7.29 (m, 5H), 8.16 (s, 2H). $^{13}$C-NMR (DMSO-d6): δ 28.4, 35.61, 43.70, 79.92, 122.29, 126.41, 128.51, 128.66, 140.02, 154.84, 157.87, 160.69. MS: calcd 354.21 for $C20H_{26}N_4O_2$ $[M]^+$. found, 355.21 $[M+1]^+$. b) 3.7 gm of the obtained product from step a was then deprotected using HCl/MeOH as described above in the preparation of 1. As a result, compound 2 was obtained as a pale yellow solid (2.2 gm, 80% yield); mp: 108-110° C. $^1$H-NMR (DMSO-d6): δ 1.89 (s, 1H), 2.93 (t, J=4.8 Hz, 4H), 3.76 (t, J=4.8 Hz, 4H), 3.79 (s, 2H), 7.17-7.29 (m, 5H), 8.18 (s, 2H). $^{13}$C-NMR (DMSO-d6): δ 35.59, 44.96, 45.92, 121.79, 126.34, 128.48, 128.6, 140.1, 157.8, 160.5. MS: calcd 254.15 for C15H$_{18}$N$_4$ [M]$^+$. found, 255.15 [M+1]$^+$.

Example 3

Preparation of 4-(4-(5-ethylpyrimidin-2-yl)piperazin-1-yl)quinazoline (3)

A mixture of 1 (72 mg, 0.377 mmol), 4-chloroquinzoline (61 mg, 0.377 mmol), and triethylamine (38 mg, 0.377 mmol) in isopropanol (5 ml) was refluxed at 80° C. for 1.5 hr. The solid separated out of the reaction was filtered, washed with hot solvent and dried to afford compound 3 which was obtained as a yellow solid (61 mg, 50% yield); mp: >250° C. The purity of 3 was confirmed using HPLC (97.27%, R$_t$=9.987). $^1$H-NMR (DMSO-d6): δ 1.13 (t, J=7.56 Hz, 3H), 2.45 (q, J=7.56 Hz, 2H), 3.95 (t, J=5.28 Hz, 4H), 4.16 (t, J=5.28 Hz, 4H), 7.68 (ddd, J=1.38 Hz, J=6.84 Hz, J=8.4 Hz, 1H), 7.96 (m, 2H), 8.22 (d, J=8.4 Hz, 1H), 8.31 (s, 2H), 8.82 (s, 1H). $^{13}$C-NMR (DMSO-d6): δ 15.63, 21.91, 42.85, 48.78, 113.28, 121.66, 125.04, 126.69, 126.88, 134.78, 143.5, 149.89, 157.19, 159.95, 162.51. MS: calcd 320.17 for C18H$_{20}$N$_6$ [M]$^+$. found, 320.39 [M]$^+$.

Example 4

Preparation of 4-(4-(5-benzylpyrimidin-2-yl)piperazin-1-yl)quinazoline (4)

Compound 4 was prepared from 2 (90 mg, 0.354 mmol) and 4-chloroquinzoline (58 mg, 0.354 mmol) following the general procedure for the preparation of 4. The product was a yellow solid (86 mg, 63%); mp: >250° C. The purity of 4 was confirmed using HPLC (97.59%, R$_t$=15.025). $^1$H-NMR (DMSO-d6): δ 3.8 (s, 2H), 3.96 (t, J=5.16 Hz, 4H), 4.26 (t, J=5.16 Hz, 4H), 7.17-7.3 (m, 5H), 7.71 (ddd, J=2.22 Hz, J=6.36 Hz, J=8.4 Hz, 1H), 8.01 (m, 2H), 8.25 (d, J=8.4 Hz, 1H), 8.34 (s, 2H), 8.86 (s, 1H). $^{13}$C-NMR (DMSO-d6): δ 34.51, 42.6, 48.69, 112.49, 119.73, 123.03, 126.11, 126.98, 127.32, 128.32, 128.54, 135.36, 140.86, 140.96, 148.74, 157.84, 159.77, 162.12. MS: calcd 382.19 for C$_{23}$H$_{22}$N$_6$ [M]$^+$. found, 383.35 [M+1]$^+$.

Example 5

Preparation of 4-(4-(5-ethylpyrimidin-2-yl)piperazin-1-yl)-2-phenylquinazoline (5)

Compound 5 was prepared from 1 (72 mg, 0.377 mmol) and 2-phenyl-4-chloroquinzoline (90 mg, 0.377 mmol) following the general procedure for the preparation of 3. The product was a white solid (100 mg, 67%); mp: 137-138° C. The purity of 5 was confirmed using HPLC (96.43%, R$_t$=15.09). $^1$H-NMR (DMSO-d6): δ 1.14 (t, J=7.56 Hz, 3H), 2.44 (q, J=7.56 Hz, 2H), 3.93-3.98 (m, 8H), 7.50-7.54 (m, 4H), 7.83 (ddd, J=1.38 Hz, J=6.84 Hz, J=8.28 Hz, 1H), 7.9 (dd, J=0.96 Hz, J=8.28 Hz, 1H), 8.1 (dd, J=0.96 Hz, J=8.28 Hz, 1H), 8.3 (s, 2H), 8.51 (m, 2H). $^{13}$C-NMR (DMSO-d6): δ 15.6, 21.93, 43.33, 48.85, 114.75, 119.3, 123.55, 125.36, 125.4, 127.96, 128.37, 130.31, 132.9, 138.03, 152.11, 157.13, 158.08, 160.36, 164.12. MS: calcd 396.21 for C$_{24}$H$_{24}$N$_6$ [M]$^+$. found, 397.4 [M+1]$^+$.

Example 6

Preparation of 4-(4-(5-benzylpyrimidin-2-yl)piperazin-1-yl)-2-phenylquinazoline (6)

Compound 6 was prepared from 2 (90 mg, 0.354 mmol) and 2-phenyl-4-chloroquinzoline (84 mg, 0.354 mmol) following the general procedure for the preparation of 3. The product was a white solid (160 mg, 98%); mp: 135-137° C. The purity of 6 was confirmed using HPLC (98.57%, R$_t$=19.707). $^1$H-NMR (DMSO-d6): δ 3.79 (s, 2H), 3.91-3.96 (m, 8H), 7.17-7.30 (m, 5H), 7.49-7.54 (m, 4H), 7.82 (ddd, J=0.78 Hz, J=6.6 Hz, J=7.92 Hz, 1H), 7.9 (d, J=8.28 Hz, 1H), 8.08 (d, J=8.28 Hz, 1H), 8.32 (s, 2H), 8.51 (m, 2H). $^{13}$C-NMR (DMSO-d6): δ 34.56, 43.24, 48.81, 114.74, 122.82, 125.35, 125.4, 126.11, 127.95, 128.35, 128.56, 130.32, 132.89, 138.02, 140.9, 152.11, 157.81, 158.06, 160.26, 164.09. MS: calcd 458.22 for C$_{29}$H$_{26}$N$_6$ [M]$^+$. found, 458.28 [M]$^+$.

Examples 7-12

General Preparation of quinazoline-4-ylaminobenzoic acid and quinazoline-4ylaminomethylbenzoic acid intermediates (7-12)

Either 4-chloroquinzoline or 2-phenyl-4-chloroquinzoline was reacted with an equivalent amount of the corresponding aminobenzoic acid or aminomethylbenzoic acid derivative in the presence of an equivalent amount of triethylamine using anhydrous isopropanol as a solvent. The reaction was performed under 80° C. until the starting materials were consumed. The solid furnished out of the reaction, after solvent evaporation, was washed with hot water to remove triethylamine HCl and used in the next step without further purification or elucidation.

Example 13

Preparation of (4-(5-ethylpyrimidin-2-yl)piperazin-1-yl)(3-(quinazolin-4-ylamino)phenyl)methanone (13)

Intermediate 1 (72 mg, 0.377 mmol) was reacted with intermediate 7 (99 mg, 0.377 mmol) in the presence of equivalent amounts of both EDC.HCl (72 mg, 0.377 mmol) and TEA (38 mg, 0.377 mmol) using 5 ml of CH$_2$Cl$_2$ as a solvent. The reaction mixture was stirred under room temperature overnight. The solvent was evaporated under pressure and the title compound was purified using flash column chromatography (2.5% MeOH in CH$_2$Cl$_2$). The product was a white solid (107 mg, 64%); mp: 146-147° C. The purity of 13 was confirmed using HPLC (97.1%, R$_t$=11.075). $^1$H-NMR (DMSO-d6): δ 1.12 (t, J=7.44 Hz, 3H), 2.43 (q, J=7.44 Hz, 2H), 3.35-3.79 (br, m, 8H), 7.2 (dd, J=1.2 Hz, J=7.74 Hz, 1H), 7.48 (t, J=7.92 Hz, 1H), 7.65 (ddd, J=1.38 Hz, J=7.38 Hz, J=8.28 Hz, 1H), 7.8 (dd, J=1.2 Hz, J=7.38 Hz, 1H), 7.87 (ddd, J=1.38 Hz, J=7.08 Hz, J=8.28 Hz, 1H), 7.98 (ddd, J=0.72 Hz, J=1.8 Hz, J=8.28 Hz, 1H), 8.02 (t, J=1.68 Hz, 1H), 8.27 (s, 2H), 8.57 (dd, J=0.72 Hz, J=7.74 Hz, 1H), 8.63 (s, 1H), 9.93 (s, 1H). $^{13}$C-NMR (DMSO-d6): δ 15.58, 21.9, 41.49, 43.34, 43.87, 46.95, 115.16, 120.82, 122.17, 122.97, 123.18, 125.01, 126.38, 127.85, 128.67, 133.13, 135.88, 139.23, 149.7, 154.36, 157.13, 157.67, 160.24, 169.02. MS: calcd 439.21 for $C_{25}H_{25}N_7O$ [M]$^+$. found, 439.12 [M]$^+$.

Example 14

Preparation of (4-(5-ethylpyrimidin-2-yl)piperazin-1-yl)(4-(quinazolin-4-ylamino)phenyl)methanone (14)

Compound 14 was prepared from intermediate 1 (72 mg, 0.377 mmol) and intermediate 8 (99 mg, 0.377 mmol) following the same procedure utilized in the preparation of 13. The product obtained was a white solid (100 mg, 60%); mp: 248-249° C. The purity of 14 was confirmed using HPLC (95%, $R_t$=10.753). $^1$H-NMR (DMSO-d6): δ 1.12 (t, J=7.56 Hz, 3H), 2.43 (q, J=7.56 Hz, 2H), 3.33-3.84 (br, m, 8H), 7.5 (d, J=8.64 Hz, 2H), 7.66 (ddd, J=1.38, Hz, J=7.2 Hz, J=8.28 Hz, 1H), 7.82 (d, J=8.28 Hz, 1H), 7.88 (ddd, J=1.38 Hz, J=7.2 Hz, J=8.28 Hz, 1H), 8.02 (d, J=8.64 Hz, 2H), 8.27 (s, 2H), 8.59 (d, J=8.46 Hz, 1H), 8.66 (s, 1H), 9.93 (s, 1H). $^{13}$C-NMR (DMSO-d6): δ 15.53, 21.87, 41.55, 43.6, 46.95, 115.19, 121.34, 122.99, 124.92, 126.37, 127.62, 127.78, 127.84, 130.37, 133.12, 140.57, 149.72, 154.2, 157.1, 157.55, 160.2, 169.08. MS: calcd 439.21 for $C_{25}H_{25}N_7O$ [M]$^+$. found, 439.16 [M]$^+$.

Example 15

Preparation of (4-(5-ethylpyrimidin-2-yl)piperazin-1-yl)(4-((quinazolin-4-ylamino)methyl)phenyl)methanone (15)

Compound 15 was prepared from intermediate 1 (77 mg, 0.405 mmol) and intermediate 9 (113 mg, 0.405 mmol) following the general procedure used in the preparation of 13. The product obtained was a white solid (40 mg, 21%); mp: 170-171° C. The purity of 15 was confirmed using HPLC (95.48%, $R_t$=11.288). $^1$H-NMR (DMSO-d6): δ 1.11 (t, J=7.56 Hz, 3H), 2.42 (q, J=7.56 Hz, 2H), 3.34-3.76 (br, m, 8H), 4.84 (d, J=5.82 Hz, 2H), 7.4 (d, J=8.4 Hz, 2H), 7.44 (d, J=8.4 Hz, 2H), 7.54 (ddd, J=1.2 Hz, J=6.72 Hz, J=8.28 Hz, 1H), 7.7 (dd, J=0.84 Hz, J=7.56 Hz, 1H), 7.78 (ddd, J=1.2 Hz, J=6.72 Hz, J=8.28 Hz, 1H), 8.26 (s, 2H), 8.31 (dd, J=0.84 Hz, J=7.56 Hz, 1H), 8.46 (s, 1H), 8.9 (t, J=5.82 Hz, 1H). $^{13}$C-NMR (DMSO-d6): δ 15.58, 21.89, 43.25, 43.75, 46.92, 114.88, 122.63, 124.97, 125.77, 127.09, 127.23, 127.57, 132.67, 134.27, 141.11, 149.17, 155.05, 157.12, 159.37, 160.18, 169.13. MS: calcd 453.23 for $C_{26}H_{27}N_7O$ [M]$^+$. found, 453 [M]$^+$.

Example 16

Preparation of (4-(5-benzylpyrimidin-2-yl)piperazin-1-yl)(3-(quinazolin-4-ylamino)phenyl)methanone (16)

Compound 16 was prepared from intermediate 2 (90 mg, 0.354 mmol) and intermediate 7 (93 mg, 0.354 mmol) following the same procedure utilized in the preparation of 13. The product obtained was a white solid (125 mg, 70%); mp: 120-122° C. The purity of 16 was confirmed using HPLC (97.17%, $R_t$=15.488). $^1$H-NMR (DMSO-d6): δ 3.34-3.78 (br, m, 10H), 7.17-7.29 (m, 6H), 7.48 (t, J=7.92 Hz, 1H), 7.65 (ddd, J=0.96 Hz, J=6.96 Hz, J=8.88 Hz, 1H), 7.8 (d, J=7.56 Hz, 1H), 7.87 (m. 1H), 7.98 (m, 1H), 8.02 (s, 1H), 8.31 (s, 2H), 8.56 (d, J=7.92 Hz, 1H), 8.62 (s, 1H), 9.92 (s, 1H). $^{13}$C-NMR (DMSO-d6): δ 34.53, 41.5, 43.25, 43.78, 46.9, 115.15, 120.82, 122.17, 122.96, 123.18, 126.12, 126.38, 127.86, 128.34, 128.56, 128.67, 133.13, 139.23, 140.87, 149.7, 154.36, 157.67, 157.81, 160.17, 169.02. MS: calcd 501.23 for $C30H_{27}N_7O$ [M]$^+$. found, 501.95 [M]$^+$.

Example 17

Preparation of (4-(5-benzylpyrimidin-2-yl)piperazin-1-yl)(4-(quinazolin-4-ylamino)phenyl)methanone (17)

Compound 17 was prepared from intermediate 2 (90 mg, 0.354 mmol) and intermediate 8 (93 mg, 0.354 mmol) following the procedure used in the preparation of compound 13. The product obtained was a white solid (135 mg, 76%); mp: 245-247° C. The purity of 17 was confirmed using HPLC (96.73%, $R_t$=14.952). $^1$H-NMR (DMSO-d6): δ 3.05-3.8 (br, m, 10H), 7.18-7.31 (m, 5H), 7.5 (d, J=8.64 Hz, 2H), 7.67 (ddd, J=1.38, Hz, J=7.2 Hz, J=8.1 Hz, 1H), 7.82 (d, J=8.28 Hz, 1H), 7.89 (ddd, J=1.2 Hz, J=6.96 Hz, J=8.28 Hz, 1H), 8.04 (d, J=8.64 Hz, 2H), 8.32 (s, 2H), 8.65 (d, J=8.1 Hz, 1H), 8.67 (s, 1H), 10.01 (s, 1H). $^{13}$C-NMR (DMSO-d6): δ 34.50, 43.52, 45.38, 115.20, 121.73, 122.87, 123.11, 126.08, 126.35, 127.75, 127.8, 128.3, 128.51, 130.34, 133.12, 140.59, 140.83, 149.69, 154.27, 157.57, 157.78, 160.13, 169.09. MS: calcd 501.23 for $C30H_{27}N_7O$ [M]$^+$. found, 501.74 [M]

Example 18

Preparation of (4-(5-benzylpyrimidin-2-yl)piperazin-1-yl)(4-((quinazolin-4-ylamino)methyl)phenyl)methanone (18)

Compound 18 was prepared from intermediate 2 (102 mg, 0.405 mmol) and intermediate 9 (113 mg, 0.405 mmol) following the general procedure used in the preparation of 13. The product obtained was a white solid (40 mg, 19%); mp: 99-101° C. The purity of 18 was confirmed using HPLC (96.14%, $R_t$=15.95). $^1$H-NMR (DMSO-d6): δ 3.37-3.83 (br, m, 10H), 4.89 (d, J=5.82 Hz, 2H), 7.22-7.34 (m, 5H), 7.43 (d, J=8.28 Hz, 2H), 7.49 (d, J=8.28 Hz, 2H), 7.6 (ddd, J=1.2 Hz, J=6.72 Hz, J=8.28 Hz, 1H), 7.76 (dd, J=0.84 Hz, J=7.56 Hz, 1H), 7.84 (ddd, J=1.2 Hz, J=6.72 Hz, J=8.28 Hz, 1H), 8.34 (s, 2H), 8.36 (d, J=7.92 Hz, 1H), 8.51 (s, 1H), 8.94 (t, J=5.82 Hz, 1H). $^{13}$C-NMR (DMSO-d6): δ 34.49, 43.23, 114.86, 122.61, 122.89, 125.74, 126.09, 127.07, 127.2, 127.54, 128.31, 128.53, 132.62, 134.23, 140.83, 141.09, 149.17, 155.02, 157.77, 159.36, 160.1, 169.1. MS: calcd 515.24 for $C31H_{29}N_7O$ [M]$^+$. found, 515 [M]$^+$.

Example 19

Preparation of (4-(5-ethylpyrimidin-2-yl)piperazin-1-yl)(2-(3-phenylquinazolin-4-ylamino)phenyl)methanone (19)

Compound 19 was prepared from intermediate 1 (120 mg, 0.625 mmol) and intermediate 10 (213 mg, 0.625 mmol) following the same procedure utilized in the preparation of 13. The product obtained was a white solid (210 mg, 40%); mp: 204-205° C. The purity of 19 was confirmed using HPLC (97.67%, $R_t$=15.123). $^1$H-NMR (DMSO-d6): δ 1.09 (t, 3H), 2.4 (q, 2H), 3.16-3.71 (m, 8H), 7.18 (d, J=7.56 Hz, 1H), 7.41-7.59 (m, 5H), 7.83 (m, 2H), 8.02 (m, 1H), 8.13 (m, 1H), 8.21 (s, 2H), 8.4 (m, 2H), 8.54 (d, J=8.22 Hz, 1H), 9.87 (s, 1H). $^{13}$C-NMR (DMSO-d6): δ 15.36, 21.85, 42.66, 44.25, 114.01, 120.67, 121.79, 122.86, 125.02, 125.97, 127.9, 128.16, 128.27, 128.6, 130.12, 130.2, 133.23, 136.23, 138.3, 139.59, 150.56, 157.03, 157.92, 159.02, 160.3, 169.2. MS: calcd 515.24 for C31H$_{29}$N$_7$O [M]$^+$. found, 515.84 [M]$^+$.

Example 20

Preparation of (4-(5-ethylpyrimidin-2-yl)piperazin-1-yl)(2-(4-phenylquinazolin-4-ylamino)phenyl)methanone (20)

Compound 20 was prepared from intermediate 1 (120 mg, 0.625 mmol) and intermediate 11 (213 mg, 0.625 mmol) following the same procedure utilized in the preparation of 13. The product obtained was a white solid (180 mg, 34%); mp: >250° C. The purity of 20 was confirmed using HPLC (96.02%, R$_f$=14.823). $^1$H-NMR (DMSO-d6): δ 1.12 (t, 3H), 2.43 (q, 2H), 3.32-3.78 (m, 8H), 7.51-7.65 (m, 6H), 7.89 (m, 2H), 8.12 (m, 2H), 8.27 (s, 2H), 8.47 (m, 2H), 8.6 (d, J=8.28 Hz, 1H), 10.0 (s, 1H). $^{13}$C-NMR (DMSO-d6): δ 15.54, 21.88, 43.59, 114.04, 121.22, 123.07, 124.92, 126.07, 127.91, 128.17, 128.47, 130.28, 130.33, 133.36, 138.16, 140.74, 150.53, 157.1, 157.77, 158.94, 160.22, 169.11. MS: calcd 515.24 for C31H$_{29}$N$_7$O [M]$^+$. found, 515.89 [M]$^+$.

Example 21

Preparation of (4-(5-ethylpyrimidin-2-yl)piperazin-1-yl)(4-((2-phenylquinazolin-4ylamino)methyl)phenyl)methanone (21)

Compound 21 was prepared from intermediate 1 (120 mg, 0.625 mmol) and intermediate 12 (221 mg, 0.625 mmol) following the same procedure utilized in the preparation of 13. The product obtained was a white solid (105 mg, 20%); mp: 207-208° C. The purity of 21 was confirmed using HPLC (97.08%, R$_f$=15.735). $^1$H-NMR (DMSO-d6): δ 1.1 (t, 3H), 2.41 (q, 2H), 3.34-3.76 (m, 8H), 4.97 (d, J=5.82 Hz, 2H), 7.4-7.55 (m, 8H), 7.79 (m, 2H), 8.25 (s, 2H), 8.33 (m, 1H), 8.43 (m, 2H), 8.98 (t, J=5.82 Hz, 1H). $^{13}$C-NMR (DMSO-d6): δ 15.56, 21.88, 41.4, 43.26, 43.56, 46.85, 113.79, 122.68, 124.94, 125.45, 127.24, 127.31, 127.84, 128.2, 130.3, 132.83, 134.26, 138.52, 141.51, 149.98, 157.1, 159.15, 159.59, 160.16, 169.11. MS: calcd 529.26 for C32H$_{31}$N$_7$O [M]$^+$. found, 529.88 [M]$^+$.

Example 22

Preparation of (4-(5-benzylpyrimidin-2-yl)piperazin-1-yl)(3-(2-phenylquinazolin-4ylamino)phenyl)methanone (22)

Compound 22 was prepared from intermediate 2 (120 mg, 0.472 mmol) and intermediate 10 (160 mg, 0.472 mmol) following the same procedure utilized in the preparation of 13. The product obtained was a white solid (135 mg, 23%); mp: 214-215° C. The purity of 22 was confirmed using HPLC (95.38%, R$_f$=18.948). $^1$H-NMR (DMSO-d6): δ 3.37-3.83 (br, m, 10H), 7.2-7.32 (m, 6H), 7.44-7.67 (m, 5H), 7.91 (m, 2H), 8.1 (ddd, J=0.9 Hz, J=2.1 Hz, J=8.28 Hz, 1H), 8.2 (m, 1H), 8.32 (s, 2H), 8.47 (m, 2H), 8.62 (d, J=8.28 Hz, 1H), 10.0 (s, 1H). $^{13}$C-NMR (DMSO-d6): δ 34.53, 41.46, 43.84, 46.95, 113.99, 120.65, 121.84, 122.89, 122.98, 123.02, 126.07, 126.11, 127.88, 128.17, 128.33, 128.54, 128.66, 128.78, 130.3, 131.43, 132.01, 133.34, 136.11, 138.18, 139.54, 140.85, 150.49, 157.77, 157.85, 158.92, 160.15, 169.14. MS: calcd 577.26 for C36H$_{31}$N$_7$O [M]$^+$. found, 577.55 [M]$^+$.

Example 23

Preparation of (4-(5-benzylpyrimidin-2-yl)piperazin-1-yl)(4-(2-phenylquinazolin-4ylamino)phenyl)methanone (23)

Compound 23 was prepared from intermediate 2 (120 mg, 0.472 mmol) and intermediate 11 (160 mg, 0.472 mmol) following the same procedure utilized in the preparation of 13. The product obtained was a white solid (70 mg, 12%); mp: >250° C. The purity of 23 was confirmed using HPLC (95%, R$_f$=18.98). $^1$H-NMR (DMSO-d6): δ 3.38-3.82 (br, m, 10H), 7.21-7.33 (m, 6H), 7.53-7.69 (m, 5H), 7.93 (m, 2H), 8.15 (m, 2H), 8.34 (s, 2H), 8.51 (m, 2H), 8.64 (d, J=8.28 Hz, 1H), 10.06 (s, 1H). $^{13}$C-NMR (DMSO-d6): δ 34.56, 43.53, 114.08, 121.28, 122.95, 123.11, 126.16, 127.98, 128.21, 128.38, 128.54, 128.6, 128.75, 130.29, 130.42, 131.47, 133.44, 138.19, 140.8, 140.89, 150.57, 157.83, 159, 160.18, 169.19. MS: calcd 577.26 for C$_{36}$H$_{31}$N$_7$O [M]$^+$. found, 577.69 [M]$^+$.

Example 24

Preparation of (4-(5-benzylpyrimidin-2-yl)piperazin-1-yl)(4-((2-phenylquinazolin-4-ylamino)methyl)phenyl)methanone (24)

Compound 24 was prepared from intermediate 2 (120 mg, 0.472 mmol) and intermediate 12 (167 mg, 0.472 mmol) following the same procedure utilized in the preparation of 13. The product obtained was a white solid (59 mg, 10%); mp: 216-217° C. The purity of 24 was confirmed using HPLC (97.27%, R$_1$=19.543). $^1$H-NMR (DMSO-d6): δ 3.37-3.79 (br, m, 10H), 4.99 (d, J=5.82 Hz, 2H), 7.19-7.31 (m, 5H), 7.42-7.66 (m, 8H), 7.82 (m, 2H), 8.3 (s, 2H), 8.35 (d, J=8.22 Hz, 1H), 8.44-8.47 (m, 2H), 9.02 (t, J=5.82 Hz, 1H). $^{13}$C-NMR (DMSO-d6): δ 34.51, 43.24, 43.56, 113.79, 122.68, 122.88, 125.45, 126.1, 127.23, 127.3, 127.84, 128.2, 128.31, 128.53, 130.04, 132.83, 134.24, 138.52, 140.83, 141.51, 149.98, 157.77, 159.15, 159.58, 160.09, 169.12. MS: calcd 591.27 for C$_{37}$H$_{33}$N$_7$O [M]$^+$. found, 591.69 [M]$^+$.

Example 25

Preparation of 4-(4-(5-bromopyrimidin-2-yl)piperazin-1-yl)-6-fluoroquinazoline (25)

A mixture of 5-bromo-2-(piperazin-1-yl)pyrimidine (240 mg, 1.0 mmol), 4-chloro-6-fluoroquinzoline (180 mg, 1.0 mmol), and diisopropylethylamine (190 mg, 1.5 mmol) in isopropanol (10 ml) was refluxed at 80° C. for 1.5 hr. The solid separated out of the reaction upon cooling and was filtered, washed with hot solvent and dried to afford compound 25 which was obtained as fine white crystals (317 mg, 81% yield). $^1$H-NMR (DMSO-d6): δ 3.8 (m, 4H), 3.9 (m, 4H), 7.75 (m, 2H), 7.88 (dd, 1H), 8.48 (s, 2H), 8.62 (s, 1H). $^{13}$C-NMR (DMSO-d6): δ 43.7, 49.0, 106.25, 109.95, 110.15, 116.9, 117.0, 122.95, 123.15, 148.95, 153.75, 158.2, 158.5, 159.85, 159.95, 163.95.

Example 26

Preparation of (4-(5-bromopyrimidin-2-yl)piperazin-1-yl)(4-((6-fluoroquinazolin-4-ylamino)methyl)phenyl)methanone (26)

Compound 26 was prepared from 4-chloro-6-fluoroquinzoline (11 mg, 0.06 mmol), following the same procedure utilized in the preparation of 13. The product 26 obtained was a pale yellow solid (19 mg, 60%). $^1$H-NMR (DMSO-d6): δ 3.33-3.84 (br, m, 8H), 4.84 (d, J=6.6 Hz, 2H), 7.37 (d, J=9 Hz, 2H), 7.41 (d, J=9 Hz, 2H), 7.68 (ddd, J=3 Hz, J=8.4 Hz, J=9 Hz, 1H), 7.76 (dd, J=6.6 Hz, J=9 Hz, 1H), 8.14 (dd, J=3.6 Hz, J=9 Hz, 1H), 8.34 (s, 1H), 8.35 (s, 1H), 8.43 (s, 1H), 8.81 (t, J=6 Hz, 1H).

Biological Methods

Growth Inhibition of NCI-60 Tumor Cell Lines

The NCI-DTP uses the SRB (sulforhodamine B) assay to measure the ability of a test compound to inhibit the growth of a given cell line. The cell lines used in the NCI-60 are maintained using RPMI 1640 medium supplemented with 5% fetal bovine serum and 2 mM L-glutamine. Cell lines are seeded into a series of 96-well microtiter plates, with varied inoculation densities, depending on the growth rate and doubling time of each cell line. The plates are then incubated at 37° C., 5% $CO_2$, 95% air and 100% relative humidity for 24 hours before treating with the test compounds. On the treatment day, experimental agents are added to the cells with a series of target final concentrations: 100, 10, 1, 0.1, and 0.01 µM. After 48 hours treatment while being incubated under the above conditions, the cells are fixed with trichloroacetic acid (concentration differs according to the nature of the cell line; adherent or suspension) for one hour at 4° C. After removal of the supernatant, the plates are washed with water several times and dried completely in the air. Then 100 µL of 0.4% sulforhodamine B (SRB) solution in 1% acetic acid is added for 10 minutes. The unbound dye is removed and the plates are washed with 1% acetic acid. The bound dye is then solubilized with 10 mM trizma base, and the absorbance is measured using a plate reader at 515 nm. The same treatment and measurement were performed for cells prior to treatment and were assigned TZ (T-zero). The % growth was calculated using the following equation:

$$\% \text{ growth} = \frac{(T_i - T_z) \times 100}{(C - T_z)},$$

where Ti is the reading for the treated well after two days of the treatment with a certain concentration of a specific compound. C is the average reading measured in the untreated wells after two days of treatment with the vehicle. TZ is the average reading measured prior to treatment. GI50 is the dose that causes 50% inhibition of the growth after the treatment time compared to the TZ and calculated from $$\% \text{ growth} = 50 = \frac{(T_i - T_z) \times 100}{(C - T_z)}.$$

TGI is the dose that causes a total inhibition of the growth and can be computed using the equation: Ti=TZ. LC50 is the dose that kills 50% of the cells compared to the cell density at the treatment time and calculated from $$-50 = \frac{(T_i - T_z) \times 100}{T_z}.$$

MTT Viability Assay

MDA-MB-468 human breast cells were obtained from ATCC and cultured in RPMI 1640 medium (ATCC) supplemented with 10% FBS (Invitrogen), and 2% antibiotic-antimycotic mixture of Penicillin-G, Streptomycin sulfate, and Amphotericin B (Invitrogen) in a 5% $CO_2$-95% humidity incubator at 37° C. 3-[4,5-dimethylthiazol-2-yl]-2,5-diphenyltetrazoliumbromide (MTT) assay was chosen to determine the IC50 (the concentration required to inhibit survival by 50%) of the test compounds (4, 15, and 16) against the MDA-MB-468 cell line using gefitinib as a positive control. 5000 cells, in 100 uL of the culture medium, were plated per well in 96-well plates. Cells were allowed to adhere for 1 day. Cells were then treated with fresh culture medium containing one of several concentrations of the test compounds; 100, 10, 1, 0.1, 0.01, 0.001 µM. The plates were processed after 48, 72, or 120 hours via discarding the media and adding 100 uL 0.5 mg/ml MTT reagent in fresh culture media. The plates were then incubated for 4 hours under 10% CO2 at 37° C. The media was then removed and 100 uL of DMSO was added to each well to dissolve the formed formazone crystals. Plates were kept at room temperature over night away from light. The optical density of the formed violet color was quantified using an automatic spectrophotometer (Tristar LB 941) at a wavelength of 562 nm. The experiment was carried out with triplicate for each concentration of a given compound. Three independent experiments were conducted at three different dates. The concentration required for 50% reduction in the optical density, and hence the viability compared to control vehicle treated wells, was estimated for each compound against the studied cell line by non-linear regression analysis of the Log 10 concentration in moles versus % viability curves. Curve fitting was performed using the variable slope-four parameter module implemented in the GraphPad Prism software (version 5.02).

Kinase Binding Screening

Biotinylated kinase ligand was immobilized onto streptavidin coated magnetic beads and washed with blocking buffer. The liganded beads were then incubated with DNA-tagged kinase in the presence of test compound for 1 h at room temperature. Binding reactions were carried out in 20% Seablock, 0.17×PBS, 0.005% Tween 20, 6 mM DTT, in a final volume of 0.04 mL. Beads were then washed with wash buffer (PBS, 0.05% Tween 20), and then incubated with elution buffer (PBS, 0.05% Tween 20, 0.5 M non-biotinylated kinase ligand) and eluted. The kinase concentration in the eluate was then measured by quantitative PCR. The detected signal is proportional to the number of eluted DNA-tagged kinase molecules and hence to the binding potency of a given test compound. The results of this single dose screening are reported in the form of binding percentage of control (B-POC) which is defined as follows:

$$B\text{-}POC = \frac{[(\text{test compound signal} - \text{positive control signal}) \times 100]}{(\text{negative control signal} - \text{positive control signal})}.$$

The negative control signal is obtained by the vehicle and corresponds to B-POC=100%. The positive signal control is detected by a binding positive compound and is B-POC 0%. The B-POC results are the average of duplicate measurements. Only interactions with B-POC=35 were considered significant and thus used for calculating the selectivity scores (Table 1) of the test compounds as follows:

$$S(35) = \frac{\text{number of kinases showed } B\text{-}POC \leq 35}{\text{total number of wild} - \text{type kinases}(198)}$$

In order to determine the Kd, the above procedure is followed at 11-point three fold serial dilution of the test compound, from 30 µM to 0.508 nM, with the result of a standard dose-response curve. The Kd is then calculated according to the following equation:

$$\text{response} = \text{background} + \frac{\text{signal} - \text{background}}{1 + K_d^{hill\ slope} + \text{dose}^{hill\ slope}},$$

hill slope=−1. A non-linear least square fit with the Levenberg-Marquardt algorithm was implemented to fit the curves (FIG. 3). Kinase binding assays were performed by Ambit Bioscience (San Diego, Calif., USA).

The results of kinase binding assay are shown in Table 1, which includes the B-POC values of 10 μM of compounds 4, 15, and 16 against the most sensitive kinases tested within this binding experiment. Kinases are ranked according to their sensitivity towards binding by each compound separately from the most (lower B-POC) to the least (higher B-POC) sensitive. Kinases within the same subfamily are highlighted. Selectivity scores (S35) of the test compounds against a total of 198 wild-type non-mutant kinases. $K_d$ values of 4 against selected PDGFR subfamily members are in parentheses and expressed in μM. Both the B-POC and $K_d$ values are the average of duplicate measurements.

In Vitro Cellular Screening

Compounds 3-6 and 13-24 were screened in-house against A549 (NSCLC) and MCF7 (breast cancer) cell lines to test the target compounds' cytotoxic potential and to reduce the number of compounds to be further investigated (data not shown). The structures of the active compounds were submitted for screening against the NCI-60 cell lines panel. Compounds (3-4, 13, 15-16, and 19-23) were initially accepted for screening against the NCI-60 at a single concentration of 10 μM. Eight out of the above compounds (3-4, 13, 15-16, and 19-21) showed significant antiproliferative activity at a 10 μM dose and were accordingly evaluated at five concentrations in order to determine their dose-response behavior and calculate their GI50 (dose inhibiting 50% of the growth compared to the control), TGI (dose inhibiting the growth completely), and LC50 (dose killing 50% of the starting cell population) values. Table 2 shows the GI50, TGI, and LC50 values for compounds 4, 15, and 16. Three compounds (3-4 and 15) showed an interesting pattern of cytotoxic activity and were submitted for retesting in order to confirm the reproducibility

TABLE 1

| | | B-POC ($K_d$) | | | |
|---|---|---|---|---|---|
| Kinase | 4 | Kinase | 15 | Kinase | 16 |
| CDK11 | 0 | ABL1(F317L)-phosphorylated | 6.8 | RIPK1 | 19 |
| KIT(D816V) | 0.5 (0.11) | BRAF(V600E) | 13 | ABL1(F317L)-phosphorylated | 20 |
| CDK8 | 3.4 | CSNK1G2 | 18 | | 22 |
| RIPK1 | 3.5 | CSNK1D | 23 | | 23 |
| FLT3(K663Q) | 4 | CSNK1G3 | 24 | p38 gamma | 25 |
| PDGFRB | 4.1 | CSNK1E | 29 | CSNK1D | 28 |
| KIT(V559D) | 4.3 | BRAF | 34 | CSNK1E | 43 |
| FLT3 | 8.4 (0.53) | CSNK1A1 | 36 | | |
| KIT | 9.1 (2.5) | CDK11 | 47 | | |
| KIT(L576P) | 9.8 | | | | |
| PDGFRA | 21 | | | | |
| CSNK1D | 26 | | | | |
| ABL1(F317I)-phosphorylated | 30 | | | | |
| KIT(D816H) | 30 (1.3) | | | | |
| CSF1R | 31 | | | | |
| CSNK1E | 45 | | | | |
| FLT3(D835H) | 46 | | | | |
| DDR1 | 47 | | | | |
| FLT3(ITD) | 49 | | | | |
| Number of kinases with B-POC ≤ 35 | 15 | | 7 | | 6 |
| S(35) | 0.075 | | 0.035 | | 0.03 |

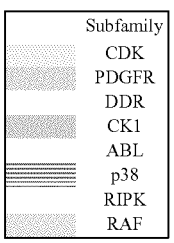

| Subfamily |
|---|
| CDK |
| PDGFR |
| DDR |
| CK1 |
| ABL |
| p38 |
| RIPK |
| RAF |

Functional Kinase Inhibition Assay

This experiment was conducted by mixing the test kinase, 10 μM γ-33P-ATP, positively charged substrate, magnesium acetate, 1 μM test compound, and reaction buffer at room temperature. The reaction is then stopped by the addition of phosphoric acid solution. 10 μL of the reaction is filtered through a P30 filament, washed properly, dried, and finally subjected to scintillation counting. The inhibition of a given kinase is represented by the function percentage of control (F-POC) which is calculated as follows:

$$F\text{-}POC = \frac{[\text{mean}(\text{counts} - \text{blanks})]_{test} \times 100}{[\text{mean}(\text{counts} - \text{blanks})]_{negative\ control}}.$$

The assay was performed in duplicates. Dose-response curves were fitted using nonlinear regression as implemented in GraphPad Prism software (version 5.02). A Sigmoidal dose-response (variable slope) was used in this case (FIG. 4). Kinase inhibition assays were performed by Millipore Corp. (Dundee, UK).

of their cellular actions. The three compounds gave reproducible results, and compound 15 was chosen subsequently by the DTP-BEC (Developmental Therapeutic Program-Biological Evaluation Committee) to advance to the MTD (Maximum Tolerated Dose) testing in vivo. According to the NCI-anticancer screening paradigm, if 15 is safe in healthy in vivo models, it will be further subjected to the in vivo hollow fiber assay, and possibly human tumor xenografts in an attempt to measure its in vivo anticancer potential (Shoemaker, R. H. *Nature Reviews Cancer* 2006, 6, 813-823; Skehan, P. et al. *Journal of the National Cancer Institute* 1990, 82, 1107-1112; Takimoto, C. H. *Cancer Chemotherapy and Pharmacology, Supplement* 2003, 52).

The GI50 (dose inhibiting 50% of the growth compared to control), TGI (dose inhibiting the growth completely), and LC50 (Dose killing 50% of the starting number of cells) values result from screening of compounds 4, 15, and 16 against the NCI-60 cell line panel after 48 hours treatment are shown in Table 2. All values are given in μM. Cells highlighted in bold have values: 0.1<GI50≤1 μM.

TABLE 2

| | Cell line | | | | | | | | |
|---|---|---|---|---|---|---|---|---|---|
| | 4 | | | 15 | | | 16 | | |
| | $GI_{50}$ | TGI | $LC_{50}$ | $GI_{50}$ | TGI | $LC_{50}$ | $GI_{50}$ | TGI | $LC_{50}$ |
| Leukemia | | | | | | | | | |
| CCRF-CEM | 10.30 | 64.40 | >100 | 10.00 | 60.90 | >100 | ND | ND | ND |
| HL-60(TB) | 11.90 | 41.80 | >100 | 11.20 | 38.60 | >100 | 0.35 | 1.54 | 6.76 |
| K-562 | 0.47 | >100 | >100 | 0.37 | >100 | >100 | 0.37 | 2.23 | >100 |
| M0LT-4 | 8.88 | 40.60 | >100 | 4.02 | 27.60 | >100 | 0.30 | 1.34 | >100 |
| RPMI-8226 | 0.32 | 21.80 | 97.30 | 0.07 | 14.30 | >100 | 0.21 | 0.60 | 3.89 |
| Non-small cell lung cancer | | | | | | | | | |
| A549/ATCC | 7.82 | 35.70 | >100 | 12.20 | >100 | >100 | 1.17 | 3.09 | 8.13 |
| EKVX | 0.39 | 33.10 | >100 | 0.20 | 61.40 | >100 | 1.45 | 4.90 | >100 |
| HOP-62 | 16.40 | 51.60 | >100 | 18.20 | >100 | >100 | 1.62 | 3.47 | 7.41 |
| HOP-92 | 5.43 | 24.20 | 62.00 | 9.91 | 80.09 | >100 | ND | ND | >100 |
| NCI-H226 | 11.10 | 48.40 | >100 | 5.96 | >100 | >100 | 0.42 | 2.09 | 7.94 |
| NCI-H23 | 0.44 | 30.80 | >100 | 0.09 | 33.30 | >100 | 1.07 | 2.69 | 6.92 |
| NCI-H322M | 24.70 | >100 | >100 | 48.90 | >100 | >100 | 2.04 | 4.79 | >100 |
| NCI-H460 | 10.20 | 23.70 | 55.00 | 5.06 | 30.70 | >100 | 1.51 | 4.27 | >100 |
| NCI-H522 | 13.80 | 40.30 | >100 | 4.59 | 55.40 | >100 | 0.62 | 2.09 | 5.13 |
| Colon cancer | | | | | | | | | |
| COLO 205 | 30.40 | >100 | >100 | 14.10 | 38.20 | >100 | 1.41 | 2.75 | 5.50 |
| HCC-2998 | 15.90 | 60.90 | >100 | 13.50 | 48.90 | >100 | 1.78 | 3.98 | 8.91 |
| HCT-116 | 0.27 | 13.20 | 36.40 | 0.25 | 25.00 | >100 | 1.07 | 3.55 | >100 |
| HCT-15 | 19.40 | 63.20 | >100 | 15.80 | >100 | >100 | 1.35 | 3.55 | 9.33 |
| HT29 | 15.50 | 35.10 | 79.20 | 14.00 | 83.20 | >100 | 3.24 | 9.33 | >100 |
| KM12 | 12.60 | 25.10 | 50.10 | 11.00 | 24.30 | 53.80 | 0.79 | 2.40 | 6.61 |
| SW-620 | 12.80 | 27.70 | 59.90 | 12.50 | 45.10 | >100 | 1.91 | 4.27 | >100 |
| CNS cancer | | | | | | | | | |
| SF-268 | 19.50 | 57.20 | >100 | 27.50 | >100 | >100 | 2.57 | >100 | 5.01 |
| SF-295 | 0.31 | 26.00 | >100 | 0.22 | 23.10 | >100 | 1.00 | 2.24 | >100 |
| SF-539 | 14.40 | 28.50 | 56.10 | 36.40 | >100 | >100 | 1.95 | 4.90 | >100 |
| SNB-19 | 12.30 | >100 | >100 | 11.00 | >100 | >100 | 2.82 | 8.91 | >100 |
| SNB-75 | 16.50 | 78.20 | >100 | 9.32 | 58.20 | >100 | 2.34 | 5.89 | >100 |
| U251 | 11.20 | 24.60 | 54.10 | 9.49 | >100 | >100 | 2.04 | 6.61 | >100 |
| Melanoma | | | | | | | | | |
| LOX 1MVI | 0.86 | 19.60 | 44.30 | 0.53 | 28.70 | 97.30 | 1.15 | 2.45 | 5.13 |
| MALME-3M | 12.70 | 33.60 | 89.20 | 6.25 | 42.20 | >100 | 1.26 | 2.57 | 5.25 |
| M14 | 13.40 | 26.30 | 51.60 | 11.40 | 32.70 | 93.70 | 1.00 | 2.14 | 4.68 |
| MDA-MB-435 | 2.64 | 27.50 | 91.40 | 1.78 | >100 | >100 | 0.95 | 2.14 | 4.57 |
| SK-MEL-2 | 18.20 | 35.80 | 70.30 | 24.20 | >100 | >100 | 1.26 | 2.69 | 5.89 |
| SK-MEL-28 | 22.00 | 99.30 | >100 | 22.70 | >100 | >100 | 1.48 | 2.82 | 5.25 |
| SK-MEL-5 | 0.15 | 13.90 | 37.70 | 0.06 | 2.90 | 20.80 | 0.31 | 1.20 | 3.47 |
| UACC-257 | 0.50 | 16.80 | 41.40 | 1.97 | 26.80 | >100 | 1.29 | 2.63 | 5.37 |
| UACC-62 | 10.60 | 25.90 | 63.10 | 8.86 | 80.90 | >100 | 0.48 | 1.86 | 5.37 |
| Ovarian cancer | | | | | | | | | |
| IGROVI | 19.80 | 63.30 | >100 | 16.70 | 49.80 | >100 | 0.52 | 1.82 | 5.01 |
| OVCAR-3 | 11.20 | 23.20 | 48.20 | 15.40 | >100 | >100 | 1.62 | 8.13 | >100 |
| OVCAR-4 | 0.09 | >100 | >100 | 0.16 | 58.80 | >100 | 0.43 | 1.95 | 7.59 |
| OVCAR-5 | 19.40 | 69.80 | >100 | 29.50 | >100 | >100 | 2.34 | 5.75 | >100 |
| OVCAR-8 | 5.90 | 25.60 | 71.30 | 9.16 | >100 | >100 | 0.40 | 3.31 | >100 |
| NCI/ADR-RES | 0.63 | 17.60 | 66.40 | 0.68 | 21.50 | >100 | 0.28 | 8.51 | >100 |
| SK-OV-3 | 25.50 | >100 | >100 | 63.80 | >100 | >100 | 1.82 | 4.47 | >100 |
| Renal cancer | | | | | | | | | |
| 786-0 | 12.80 | 36.70 | >100 | 10.70 | 54.80 | >100 | 2.34 | 6.61 | >100 |
| A498 | 11.70 | 24.20 | 50.10 | 37.50 | >100 | >100 | 0.63 | 5.37 | >100 |
| ACHN | 12.00 | 42.40 | >100 | 3.61 | 82.50 | >100 | 1.58 | 4.57 | >100 |
| CAKI-1 | 3.79 | 39.30 | >100 | 5.44 | 94.80 | >100 | 0.59 | 1.91 | 4.47 |
| RXF 393 | 17.20 | 57.90 | >100 | 14.30 | 41.60 | >100 | 2.88 | 11.48 | >100 |
| SN12C | 10.90 | 24.40 | 54.80 | 7.24 | 59.00 | >100 | 2.29 | 7.08 | >100 |
| TK-10 | 13.70 | 60.80 | >100 | 10.90 | >100 | >100 | 2.45 | 6.17 | 39.81 |
| UO-31 | 13.30 | 38.40 | >100 | 4.90 | 60.50 | >100 | 0.43 | 1.82 | 4.37 |
| Prostate cancer | | | | | | | | | |
| PC-3 | 15.60 | >100 | >100 | 10.50 | >100 | >100 | 0.66 | 2.88 | >100 |
| DU-145 | 11.80 | 30.70 | 79.80 | 16.00 | >100 | >100 | 2.24 | 6.46 | >100 |
| Breast cancer | | | | | | | | | |
| MCF7 | 3.24 | 58.20 | >100 | 1.94 | 72.80 | >100 | 0.85 | 2.29 | 5.62 |
| MDA-MB-231/ATCC | 15.60 | 38.10 | 92.80 | 17.00 | 84.90 | >100 | 2.45 | 2.95 | >100 |
| HS 578T | 20.00 | 54.80 | >100 | 49.60 | >100 | >100 | 2.45 | 7.41 | >100 |

TABLE 2-continued

| | Cell line | | | | | | | | |
|---|---|---|---|---|---|---|---|---|---|
| | 4 | | | 15 | | | 16 | | |
| | $GI_{50}$ | TGI | $LC_{50}$ | $GI_{50}$ | TGI | $LC_{50}$ | $GI_{50}$ | TGI | $LC_{50}$ |
| BT-549 | 1.26 | 18.40 | 43.00 | 0.34 | 10.70 | >100 | 0.44 | 1.74 | 5.37 |
| T-47D | 0.71 | 45.50 | >100 | 1.25 | >100 | >100 | 0.24 | 7.59 | 5.62 |
| MDA-MB-468 | 0.06 | 2.73 | >100 | 0.03 | 2.22 | >100 | 0.74 | 3.47 | >100 |
| Mean | 5.24 | 37.15 | 81.28 | 4.46 | 51.28 | >100 | 1.05 | 3.24 | 22.91 |

Compound 16 (NSC: D-750776) shows the highest overall potency and non-selectivity against the cell lines and it does not display a significant difference between its cytostatic markers (mean GI50=1.05 μM and mean TGI=3.24 μM) and cytotoxic indicator (LC50=22.91 μM). These data could be projected into potential toxicity against normal cells resulting in a narrow therapeutic index. On the other hand, 4 (NSC: D-750901) and 15 (NSC: D-750905) display a pattern of selective cytostatic potency against certain cell lines scattered among different tissues of origin. For example, 15 is potent against RPMI-8226 (leukemia, GI50=68 nM), NCI-H23 (lung, GI50=90 nM), SK-MEL-5 (skin, GI50=61 nM), and MDA-MB-468 (breast, GI50=30 nM) cancer cell lines. These two derivatives, 4 and 15, also show a significant difference between their cytostatic markers (mean GI50 & mean TGI) and cytotoxic indicator (mean LC50). These data may classify 4 and 15 as cytostatic compounds whereas 16 may be described as a cytotoxic agent. According to the data presented in Table 2, and the testing reports obtained from the NCI-60 screening, the relationships between the structure variations of the piperazinylpyrimidine derivatives and their cytostatic/cytotoxic activities can be summarized as shown in FIG. 5. A benzyl group in the 5-position of pyrimidine ring may lead to more antiproliferative activity compared to ethyl substitution. Derivatives based on 2-phenylquinazoline based derivatives show overall weaker antiproliferative potential compared to the quinazoline based derivatives. Concerning the linkers in group II compounds, the para orientation shows the least cytotoxic activity whereas the meta positioning leads to the most potent derivatives (e.g., compound 16). Incorporation of a flexibility inducing element may have refined the series into the selective cytostatic performance of 15. Without being bound by any theory, the correlation between the cellular profile of 4 (group I) and 15 (group II) in both terms of cellular selectivity and cytostatic rather than cytotoxic action raises the hypothesis that they both can affect similar set of targets in the cell and that 15, through its flexible methylene group, is able to attain a conformational ensemble very similar to those attained by the more rigid derivative, 4, devoid of any linkers.

The concentration and time dependencies of the antiproliferative activity of compounds 4, 15, and 16 against MDA-MB-468 cell line were further investigated using MTT assay. This cell line represents the triple negative/basal like breast carcinoma which is usually accompanied by frequent relapses and poor survival, reflecting the need for efficient yet safe agents to be used in this specific clinical setting. The MDA-MB-468 cell line is also sensitive to DNA-damaging agents which are known to be highly toxic and non-selective (Oliveras-Ferraros, C. et al. *International Journal of Oncology* 2008, 33, 1165-1176). MDA-MB-468 cell line is known to overexpress EGFR receptor (Nautiyal, J. et al. *Molecular Cancer Therapeutics* 9, 1503-1514.). Therefore, gefitinib, known as an EGFR inhibitor, was included in the study as a positive control. According to the dose-response curves shown in FIG. 6, the antiproliferative activity of a given test compound is directly proportional to the treatment time and the concentration. The ranking of activity according to the obtained IC50 values is as follows: 4 and 15 are more antiproliferative than 16 than gefitinib.

Kinase Profiling of 4, 15, and 16

The compounds of the present invention were structurally designed with the intention to interfere with certain members of the human kinome. Compounds 4, 15, and 16 were selected because they represent the three major structural variations and also because they were either selective cytostatic or potent cytotoxic on the cellular level. Compound 4 represents the direct attachment of the quinazoline ring with the piperazinylpyrimidine scaffold (group I). Compound 15 exemplifies the use of a flexible linker whereas compound 16 has a more rigid incorporated linker and both belong to group II (FIG. 1). Two different kinase experiments were chosen for the current study. One is classified as a binding or non-biochemical testing while the other is functional and biochemically oriented.

In order to test the potential of 4, 15, and 16 to bind with the human kinome to which they were designed to target, a kinase binding assay was used to examine the ability of 10 μM of 4, 15, or 16 to interfere with the binding of a given kinase with an immobilized, ATP directed agent (Karaman, M. W. et al. *Nature Biotechnology* 2008, 26, 127-132; Fabian, M. A. et al. *Nature Biotechnology* 2005, 23, 329-336; Pettus, L. H. et al. *Journal of Medicinal Chemistry* 2010, 53, 2973-2985; Andersen, C. B. et al. *ACS Chemical Biology* 2008, 3, 180-192; Jiang, J. K. et al. *Journal of Medicinal Chemistry* 2008, 51, 8012-8018; Burns, C. J. et al. *Bioorganic and Medicinal Chemistry Letters* 2009, 19, 1206-1209; Chao, Q. et al. *Journal of Medicinal Chemistry* 2009, 52, 7808-7816.). A single dose of 10 μM was chosen to allow for detecting kinases able to bind to the test compounds. In this binding assay, a set of 243 kinases were included. This set of kinases covers i) wild-type versus mutant kinases; and ii) phosphorylated versus non-phosphorylated set of either wild-type or mutant ABL1 kinases (Table 3). Table 4 lists the kinases tested. A given interaction is represented by a numerical value called binding percentage of control (B-POC). The lower the B-POC value, the stronger the test compound binds with the test kinase. Only results with B-POC≤50 are shown in Table 1 and are highlighted based on the kinases subfamilies, which aids in detecting the selectivity of the test compounds for being prototype inhibitors of certain kinase subfamilies. The kinases are ranked from the most to the least sensitive kinase towards binding with a given test compound. Table 1 illustrates that within the set of tested kinases, certain members of CDK, CK1, PDGFR, DDR, ABL, p38, RAF, or RIPK subfamilies are more or less recognized by the three test compounds. Some members of CK1 subfamily are commonly recognized by the three test compounds. Compound 15 shows almost equal affinity to bind to several members of CK1 subfamily whereas CSNK1D is almost equivalently sensitive to the three derivatives; B-POC=26 against 4, B-POC=23 against 15, and B-POC=22 against 16. Another CKI member, CSNKIE, is found to be sensitive towards 15 and 16 more than towards 4. CSNKIE is found to be significantly expressed in several cancer types compared to their normal tissues (Yang, W. S.; Stockwell, B. R. Genome Biology 2008). Without being bound by any theory, the above results suggest that for CK1 subfamily members, the combination of piperazinylpyrimidine scaffold with quinazoline ring may be relevant for binding irrespective to the presence of linkers or a specific linker. Accordingly, CK1 family kinases, especially CSNK1D, may contain a common binding site which is able to accommodate piperazinylpyrimidine derivatives of different molecular sizes and linkers.

Compound 4 exhibits obvious tendency to bind strongly with certain wild-type and/or mutant members of the CDK and PDGFR subfamilies. Without being bound by any theory, the binding of compound 4 could be attributed to sterics, as 4 is smaller in size than both 15 and 16 and that the targeted binding site of these subfamilies, CDK and PDGFR, is unable to accommodate these larger derivatives (15 and 16). Additionally, compound 15 binds with higher affinity to BRAF and its common V600E mutant whereas 4 and 16 are recognized by RIPKI, another TKL (tyrosine kinase like) kinase. Among the tested unphosphorylated and phosphorylated derivatives of ABL1, only two close mutants are bound by the test compounds.

TABLE 3

|  | Phosphorylated | Non-phosphorylated |
|---|---|---|
| Wild-type | 1 | 198 |
| Mutants | 8 | 36 |

TABLE 4

|  | Description | Kinases |
|---|---|---|
| Wild-type | Phosphorylated | ABL1-phosphorylated |
|  | Non-phosphorylated | ABL1, ABL2, ACVR1, ACVR1B, ACVR2A, ACVR2B, ACVRL1, ADCK3, ADCK4, AKT1, AKT2, AKT3, ALK, AURKA, AURKB, AURKC, AXL, BLK, BMPR1A, BMPR1B, BMPR2, BMX, BRAF, BRK, BTK, CAMK2B, CDC2L1, CDC2L2, CDC2L5, CDK11, CDK2, CDK3, CDK4-cyclinD1, CDK4-cyclinD3, CDK5, CDK7, CDK8, CDK9, CDKL1, CDKL2, CDKL3, CDKL5, CHEK1, CHEK2, CLK3, CSF1R, CSK, CSNK1A1, CSNK1A1L, CSNK1D, CSNK1E, CSNK1G1, CSNK1G2, CSNK1G3, CSNK2A1, CSNK2A2, CTK, DAPK1, DAPK2, DAPK3, DCAMKL1, DDR1, DDR2, DYRK1B, EGFR, EPHA2, EPHA3, EPHA6, EPHA8, EPHB2, EPHB3, EPHB4, ERK1, FAK, FER, FES, FGFR1, FGFR2, FGFR3, FGFR4, FGR, FLT1, FLT3, FLT4, FRK, FYN, GSK3A, GSK3B, HCK, IGF1R, IKK-alpha, IKK-beta, IKK-epsilon, INSR, INSRR, ITK, JAK1(JH1domain-catalytic), JAK2(JH1domain-catalytic), JAK3(JH1domain-catalytic), JNK1, JNK2, JNK3, KIT, LCK, LKB1, LTK, LYN, MAP3K1, MAP3K15, MAP3K2, MAP3K3, MAP3K4, MAP4K2, MAP4K3, MAP4K4, MAP4K5, MAPKAPK2, MARK3, MEK1, MEK2, MERTK, MET, MKNK1, MKNK2, MLK1, MST1R, MTOR, MUSK, NEK1, p38-alpha, p38-beta, p38-delta, p38-gamma, PAK1, PAK2, PAK3, PAK4, PAK6, PAK7, PCTK1, PDGFRA, PDGFRB, PDPK1, PIK3C2B, PIK3CA, PIK3CG, PIM1, PIM2, PIM3, PKAC-alpha, PLK1, PLK2, PLK3, PLK4, PRKCE, PRP4, PYK2, RAF1, RET, RIOK1, RIOK2, RIOK3, RIPK1, RIPK2, RIPK4, ROCK2, ROS1, RSK2(Kin.Dom.1-N-terminal), SNARK, SRC, SRMS, SRPK3, STK39, SYK, TAK1, TEC, TGFBR1, TGFBR2, TIE1, TIE2, TNIK, TNK1, TNK2, TNNI3K, TRKA, TRKB, TRKC, TSSK1B, TXK, TYK2(JH1domain-catalytic), TYRO3, ULK2, VEGFR2, VRK2, WEE1, YANK3, YES, ZAP70 |
| Mutants | Phosphorylated | ABL1(E255K)-phosphorylated, ABL1(F317I)-phosphorylated, ABL1(F317L)-phosphorylated, ABL1(H396P)-phosphorylated, ABL1(M351T)-phosphorylated, ABL1(T315I)-phosphorylated, ABL1(Y253F)-phosphorylated, ABL1(Q252H)-phosphorylated, |
|  | Non-phosphorylated | ABL1(F317I), ABL1(F317L), ABL1(H396P), ABL1(Q252H), ABL1(T315I), BRAF(V600E), EGFR(E746-A750del), EGFR(G719C), EGFR(G719S), EGFR(L747-E749del, A750P), EGFR(L747-S752del, P753S), EGFR(L747-T751del, Sins), EGFR(L858R), EGFR(L858R, T790M), EGFR(L861Q), EGFR(S752-I759del), EGFR(T790M), FGFR3(G697C), FLT3(D835H), FLT3(D835Y), FLT3(ITD), FLT3(K663Q), FLT3(N841I), FLT3(R834Q), KIT(A829P), KIT(D816H), KIT(D816V), KIT(L576P), KIT(V559D), KIT(V559D, T670I), KIT(V559D, V654A), MET(M1250T), MET(Y1235D), RET(M918T), RET(V804L), RET(V804M), |

ABL1(F317I) is moderately recognized by 4 (B-POC=30) and 16 (B-POC=20) whereas ABL1(F317L) is more strongly recognized by 15 (B-POC=6.8). Since phosphorylated kinases are presumed to exist preferentially in the active state, the data suggest that the test compounds interact with active kinases and inhibit their phosphotransferase function. Accordingly, a biochemical functional screening of the test compounds was pursued. Compound 4 is able to target PDGFR wild-type and mutants without affecting ABL1 or ABL2 kinases (only phosphorylated ABL1(F317I) mutant was targeted by 4). It is common for inhibitors binding to the ABL subfamily to also target the PDGFR subfamily and vice versa (See e.g., imatinib; Cohen, M. H. et al. *Clinical Cancer Research* 2002, 8, 935-942; Dagher, R. et al. *Clinical Cancer Research* 2002, 8, 3034-3038). Compound 4 represents a structure that can discriminate between PDFGR and ABL subfamilies. Only interactions with B-POC≤35 were considered significant and thus used for calculating the selectivity scores of the test compounds (Table 1, FIG. 2). The test compounds, as prototype kinase binders, have excellent overall selectivity towards certain kinase subfamilies. Based on the results of this primary single-dose screen, the concentration-dependent potential of compound 4 to bind to FLT3, KIT, KIT(D816H), or KIT(D816V) was investigated. The Kd (dissociation constant) of the four interactions was determined (Table 1). Dose response curves of compound 4 against FLT3, KIT, KIT(D816H), or KIT(D816V) are shown in FIG. 3.

In order to evaluate whether the molecules could inhibit the phosphotransferase kinase function a radiometric based assay was used to measure the ability of 1 μM of compounds 4, 15, or 16 to interfere with the function of a set of 55 protein kinases; 39 wild-type and 16 mutants (Table 5) (Davies, S. P. et al. *Biochemical Journal* 2000, 351, 95-105; Copeland, R. A. *Analytical Biochemistry* 2003, 320, 1-12). This set of tested kinases was chosen based on the results of the binding assay described above. Again the ability of 1 μM of a given test compound to inhibit the phosphotransferase function of a given kinase is expressed by functional percentage of control (F-POC) value which is also inversely proportional to the potency of the test compound, at that specific concentration, for a given kinase. The most promising interactions, at a single dose, were further investigated to determine the IC50 values. The IC50 of compound 4 was determined against KIT, KIT(D816H), KIT(D816V), KIT(V560G), FLT3, PDGFRA (V561D), and PDGFRA(D842V) (Table 6). The results of kinase function inhibition assay are shown in Table 6, including the F-POC of 1 μM of compounds 4, 15, and 16 against the most sensitive kinases tested within this experiment. Kinases are ranked according to their sensitivity towards binding by each compound separately from the most (lower F-POC) to the least (higher F-POC) sensitive. Kinases within the same subfamily are highlighted. The IC50 values of compound 4 against a set of PDGFR subfamily selected kinases and mutants are in parentheses and expressed in μM. Both the F-POC and IC$_{50}$ values are the average of duplicate measurements. Dose-response curves were used to determine the IC50 values (FIG. 4).

The three test compounds, weakly inhibit the same member of CK1 subfamily, CSNK1D. Compound 4 demonstrates the ability to inhibit the function of some PDGFR subfamily members; both wild-type and mutants, without affecting ABL subfamily members. On the other hand, 15 and 16 show weak inhibitory action over ABL kinase and some members of PDGFR subfamily.

TABLE 5

| Description | Kinases |
|---|---|
| Wild-type (39) | Abl, CDK2/cyclinA, CDK2/cyclinE, CDK6/cyclinD3, CK1, CK1δ, CK2, CK2α2, cKit, c-RAF, c-SRC, DDR2, EGFR, FGFR1, Flt3, IKKα, IKKβ, JAK2, JAK3, JNK1α1, JNK2α2, JNK3, MAPK1, MAPK2, MEK1, Met, mTOR, p70S6K, PAK5, PDGFRα, PDGFRβ, PDK1, PI3K/p85α, PI3K/p65α, PKBα, PKBβ, PKBγ, RIPK2, SAPK3 |

TABLE 5-continued

| Description | Kinases |
|---|---|
| Mutants (16) | Abl (H396P), Abl(T315I), cKit(D816H), cKit(D816V), cKit(V560G), cKit(V654A), EGFR(L858R), EGFR(L861Q), EGFR(T790M), EGFR(T790M, L858R), FGFR1(V561M), Flt3(D835Y), PDGFRα(D842V), PDGFRα(V561D), PI3K(E545K)/p85α, PI3K(H1047R)/p85α |

TABLE 6

| | F-POC (IC$_{50}$) | | | | |
|---|---|---|---|---|---|
| Kinase | 4 | Kinase | 15 | Kinase | 16 |
| PDGFRA(V561D) | 20 (0.295) | ABL | 80 | MAPK1 | 73 |
| PDGFRA(D842V) | 25 (0.316) | FLT3 | 80 | CSNK1D | 74 |
| KIT(D816H) | 30 (0.316) | PKBβ | 82 | PKBβ | 83 |
| KIT(V560G) | 36 (0.699) | CSNK1D | 87 | KIT(V560G) | 86 |
| FLT3 | 74 (6.692) | | | ABL | 87 |
| MET | 75 | | | | |
| KIT(D816V) | 83 (2.823) | | | | |
| PKBβ | 89 | | | | |
| CSNK1D | 90 | | | | |
| KIT | 94 (>10.0) | | | | |

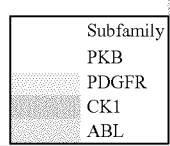

| Subfamily |
|---|
| PKB |
| PDGFR |
| CK1 |
| ABL |

Both kinase profiling experiments, binding and functional, revealed that compound 4 shows more potential to either bind to or inhibit the function of some of the KIT and PDGFRA mutants compared to their wild-type isoforms. The B-POC of 10 μM and F-POC of 1 μM of compound 4 measured in the binding and function inhibition experiments, respectively, are shown in Table 7. The location of each mutation is included (Gajiwaia, K. S. et al. *Proceedings of the National Academy of Sciences of the United States of America* 2009, 106, 1542-1547; Heinrich, M. C. et al. *Science* 2003, 299, 708-710.). It has been reported that different gain-of-function mutations of the KIT kinase lead to constitutive catalytic activity independent of activation by extracellular stem cell factor. The occurrence of these mutations was detected in cases where marketed KIT inhibitors (imatinib, dasatinib and sunitinib) face resistance by the target cancer cells and become inefficacious in the treatment of chronic myeloid leukemia (CML) and/or gastrointestinal stromal tumors (GIST) (Gajiwaia, K. S. et al. *Proceedings of the National Academy of Sciences of the United States of America* 2009, 106, 1542-1547; Masson, K.; Ronnstrand, L. *Cellular Signalling* 2009, 21, 1717-1726; Bougherara, H. et al. *Molecular Cancer Research* 2009, 7, 1525-1533). Compound 4 shows higher activity against the KIT A-loop mutants; D816H and D816V compared to its activity against wild-type KIT which is supported by both the Kd values in the binding screen and the IC50 values in the functional assay. As common with many other kinase inhibitors, mutations in the gatekeeper of KIT could render the protein less liable to binding by 4; an observation reinforced by the increase in the B-POC value of the juxtamembrane mutant KIT(V559D) upon mutation of the gatekeeper in the double mutant KIT(V559D, T670I). Without being bound by any theory, this may suggest that the gatekeeper residue and probably the adjacent hinge region are critical in binding of 4 to KIT. It is clear that 4 can bind the KIT(D816V) (Kd=0.11 μM) more than it binds KIT(D816H) (Kd=1.3 μM), whereas it inhibits the function of KIT(D816H) (IC50=0.316 μM) more than it inhibits KIT(D816V) (IC50=2.82 μM). Such opposite effects, on two different mutations at the same location, may originate from the difference in the preferred conformational ensembles. Also, this highlights the potential effect of a single amino acid mutation upon the probability distribution of the protein's conformations to be selected for binding by a given small molecule like 4. The ability of compound 4 to efficiently bind to certain KIT mutants, that are resistant to other kinase inhibitors, more than it binds to the wild-type suggest that 4 can be selective towards cancer phenotypes harboring and depending on such mutant KIT forms versus normal cells depending mainly on wild-type KIT to function. Compound 4 also exhibits a similar fashion of selectivity towards certain PDGFRA mutants (V561D in the juxtamembrane or D842V in the A-loop) as illustrated by the F-POC and IC50 determination. Such PDGFRA mutants exhibit differential resistance towards certain kinase inhibitors like imatinib and nilotinib and become common in certain forms of resistant cancer phenotypes (Heinrich, M. C. et al. *Science* 2003, 299, 708-710; Liegl-Atzwanger, B. et al. *Virchows Archiv* 2010, 456, 111-127; Pasini, B. et al. *Journal of Clinical Endocrinology and Metabolism* 2007, 92, 3728-3732; Weisberg, E. et al. *Gastroenterology* 2006, 131, 1734-1742).

TABLE 7

| Kinase | Location | B-POC | $K_d$ (µM) | F-POC | $IC_{50}$ (µM) |
|---|---|---|---|---|---|
| KIT(D816V) | A-loop | 0.5 | 0.11 | 83 | 2.82 |
| KIT(D816H) | A-loop | 30 | 1.3 | 30 | 0.316 |
| KIT(A829P) | A-loop | 84 | ND | ND | ND |
| KIT(V559D) | JM | 4.3 | ND | ND | ND |
| KIT(L576P) | JM | 9.8 | ND | ND | ND |
| KIT(V559D, T670I) | JM and GK | 66 | ND | ND | ND |
| KIT(V560G) | JM | ND | ND | 36 | 0.699 |
| KIT | Wild-type | 9.1 | 2.5 | 94 | >10.0 |
| PDGFRA(V561D) | JM | ND | ND | 20 | 0.295 |
| PDGFRA(D842V) | A-loop | ND | ND | 25 | 0.316 |
| PDGFRA | Wild-type | 21 | ND | 116 | ND |

JM = juxtamembrane domain;
GK = gatekeeper residue;
ND = not determined.

Compound 15 demonstrates a similar trend of selectivity towards the mutant BRAF(V600E) versus the wild-type BRAF (Table 1). BRAF(V600E) mutant is commonly found in several kinds of cancer especially melanoma and GIST. This mutation has attracted the attention of research groups to develop specific inhibitors against it (Liegl-Atzwanger, B. et al. *Virchows Archiv* 2010, 456, 111-127; Suijkerbuijk, B. M. J. M. et al. *Journal of Medicinal Chemistry* 2010, 53, 2741-2756). ABL1 mutants have been generally shown to affect the sensitivity towards ABL kinase inhibitors. Point mutations in codon 317 of ABL1 have been found to specifically impart resistance towards dasatinib. 58-60 Compound 4 and 16 have moderate affinity to bind to the phosphorylated form of ABL1 (F317I) while 15 has stronger binding affinity towards the phosphorylated form of ABL1(F317L).

As revealed by Table 1 and Table 6, although compounds 4 and 15 have certain common kinase targets, they do not share an overall similar selectivity profile in that 4 is more active towards the PDGFR subfamily. This is contrary to the correlation of their cellular profile against the NCI-60 panel of cancer cells. One possible scenario is that 4 and 15 could equally inhibit other protein(s) that belong to a different protein family other than protein kinases. It also may be possible that 4 and 15 target the same signaling transduction pathway at different points.

The observed binding affinity of 4 against the wild-type KIT and its D816V mutant, obtained from the binding data, to the respective binding affinity of 38 kinase inhibitors against the same two kinases observed under very similar experimental conditions, is shown in Table 8 (Karaman, M. W. et al. *Nature Biotechnology* 2008, 26, 127-132). The $K_d$ values of the reference kinase inhibitors were determined experimentally against the two kinases similarly to that of 4 and were obtained from literature. $\Delta\Delta G°$, as a measure of the differential binding potential against the mutant KIT(D816V) versus the wild-type KIT, was calculated according to the literature (Kolb, P. et al. *Journal of Medicinal Chemistry* 2008, 51, 1179-1188; AbdulHameed, M. D. M. et al. *Journal of Physical Chemistry B* 2006, 110, 26365-26374). A negative $\Delta\Delta G°$ indicates preferential binding to the mutant whereas a positive $\Delta\Delta G°$ indicates increased resistance by the mutant against the specific inhibitor.

The data in Table 8 show that the seven reference kinase inhibitors that have negative $\Delta\Delta G°$ are known to be type-I kinase inhibitors which bind to the same binding site occupied by ATP (Fedorov, O. et al. *Proceedings of the National Academy of Sciences of the United States of America* 2007, 104, 20523-20528; Rixe, O. et al. *Cancer Chemotherapy and Pharmacology* 2009, 64, 1139-1148; Weisberg, E. et al. *Blood* 2008, 112, 5161-5170; Baumli, S. et al. *EMBO Journal* 2008, 27, 1907-1918; Yun, C. H. et al. *Cancer Cell* 2007, 11, 217-227; Boggon, T. J. et al. *Blood* 2005, 106, 996-1002; Stamos, J. et al. *Journal of Biological Chemistry* 2002, 277, 46265-46272). The above observation matches with several published computational as well as experimental reports demonstrating that an aspartic acid to valine mutation in the position 816 of KIT destabilizes the inactive (DFG-out) conformations of KIT. The same mutation would consequently decrease the binding to type-II kinase inhibitors which mainly bind preferentially to the inactive (DFG-out) conformational ensemble of KIT. In addition, the experimental tendency of 4 to bind better to the V816KIT compared to the D816KIT suggests that 4 may be a type-I kinase inhibitor that targets the ATP binding site in contrast to type-II inhibitors which exploit the adjacent allosteric binding site.

TABLE 8

| | $K_d$ (nM) | | |
|---|---|---|---|
| Kinase inhibitor | KIT | KIT(D816V) | $\Delta\Delta G°$ |
| Staurosporine | 19 | 0.64 | −2.01 |
| PKC-412 | 220 | 7.7 | −1.98 |
| 4 | 2500 | 110 | −1.847 |
| LY-333531 | >10000 | 920 | <−1.4 |
| Erlotinib | >10000 | 1600 | <−1.08 |
| Gefitinib | >10000 | 4300 | <−0.49 |
| Flavopiridol | >10000 | 4600 | <−0.45 |
| CI-1033 | 7800 | 3900 | −0.41 |
| ZD-6474 | 260 | 290 | 0.06 |
| VX-680 | 240 | 290 | 0.11 |
| JNJ-7706621 | 1800 | 2500 | 0.19 |
| Dasatinib | 0.62 | 2.6 | 0.85 |
| Sorafenib | 31 | 310 | 1.36 |
| MLN-518 | 2.7 | 29 | 1.40 |
| CHIR-265 | 200 | 6200 | 2.03 |
| ABT-869 | 2 | 81 | 2.19 |
| Imatinib | 14 | 820 | 2.41 |
| BIRB-796 | 170 | >10000 | >2.41 |
| AST-487 | 5.4 | 360 | 2.48 |
| AMG-706 | 3.7 | 410 | 2.78 |
| GW-786034 | 2.8 | 500 | 3.07 |
| CHIR-258 | 7.5 | 1400 | 3.09 |
| AZD-1152HQPA | 17 | 4600 | 3.31 |
| SU-14813 | 0.68 | 340 | 3.68 |
| Sunitinib | 0.37 | 380 | 4.10 |
| PTK-787 | 5.1 | >10000 | >4.48 |
| BMS-387032 | >10000 | >10000 | — |
| CP-690550 | >10000 | >10000 | — |
| CP-724714 | >10000 | >10000 | — |
| EKB-569 | >10000 | >10000 | — |

TABLE 8-continued

| Kinase inhibitor | $K_d$ (nM) | | $\Delta\Delta G°$ |
|---|---|---|---|
| | KIT | KIT(D816V) | |
| GW-2580 | >10000 | >10000 | — |
| Lapatinib | >10000 | >10000 | — |
| MLN-8054 | >10000 | >10000 | — |
| PI-103 | >10000 | >10000 | — |
| Roscovitine | >10000 | >10000 | — |
| SB-202190 | >10000 | >10000 | — |
| SB-203580 | >10000 | >10000 | — |
| SB-431542 | >10000 | >10000 | — |
| VX-745 | >10000 | >10000 | — |

$\Delta\Delta G°$ (Kcal · mol$^{-1}$) = R × T × ln [$K_d$(mutant)/$K_d$(wild-type)] where R = 0.001985 Kcal · mol$^{-1}$ · K$^{-1}$ and T = 298° K.

Treatment of Breast Tumor Cell Line MDA-MB-468 with Compound 15

Treatment of the breast tumor cell line MDA-MB-468 with compound 15 caused the cells to arrest at the G2/M phase of the cell cycle within 24 hours (see FIG. 7). At higher doses a significant fraction of the tumor cells undergo apoptosis within 24 hours, as assessed by Annexin V assay (see FIG. 8).

Although the compounds, compositions, and methods described herein have been described in connection with some variations and/or embodiments, it is not intended to be limited to the specific form set forth herein. Rather, the scope of the methods described herein is limited only by the claims. Additionally, although a feature may appear to be described in connection with particular variations, one skilled in the art would recognize that various features of the described variations and/or embodiments may be combined in accordance with the methods described herein.

Although individual features of the compounds, compositions, and methods described herein may be included in different claims, these may be advantageously combined, and the inclusion in different claims does not imply that a combination of features is not feasible and/or advantageous. Also, the inclusion of a feature in one category of claims does not imply a limitation to this category, but rather the feature may be equally applicable to other claim categories, as appropriate. Where a compound, composition, or method 'comprises' one or more specified items or steps, others can also be included. The invention also contemplates, however, that the described compounds, compositions, or methods may be used without other items or steps and thus it includes the recited composition or process 'consisting of' or 'consisting essentially of' the recited items, materials or steps, as those terms are commonly understood in patent law.

Terms and phrases used in this document, and variations and/or embodiments thereof, unless otherwise expressly stated, should be construed as open ended as opposed to limiting. As examples of the foregoing: the term "including" should be read to mean "including, without limitation" or the like; the terms "example" or "some variations" are used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of methods and compositions described herein may be described or claimed in the singular, the plural is contemplated to be within the scope thereof unless limitation to the singular is explicitly stated. The presence of broadening words and phrases such as "one or more," "at least," "but not limited to," "in some embodiments," or other like phrases in some instances shall not be read to mean that the narrower case is intended or required in instances where such broadening phrases may be absent.

ENUMERATED EMBODIMENTS

The following enumerated embodiments are representative of some aspects of the invention.

1. A compound of formula (I), (II), or (III):

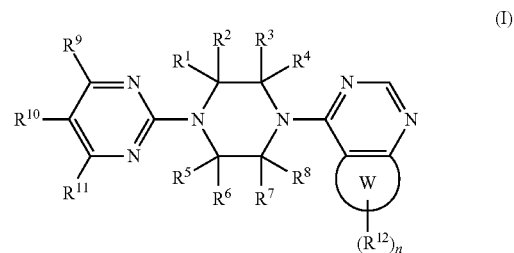

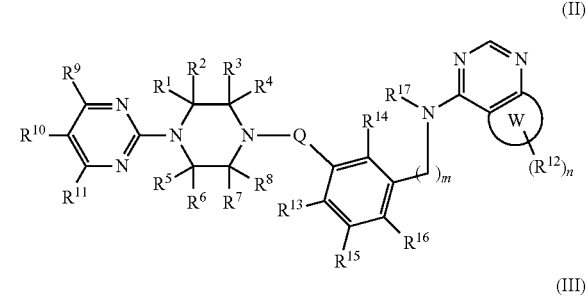

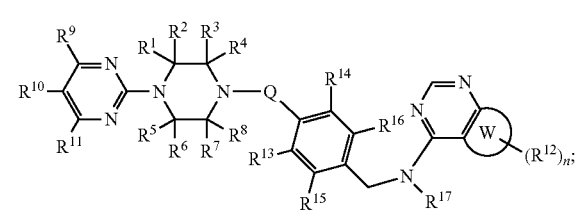

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, CONR$_2$, OOCR, COR, CH(OH)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and wherein each R is optionally substituted, with the proviso that R$^{10}$ for formula (I) must not be hydrogen; and each R$^{17}$ is independently selected from hydrogen or optionally substituted alkyl;

or a pharmaceutically acceptable salt thereof.

2. The compound of embodiment 1, which is a compound of formula (I) or a pharmaceutically acceptable salt thereof.

3. The compound of embodiment 1, which is a compound of formula (II) or a pharmaceutically acceptable salt thereof.

4. The compound of embodiment 1, which is a compound of formula (III) or a pharmaceutically acceptable salt thereof.

5. The compound of any of embodiments 3-4, wherein Q is C=O.

6. The compound of any of embodiments 1-5, wherein each R$^1$, R$^2$, R$^3$, R$^4$, R$^5$, R$^6$, R$^7$, and R$^8$ is hydrogen.

7. The compound of any of embodiments 1-6, wherein each R$^9$ and R$^{11}$ is independently selected from hydrogen, optionally substituted alkyl, optionally substituted aryl, halo, OR, NR$_2$, SR, CN, COOR, CONR$_2$, COR, CH(OH)R, and NO$_2$.

8. The compound of any of embodiments 1-7, wherein each R$^{10}$ is independently selected from optionally substituted alkyl, optionally substituted aryl, halo, OR, NR$_2$, SR, CN, COOR, CONR$_2$, COR, CH(OH)R, and NO$_2$.

9. The compound of any of embodiments 1-8, wherein each R$^{10}$ is independently selected from optionally substituted alkyl or optionally substituted aryl.

10. The compound of any of embodiments 1-9, wherein each R$^{10}$ is —(CH$_2$)$_p$—Ar, wherein p is 1-2 and Ar is optionally substituted phenyl.

11. The compound of any of embodiments 1-10, wherein each R$^9$ and R$^{11}$ is hydrogen and each R$^{10}$ is optionally substituted alkyl.

12. The compound of any of embodiments 1-11, wherein each R$^{10}$ is independently selected from methyl, ethyl, propyl, isopropyl, butyl, isobutyl, sec-butyl, tert-butyl, pentyl, neopentyl, and benzyl.

13. The compound of any of embodiments 1-12, wherein each R$^{10}$ is independently selected from optionally substituted ethyl or benzyl.

14. The compound of any of embodiments 1-13, wherein each R$^{12}$ is independently selected from optionally substituted alkyl, optionally substituted aryl, halo, OR, NR$_2$, SR, CN, COOR, CONR$_2$, COR, CH(OH)R, and NO$_2$.

15. The compound of any of embodiments 1-14, wherein each R$^{12}$ is hydrogen.

16. The compound of any of embodiments 1-15, wherein W in any compound having formula (I), (II), or (III) is:

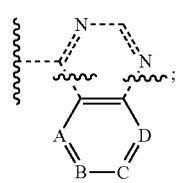

wherein each A, B, C, and D is independently N or CR$^{12}$ in any combination.

17. The compound of embodiment 16, wherein W is selected from the group consisting of:

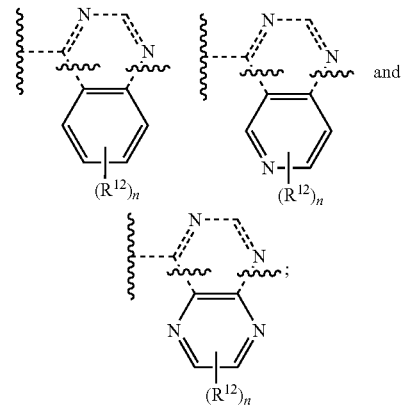

wherein each R$^{12}$ is independently selected from the group consisting of hydrogen, optionally substituted alkyl, optionally substituted aryl, halo, OR, NR$_2$, SR, CN, COOR, CONR$_2$, COR, CH(OH)R, and NO$_2$.

18. The compound of embodiment 17, wherein W is selected from the group consisting of:

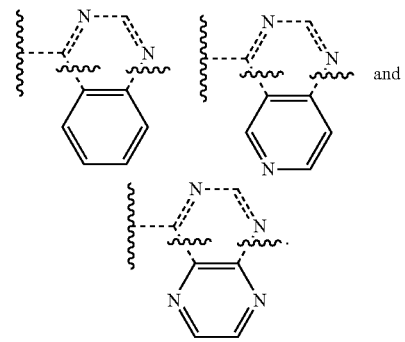

19. The compound of embodiment 18, wherein W is:

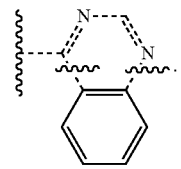

20. The compound of any of embodiments 1-15, wherein W in any compound having formula (I), (II), or (III) is:

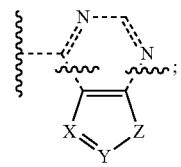

wherein X and Y are N or CR$^{12}$;

Z is selected from the group consisting of $NR^{20}$, O, and S; and $R^{20}$ is hydrogen or $R^{12}$.

21. The compound of embodiment 20, wherein W is selected from the group consisting of:

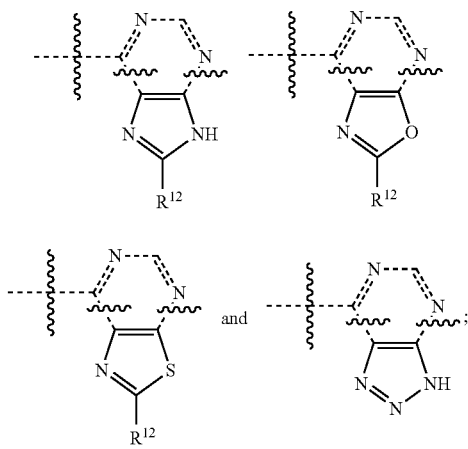

wherein each $R^{12}$ is independently selected from the group consisting of hydrogen, optionally substituted alkyl, and optionally substituted aryl.

22. The compound of embodiment 21, wherein W is selected from the group consisting of:

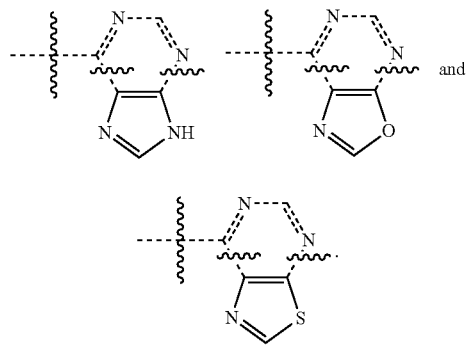

23. The compound of any of embodiments 1-15, wherein W in any compound having formula (I), (II), or (III) is:

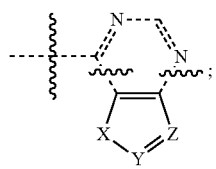

wherein X is selected from the group consisting of $NR^{20}$, O, and S;

Y and Z are N or $CR^{12}$; and $R^{20}$ is hydrogen or $R^{12}$.

24. The compound of embodiment 23, wherein W is selected from the group consisting of:

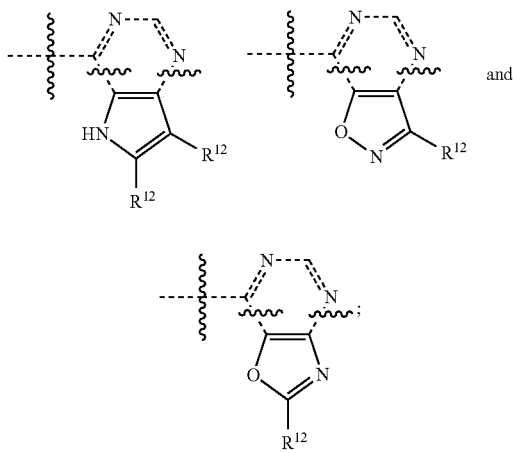

wherein each $R^{12}$ is independently selected from the group consisting of hydrogen, optionally substituted alkyl, and optionally substituted aryl.

25. The compound of embodiment 24, wherein W is selected from the group consisting of:

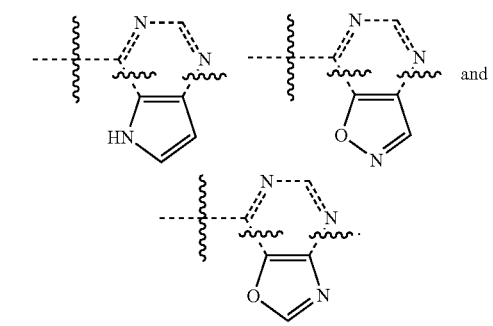

26. The compound of embodiment 1, wherein the compound is:

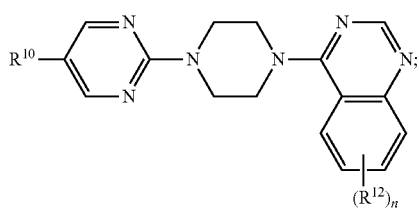

wherein $R^{10}$ is selected from the group consisting of optionally substituted alkyl and optionally substituted aryl;

and wherein each $R^{12}$ is independently selected from the group consisting of hydrogen, optionally substituted alkyl, optionally substituted aryl, halo, OR, $NR_2$, SR, CN, COOR, $CONR_2$, COR, CH(OH)R, and $NO_2$.

27. The compound of embodiment 26, wherein the compound is:

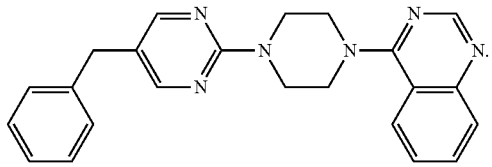

28. The compound of embodiment 1, wherein the compound is:

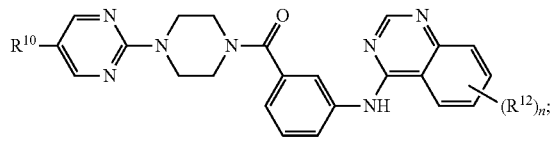

wherein R$^{10}$ is selected from the group consisting of optionally substituted alkyl and optionally substituted aryl;

and wherein each R$^{12}$ is independently selected from the group consisting of hydrogen, optionally substituted alkyl, optionally substituted aryl, halo, OR, NR$_2$, SR, CN, COOR, CONR$_2$, COR, CH(OH)R, and NO$_2$.

29. The compound of embodiment 28, wherein the compound is:

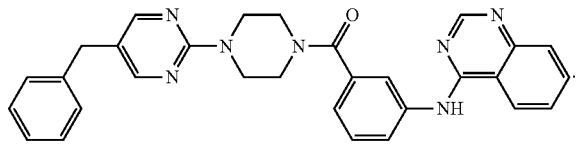 [SMILES: O=C(c1cccc(Nc2ncnc3ccccc23)c1)N1CCN(c2ncc(Cc3ccccc3)cn2)CC1]

30. The compound of embodiment 1, wherein the compound is:

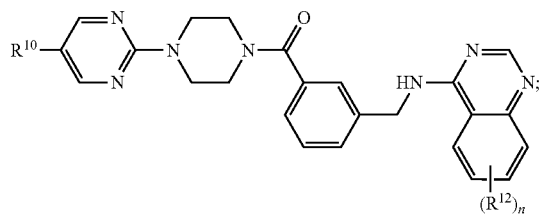

wherein R$^{10}$ is selected from the group consisting of optionally substituted alkyl and optionally substituted aryl;

and wherein each R$^{12}$ is independently selected from the group consisting of hydrogen, optionally substituted alkyl, optionally substituted aryl, halo, OR, NR$_2$, SR, CN, COOR, CONR$_2$, COR, CH(OH)R, and NO$_2$.

31. The compound of embodiment 30, wherein the compound is:

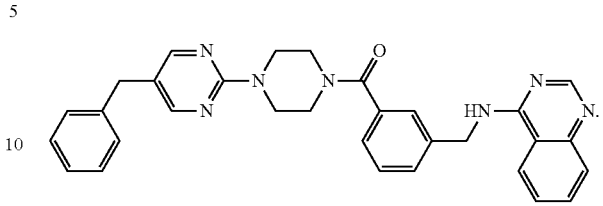

32. The compound of embodiment 1, wherein the compound is:

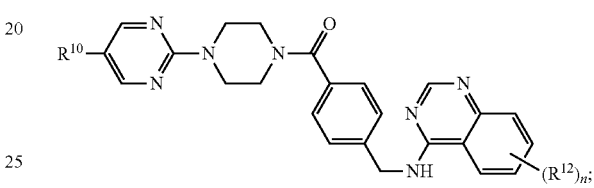

wherein R$^{10}$ is selected from the group consisting of optionally substituted alkyl and optionally substituted aryl;

and wherein each R$^{12}$ is independently selected from the group consisting of hydrogen, optionally substituted alkyl, optionally substituted aryl, halo, OR, NR$_2$, SR, CN, COOR, CONR$_2$, COR, CH(OH)R, and NO$_2$.

33. The compound of embodiment 32, wherein the compound is:

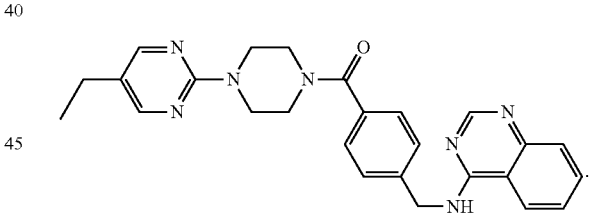

34. A pharmaceutical composition comprising a compound according to any of embodiments 1-33 and at least one pharmaceutically acceptable excipient.

35. The use of a compound according to any of embodiments 1-33 to manufacture a medicament.

36. The method of embodiment 35, wherein the medicament is a medicament for the treatment of a proliferative disorder.

37. A method to identify a molecule that modulates protein kinase activity, said method comprising screening a compound according to any of embodiments 1-33, to identify a compound having an effect on the activity of a protein kinase.

38. A method to treat a proliferative disorder, said method comprising administering to a subject in need of such treatment, an effective amount of a compound of formula (I), (II), or (III):

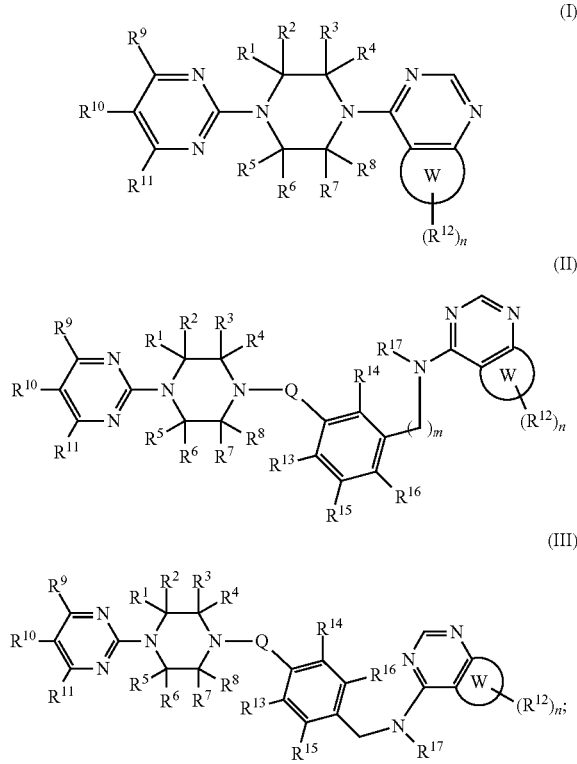
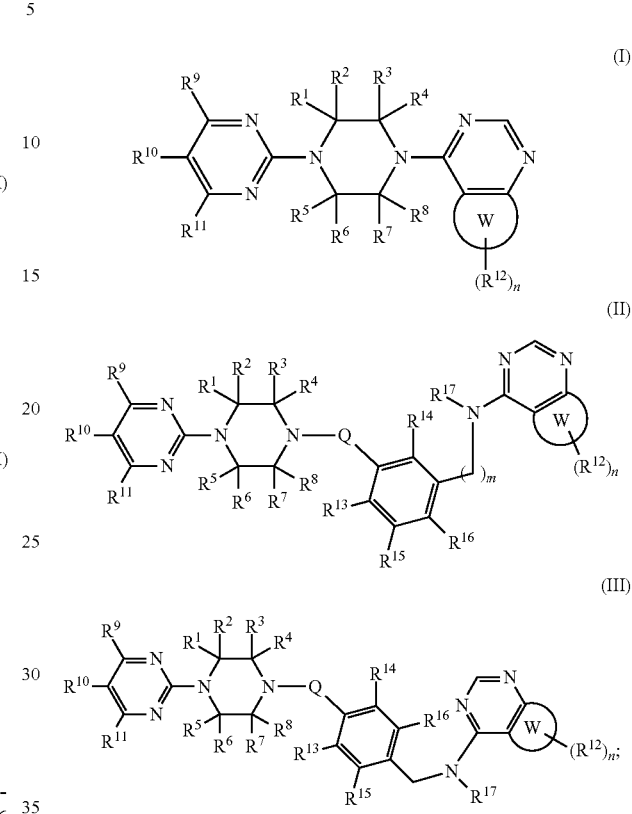

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and wherein each R is optionally substituted; and
each $R^{17}$ is independently selected from hydrogen or optionally substituted alkyl;
or a pharmaceutically acceptable salt thereof.

39. The method of embodiment 38, wherein the proliferative disorder is a tumor or a cancer in a human or animal subject.

40. The method of embodiment 39, wherein the cancer is selected from the group consisting of leukemia, non-small cell lung cancer, colon cancer, central nervous system (CNS) cancer, melanoma, ovarian cancer, renal cancer, prostate cancer, and breast cancer.

41. A method to reduce cell proliferation, said method comprising administering to a cell in an in vitro or in vivo environment, an effective amount of a compound of formula (I), (II), or (III):

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, R12, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and wherein each R is optionally substituted; and
each $R^{17}$ is independently selected from hydrogen or optionally substituted alkyl;
or a pharmaceutically acceptable salt thereof.

42. The method of embodiment 41, wherein the cell is a cancer cell, and wherein the cancer is selected from the group consisting of leukemia, non-small cell lung cancer, colon cancer, central nervous system (CNS) cancer, melanoma, ovarian cancer, renal cancer, prostate cancer, and breast cancer.

43. A method to induce cell death, said method comprising administering to a cell in an in vitro or in vivo environment, an effective amount of a compound of formula (I), (II), or (III):

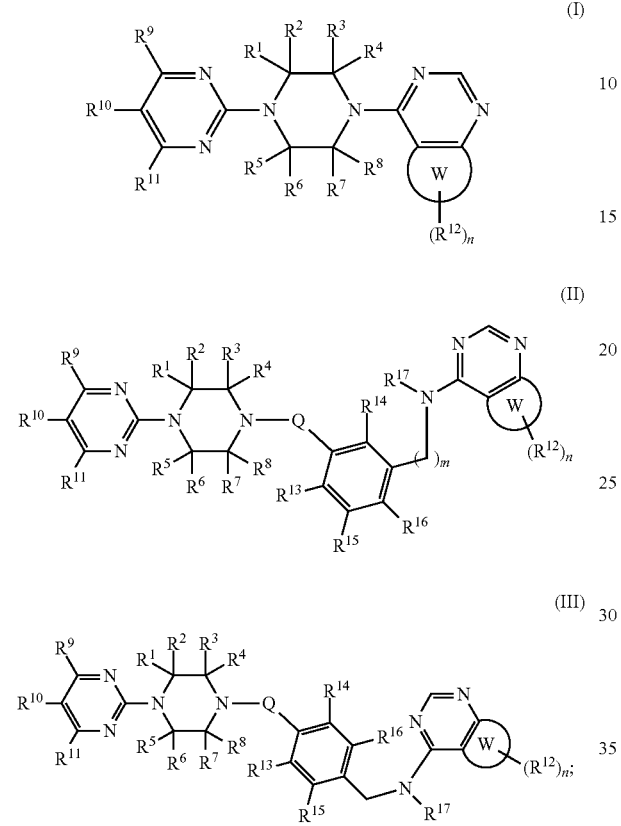

wherein m is 0 or 1;
each n is independently 0-6;
each W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each Q is $CH_2$, $SO_2$, or C=O;
each $R^1$, $R^2$, $R^3$, $R^4$, $R^5$, $R^6$, $R^7$, and $R^8$ is independently selected from hydrogen, optionally substituted alkyl, or optionally substituted aryl;
each $R^9$, $R^{10}$, $R^{11}$, $R^{12}$, $R^{13}$, $R^{14}$, $R^{15}$, and $R^{16}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclylalkyl, C6-C10 aryl, C5-C10 heteroaryl, C7-C12 arylalkyl, or C6-C12 heteroarylalkyl, and wherein each R is optionally substituted; and
each $R^{17}$ is independently selected from hydrogen or optionally substituted alkyl;
or a pharmaceutically acceptable salt thereof.

44. The compound of embodiment 1, wherein one or more $R^9$, $R^{10}$, $R^{11}$ or $R^{12}$ are independently halo.
45. The compound of embodiment 44, wherein each $R^{10}$ is bromo.
46. The compound of embodiment 44, wherein each $R^{12}$ is fluoro.
47. The compound of any of embodiments 44-46, wherein the compound is:

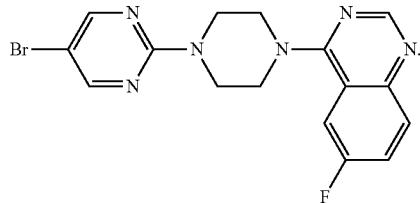 [SMILES: Fc1ccc2ncnc(N3CCN(c4ncc(Br)cn4)CC3)c2c1]

48. The compound of any of embodiments 44-46, wherein the compound is:

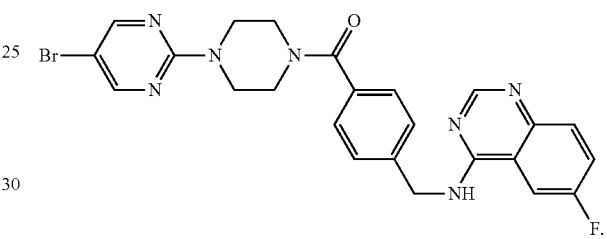

We claim:
1. A compound of formula (I):

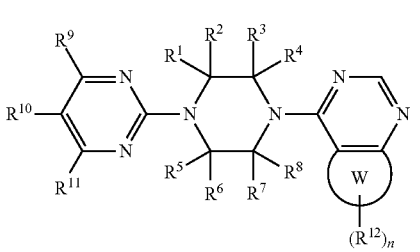

wherein
n is independently 0-6;
W represents an optionally substituted aryl or heteroaryl ring, which may be a monocyclic group with 5-6 ring atoms, or may be a 5-6 membered ring that is fused with or bonded to one or more additional aryl, heterocyclic, or heteroaryl rings;
each $R^1$, $R^2$, $R^3$, $R^4$, $R^5$, $R^6$, $R^7$, and $R^8$ is independently selected from hydrogen, optionally substituted alkyl, or optionally substituted aryl; and
each $R^9$, $R^{10}$, $R^{11}$, and $R^{12}$ is independently selected from hydrogen, optionally substituted alkyl, or optionally substituted aryl, halo, OR, $NR_2$, SR, S(O)R, $SO_2R$, $SO_2NR_2$, $NRSO_2R$, $NRCONR_2$, NRCOOR, NRCOR, CN, COOR, $CONR_2$, OOCR, COR, CH(OH)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 heterocyclyl, C4-C10 heterocyclyclalkyl, C6-C10 aryl, C5-C10 heteroaryl, C7-C12 arylalkyl, or C6-C12 heteroarylalkyl, and wherein each R is optionally substituted, with the proviso that $R^{10}$ must not be hydrogen; or a pharmaceutically acceptable salt thereof.

2. The compound of claim 1, wherein $R^{10}$ is independently selected from optionally substituted alkyl, optionally substituted aryl, halo, OR, $NR_2$, SR, CN, COOR, $CONR_2$, COR, CH(OH)R, and $NO_2$.

3. The compound of claim 1, wherein each $R^{12}$ is independently selected from optionally substituted alkyl, optionally substituted aryl, halo, OR, $NR_2$, SR, CN, COOR, $CONR_2$, COR, CH(OH)R, and $NO_2$.

4. The compound of claim 1, wherein the compound is:

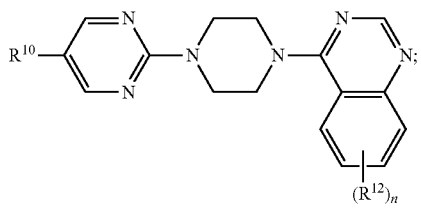

wherein $R^{10}$ is selected from the group consisting of optionally substituted alkyl and optionally substituted aryl;

and wherein each $R^{12}$ is independently selected from the group consisting of hydrogen, optionally substituted alkyl, optionally substituted aryl, halo, OR, $NR_2$, SR, CN COOR, $CONR_2$, COR, CH(OH)R, and $NO_2$.

5. The compound of claim 4, wherein the compound is:

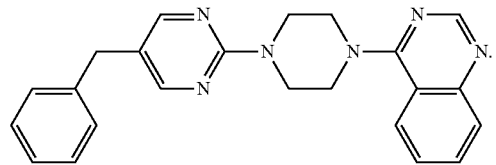 [SMILES: c1ccc(Cc2cnc(N3CCN(c4ncnc5ccccc45)CC3)nc2)cc1]

6. The compound of claim 1, wherein the compound is:

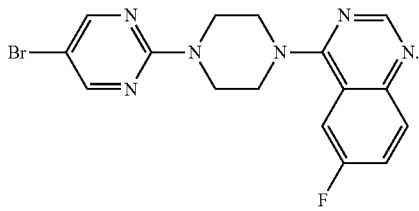

7. A pharmaceutical composition comprising a compound of claim 1 and at least one pharmaceutically acceptable excipient.

8. A method to inhibit a tyrosine kinase of a platelet derived growth factor receptor (PDGFR) comprising administering a pharmaceutical composition comprising a compound or salt of claim 1.

9. The method of claim 8, wherein the tyrosine kinase of the platelet derived growth factor receptor (PDGFR) is selected from the group consisting of PDGFRα, PDGFRβ, KIT, Flt3, and CSF1R.

* * * * *